(12) United States Patent
Cutler

(10) Patent No.: US 9,738,902 B2
(45) Date of Patent: Aug. 22, 2017

(54) MODIFIED PYR/PYL RECEPTORS ACTIVATED BY LIGANDS

(71) Applicant: The Regents of the University of California, Oakland, CA (US)

(72) Inventor: Sean R. Cutler, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/775,659

(22) PCT Filed: Mar. 11, 2014

(86) PCT No.: PCT/US2014/023403
§ 371 (c)(1),
(2) Date: Sep. 11, 2015

(87) PCT Pub. No.: WO2014/159394
PCT Pub. Date: Oct. 2, 2014

(65) Prior Publication Data
US 2016/0115500 A1  Apr. 28, 2016

Related U.S. Application Data

(60) Provisional application No. 61/783,874, filed on Mar. 14, 2013.

(51) Int. Cl.
*C12N 15/82* (2006.01)
*A01N 37/36* (2006.01)

(52) U.S. Cl.
CPC ......... *C12N 15/8273* (2013.01); *A01N 37/36* (2013.01); *C12N 15/8271* (2013.01); *C12N 15/8293* (2013.01)

(58) Field of Classification Search
None
See application file for complete search history.

(56) References Cited

U.S. PATENT DOCUMENTS

| | | | |
|---|---|---|---|
| 5,625,130 | A | 4/1997 | Grant et al. |
| 7,214,786 | B2 | 5/2007 | Kovalic et al. |
| 2004/0148654 | A1 | 7/2004 | Helentjaris |
| 2004/0214272 | A1 | 10/2004 | La Rosa et al. |
| 2005/0244971 | A1 | 11/2005 | Kim |
| 2006/0021088 | A1 | 1/2006 | Inze et al. |
| 2006/0179518 | A1 | 8/2006 | Hill et al. |
| 2007/0039067 | A1 | 2/2007 | Feldmann et al. |
| 2009/0105238 | A1 | 4/2009 | Filippini et al. |
| 2009/0320152 | A1 | 12/2009 | Steber et al. |
| 2011/0271408 | A1* | 11/2011 | Cutler .................... A01N 25/00 800/300 |

FOREIGN PATENT DOCUMENTS

| | | |
|---|---|---|
| CN | 101173287 A | 5/2008 |
| JP | 2007-222129 A | 9/2007 |
| WO | 03/008540 A2 | 1/2003 |
| WO | 2004/035798 A2 | 4/2004 |
| WO | 2010/093954 A2 | 8/2010 |

OTHER PUBLICATIONS

Park et al, Nature, Apr. 23, 2015, vol. 520, pp. 545-548 (abstract).*

Anonymous: "Improving plant water use efficiency: chemical and genetic solutions with applications to grasses—University of California", Jan. 1, 2013 (Jan. 1, 2013) Retrieved from the Internet on Jul. 16, 2014 at URL: http://portal.nifa.usda.gov/web/crisprojectpages/0216497-improving-plant-water-use-efficiency-chemical-and-genetic-solutions-with-applications-to-grasses.html.
Melcher et al., "Identification and mechanism of ABA receptor antagonism" Nature Structural Biology, 17(9):1102-1108 (Sep. 2010).
Santiago et al., "The abscisic acid receptor PYR1 in complex with abscisic acid", Nature, 462(7273):665-668 (Nov. 2009).
Santiago et al., "Structural insights into PYR/PYL/RCAR ABA receptors and PP2Cs" Plant Science, 182:3-11 (Mar. 2012).
International Search Report and Written Opinion from International Application No. PCT/US2014/023403, dated Jul. 28, 2014.
Cutler et al., "Abscisic Acid: Emergence of a Core Signaling Network,"Annual Review of Plant Biology, 61:651-679 (2010).
GenBank as accession No. NP_563626, available online Jan. 28, 2002.
GenBank as accession No. NP_565887, available online Jan. 28, 2002.
Fujii et al., "In vitro reconstitution of an abscisic acid signaling pathway," Nature, vol. 462, Dec. 2009, p. 660.
Lee, Sung Chul et al., "Functional roles of the pepper antimicrobial protein gene, CaAMP1, in abscisic acid signaling, and salt and drought tolerance in Arabidopsis," Planta (2009) 229:383-391.
Li et al., "DGP1, a drought-induced guard cell-specific promoter and its function analysis in tobacco plants," Science in China Ser. C Life Sciences, 2005, vol. 48, No. 2, pp. 181-186.
Masgrau et al.; "Inducible overexpression of oat arginine decarboxylase in transgenic tobacco plants"; 1997, The Plant Journal, vol. 11, No. 3, pp. 465-473.
Melcher et al., "A gate-latch-lock mechanism for hormone signaling by abscisic acid receptors," Nature 462: 602-608, 2009.
Mosquna et al., Potent and selective activation of abscisic acid receptors in vivo mutational stabilization of their agonist-bound conformation, Proc. Natl. Acad. Sci. USA., vol. 108., No. 51, Dec. 2011, pp. 20838-20843.
Nishimura, Noriyuki et al., "Structural Mechanism of Abscisic Acid Binding and Signaling by Dimeric PYR1," Science, Dec. 2009, 326(5958):1373-1379.
Peterson et al., "Structural basis for selective activation of ABA receptors," Nat. Struct. Mol. Biol., 2010, vol. 17, pp. 1109-1113.
Santiago et al., "Modulation of drought resistance by the abscisic acid receptor PYL5 through inhibition of clade A PP2Cs," The Plant Journal, 60:575-588, 2009.
Wang et al., "Molecular tailoring of farnesylation for plant drought tolerance and yield protection," Plant J., 2005, vol. 43, pp. 413-424.
Weiner et al., "Structural and Functional Insights into Core ABA Signaling," Current Opinion in Plant Biology, 2010, 13:495-502.
Williams et al.; "A possible role for kinase-associated protein phosphatase in the Arabidopsis CLAVATA1 signaling pathway"; 1997, Proc. Natl. Acad. Sci., vol. 94, pp. 10467-10472.
Xie et al., "Cloning, sequence analysis and prokaryotic expression of pathogenesis-induced protein (PIP) gene from peanut," Crops Research Institute, Guangdong Academy of Agricultural Sciences, China, Jan. 2009, XP002676969, Database accession No. 153:424228, abstract.

(Continued)

*Primary Examiner* — Eileen O Hara
(74) *Attorney, Agent, or Firm* — Kilpatrick Townsend & Stockton LLP

(57) ABSTRACT

Modified PYR/PYL receptors activated by orthogonal ligands are provided.

16 Claims, 14 Drawing Sheets

(56) References Cited

OTHER PUBLICATIONS

Spencer et al., "Segregation of transgenes in maize," *Plant Mol. Biol.*, 18(2):201-210 (Jan. 1992).
Gonzalez-Guzman et al., "Arabidopsis PYR/PYL!RCAR receptors play a major role in quantitative regulation of stomatal aperture and transcriptional response to abscisic acid," *The Plant Cell*, 24:2483-2496 (Jun. 2012).
Park et al., "Abscisic acid inhibits type 2C protein phosphatases via the PYR/PYL family of START proteins," *Science*, 342:1068-1071 (May 2009).
UniProtKP accession No. 049686, Mar 2, 2010.
EMBL accession No. AY042890, Feb 26, 2010.
Kline et al., "Abscisic Acid Receptors," Plant Physiology Oct. 2010 vol. 154 No. 2 479-482.
Chen, Inês, "ABA receptor diversity," SBKB, Nov. 2010 featured articles, retrieved Jun. 2, 2014, 3 pages. [doi:10.1038/sbkb.2010.49].
Yin et al., "Structural Insights into the mechanism of abscisic acid signaling by PYL proteins," *Nature Structural & Molecular Biology*, 16(12):1230-1237 (Dec. 2009) includes 1 additional supplemental page.
Miyazono et al., "Structural basis of abscisic acid signaling," *Nature*, 462:609-614 (Dec. 2009) includes 1 additional supplemental page.
Yue et al., "Regulators of PP2C Phosphatase Activity Function as Abscisic Acid Sensors," *Science*, 324:1064-1068 (May 2009).

\* cited by examiner

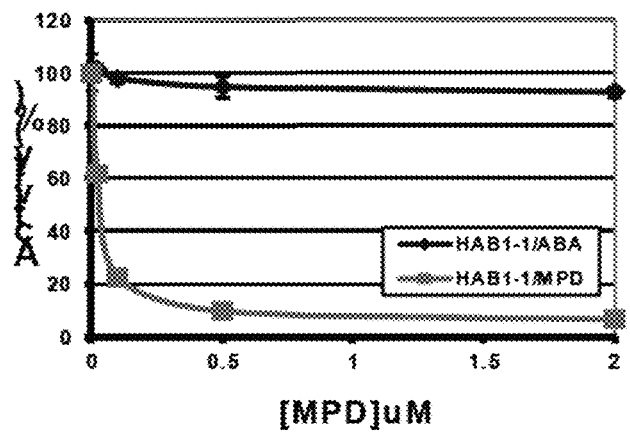
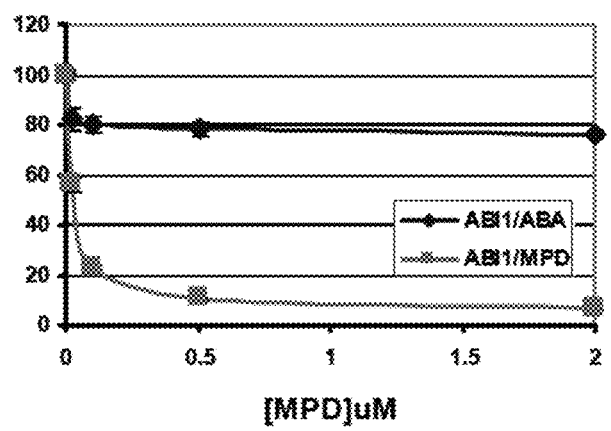
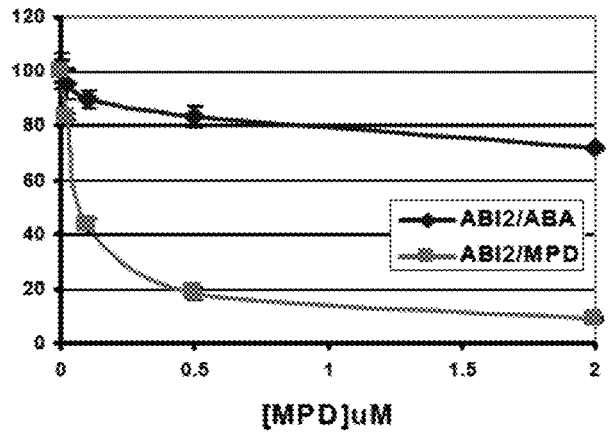
FIG. 1B

US 9,738,902 B2

MODIFIED PYR/PYL RECEPTORS ACTIVATED BY LIGANDS

CROSS-REFERENCE TO RELATED PATENT APPLICATIONS

The present patent application is the US National Stage entry of International Application No. PCT/US2014/023403, filed Mar. 11, 2014 which claims benefit of priority to US Provisional Patent Application No. 61/783,874, filed on Mar. 14, 2013, each of which is incorporated by reference.

BACKGROUND OF THE INVENTION

Rising temperatures and lessening fresh water supplies are two forms of environmental stress, also called abiotic stress, that lower the amount of food produced by agriculture. A key regulator of abiotic stress tolerance is the plant hormone abscisic acid (ABA), which is synthesized by plants in response to various abiotic stresses and orchestrates adaptive responses that enhance plant survival (Cutler, S. et al., *Annual Review of Plant Biology* (2010); Nambara, E. et al., *Annual Review of Plant Biology* 56:165-185 (2005)). Crop plants engineered to have increased ABA sensitivity show improved yield under conditions of drought (Wang, Y. et al., *Plant J* 43:413-424 (2005)). Moreover, the direct application of ABA or ABA analogs to plants in the field has been shown to improve water use efficiency (Hawkins, A. F. et al., Plant Growth Regulators for Agricultural and Amenity Use (British Crop Protection Council) (1987); Kreeb, K. H. et al., Structural and Functional Responses to Environmental Stresses (Balogh Scientific Books) (1989)); however, ABA has not been successfully commercialized for this use given its complicated production routes and high cost.

Interestingly, numerous fungicides and insecticides have shown stress-tolerance "side-effects" of unknown mechanism and have been commercialized for stress-tolerance uses, which demonstrates the strong interest in, and recognized need for chemical methods to control stress tolerance (Asrar, J. et al., In US 2009/0270254 A1 (USA, Monsanto Technology) (2003); Beckers, G. J. M. et al., Current Opinion in Plant Biology 10:425-431 (2007); Schulz, A. et al., In US 2007/0124839 A1 (USA, Bayer Crop Sciences) (2006)). An important driver of this interest has been the realization that the dramatic increases in corn yield achieved over last 100 years can be attributed largely to improvements in abiotic stress tolerance of new high-yielding corn varieties (Duvick, D. N. et al., *Crop Science* 39:1622-1630 (1999); Tollenaar, M. et al., *Field Crops Research* 75:161-169 (2002); Tollenaar, M. et al., *Crop Sci* 39:1597-1604 (1999)). Because ABA is recognized as the critical hormonal regulator of plant stress physiology, there is intense interest in modulating the ABA pathway in crops. One possible point at which to control the ABA signaling pathway is receptor proteins, which in principle would allow both chemical and genetic modulation of ABA signaling and stress tolerance.

Recently a new family of ABA receptors, the Pyrabactin resistance/PYR-like ("PYR/PYL") family, was identified as a modulator of ABA signaling (Park, S. Y. et al., *Science* 324:1068-1071 (2009)). The over-expression of the ABA receptor PYL5 confers drought tolerance on *Arabidopsis* plants (Santiago, J. et al., *The Plant Journal* 60(4):575-578 (2009)), validating this new receptor family as a key target for control of plant stress tolerance. However, gene over-expression can have adverse yield consequences, which are referred to as "yield drag". Yield drag is thought to occur because the unregulated activation of stress tolerance pathways, which is associated with slowed growth, occurs under normal conditions (i.e. in the absence of drought or other stressors). See, D. W., *J Exp Bot* 64(1): 83-108 (2013). One way to gain regulated control of ABA signaling is to develop chemical agents that activate ABA receptors (i.e. agonists). These can be applied to plants once drought or other stress conditions have ensued, which allows for selective protection in adverse conditions. This allows the benefits of stress tolerance to be realized without lowering yield under ideal growth conditions.

In principle, ABA could be used as an agonist to realize these advantages. However, it is a natural product that is costly to make and rapidly degraded by both UV photo-isomerization and metabolic inactivation. It also has physiological effects in mammals that could conceivably affect its suitability for use as an agrochemical (Guri, A. J. et al., *Clin Nutr.* (2010)).

BRIEF SUMMARY OF THE INVENTION

Mandipropamid

The present application provides a plant or cell comprising a heterologous expression cassette, the expression cassette comprising a promoter operably linked to a polynucleotide encoding a mutated PYR/PYL receptor polypeptide, wherein the mutated PYR/PYL receptor polypeptide is agonized by mandipropamid when the mandipropamid is contacted to the mutated PYR/PYL receptor polypeptide. Further provided are isolated nucleic acids that encode such mutated PYR/PYL polypeptides, as well as expression casettes comprising a promoter operably linked to a polynucleotide encoding such mutated PYR/PYL polypeptides.

In some embodiments, the amino acid of the mutated PYR/PYL receptor polypeptide corresponding to position K59 of SEQ ID NO:1 is X, wherein X is alanine, cysteine, aspartic acid, glutamic acid, phenylalanine, glycine, histidine, leucine, methionine, glutamine, arginine, serine, threonine, valine, tyrosine, asparagine, or tryptophan. In some embodiments, the mutated PYR/PYL receptor polypeptide further comprises at least one additional mutation at an amino acid corresponding to positions 89, 108, 122, and/or 159 in PYR1 (SEQ ID NO:1) wherein the mutation is selected from A89W, F108L, F108S, F108C, F108Q, F108I, F108T, F108N, F108V, F108A, F108E, F108G, S122G, F159L, F159I, F159C, F159T, F159V, F159A, F159M, or combinations thereof.

In some embodiments, the amino acid of the mutated PYR/PYL receptor polypeptide corresponding to position S122 of SEQ ID NO:1 is a glycine residue and position F108 of SEQ ID NO:1 is X, wherein X is leucine, serine, cysteine, glutamine, isoleucine, threonine, asparagine, valine, alanine, glutamic acid, or glycine. In some embodiments, the mutated PYR/PYL receptor polypeptide further comprises at least one additional mutation at an amino acid corresponding to positions 58, 81, 83, 87, 159, 160, and/or 164 in PYR 1 (SEQ ID NO:1) wherein the mutation is selected from Y58H, V81C, V81I, V81T, V83L, L87A, F159L, F159M, F159V, A160V, V164I, or combinations thereof.

In some embodiments, the mutated PYR/PYL receptor polypeptide comprises mutations at amino acids corresponding to positions 58, 108, and 122 in PYR 1 (SEQ ID NO:1) wherein the mutations are Y58H, F108A, and S122G. In some embodiments, the mutated PYR/PYL receptor polypeptide further comprises at least one additional mutation at an amino acid corresponding to positions 81 and/or 83 in PYR1 (SEQ ID NO:1) wherein the mutation is selected from V81I, V83L, or combinations thereof. In some embodiments, the mutated PYR/PYL receptor polypeptide further comprises at least one additional mutation at an amino acid corresponding to positions 159 and/or 160 in PYR1 (SEQ ID NO:1) wherein the mutation is selected from A160V, V164I, F159L, or combinations thereof.

In some embodiments, the mutated PYR/PYL receptor polypeptide comprises mutations at amino acids corresponding to positions 81, 108, 122, and 160 in PYR 1 (SEQ ID NO:1) wherein the mutations are V81I, F108A, S122G, and A160V.

In some embodiments, the mutated PYR/PYL receptor polypeptide comprises mutations at amino acids corresponding to positions 58, 81, 108, 122, and 159 in PYR 1 (SEQ ID NO:1) wherein the mutations are Y58H, V81I, F108A, S122G, and F159L.

In some embodiments, the mutated PYR/PYL receptor polypeptide comprises mutations at amino acids corresponding to positions 58, 81, 108, 122, and 164 in PYR 1 (SEQ ID NO:1) wherein the mutations are Y58H, V81I, F108A, S122G, and V164I.

In some embodiments, the mutated PYR/PYL receptor polypeptide comprises at least one mutation at an amino acid residue comprising the ligand-binding pocket of the PYR/PYL receptor polypeptide.

In some embodiments, the plant has improved abiotic stress tolerance when contacted with mandipropamid as compared to a plant lacking the expression cassette.

In some embodiments, the cell is a plant, animal, mammalian, or fungal cell.

In some embodiments, a seed, flower, leaf, fruit, processed food, or food ingredient from a plant as described herein is provided.

Also provided is a method of improving abiotic stress in a plant as described herein by contacting the plant with mandipropamid.

Also provided is a method of inhibiting seed germination in a plant as described herein by contacting the plant with mandipropamid.

Also provided is a method of making a mutated PYR/PYL receptor polypeptide that is agonized by mandipropamid when the mandipropamid is contacted to the mutated PYR/PYL receptor polypeptide, wherein the mandipropamid does not significantly agonize a wild-type PYR/PYL receptor polypeptide when the mandipropamid is contacted to the wild-type PYR/PYL receptor polypeptide, the method comprising (a) mutagenizing the wild-type PYR/PYL receptor polypeptide;
(b) contacting one or more mutated PYR/PYL receptor polypeptides with mandipropamid; and
(c) determining whether mandipropamid activates the one or more mutated PYR/PYL receptor polypeptides, wherein activation identifies the one or more mutated PYR/PYL receptor polypeptides as being agonized by mandipropamid.

In some embodiments, the method further comprises, prior to step (b), screening the mandipropamid to determine whether mandipropamid binds to the wild-type PYR/PYL receptor polypeptide prior to contacting the one or more mutated PYR/PYL receptor polypeptides with the mandipropamid.

Also provided is an expression cassette comprising a promoter operably linked to a polynucleotide encoding a mutated PYR/PYL receptor polypeptide, wherein the mutated PYR/PYL receptor polypeptide is agonized by mandipropamid when the mandipropamid is contacted to the mutated PYR/PYL receptor polypeptide. Also provided is an expression vector comprising the expression cassette.

Also provided is an isolated nucleic acid comprising a polynucleotide encoding a mutated PYR/PYL receptor polypeptide, wherein the mutated PYR/PYL receptor polypeptide is agonized by mandipropamid when the mandipropamid is contacted to the mutated PYR/PYL receptor polypeptide. Also provided is an expression vector comprising the nucleic acid.

Dichlobenil

The present application provides a plant or cell comprising a heterologous expression cassette, the expression cassette comprising a promoter operably linked to a polynucleotide encoding a mutated PYR/PYL receptor polypeptide, wherein the mutated PYR/PYL receptor polypeptide is agonized by dichlobenil when the dichlobenil is contacted to the mutated PYR/PYL receptor polypeptide. Further provided are isolated nucleic acids that encode such mutated PYR/PYL polypeptides, as well as expression casettes comprising a promoter operably linked to a polynucleotide encoding such mutated PYR/PYL polypeptides.

In some embodiments, the amino acid of the mutated PYR/PYL receptor polypeptide corresponding to position K59 of SEQ ID NO:1 is X, wherein X is alanine, cysteine, aspartic acid, glutamic acid, phenylalanine, glycine, histidine, leucine, methionine, glutamine, arginine, serine, threonine, valine, tyrosine, asparagine, or tryptophan. In some embodiments, the mutated PYR/PYL receptor polypeptide further comprises at least one additional mutation corresponding (relative to SEQ ID NO:1) to V83L, L87P, E94D, F108E, I110M, H115N, E141F, E141L, E141Y, E141H, E141Q, M158L, M158S, M158C, M158I, M158T, M158V, M158A, M158G, F159L, F159I, F159V, A160C, A160S, A160Y, A160I, A160T, A160N, A160V, T162L, T162Y, T162W, T162K, V164F, V164L, V164S, V164Y, V164C, V164H, V164Q, V164T, V164T, V164N, V164K, V164A, V164E, V164G, V164M, N167S, N167C, N167Q, N167T, N167A, N167D, N167G, V81I, V83L, A89C, L117C, E141Y, E141K, F159T, F159C, F159A, F159M, or A160G or combinations thereof.

In some embodiments, the amino acid of the mutated PYR/PYL receptor polypeptide corresponding to position A89 of SEQ ID NO:1 is a cysteine residue and further comprises at least one additional mutation corresponding to A141Y, A160G, V164K, or L117C, or combinations thereof.

In some embodiments, the amino acid of the mutated PYR/PYL receptor polypeptide corresponding to position L117 of SEQ ID NO:1 is a cysteine residue and further comprises at least one additional mutation corresponding to V164K.

In some embodiments, the amino acid of the mutated PYR/PYL receptor polypeptide corresponding to position E141 of SEQ ID NO:1 is a tyrosine residue and further comprises at least one additional mutation corresponding to A160G.

In some embodiments, the amino acid of the mutated PYR/PYL receptor polypeptide corresponding to position A160 of SEQ ID NO:1 is a glycine residue and further comprises at least one additional mutation corresponding to L117C or V164K or combinations thereof.

In some embodiments, the mutated PYR/PYL receptor polypeptide comprises at least one mutation at an amino acid residue comprising the ligand-binding pocket of the PYR/PYL receptor polypeptide.

In some embodiments, the plant has improved abiotic stress tolerance when contacted with dichlobenil as compared to a plant lacking the expression cassette.

In some embodiments, the cell is a plant, animal, mammalian, or fungal cell.

In some embodiments, a seed, flower, leaf, fruit, processed food, or food ingredient from a plant as described herein is provided.

Also provided is a method of improving abiotic stress in a plant as described herein by contacting the plant with dichlobenil.

Also provided is a method of inhibiting seed germination in a plant as described herein by contacting the plant with dichlobenil.

Also provided is a method of making a mutated PYR/PYL receptor polypeptide that is agonized by dichlobenil when the dichlobenil is contacted to the mutated PYR/PYL receptor polypeptide, wherein the dichlobenil does not significantly agonize a wild-type PYR/PYL receptor polypeptide when the dichlobenil is contacted to the wild-type PYR/PYL receptor polypeptide, the method comprising
(a) mutagenizing the wild-type PYR/PYL receptor polypeptide;
(b) contacting one or more mutated PYR/PYL receptor polypeptides with dichlobenil; and
(c) determining whether dichlobenil activates the one or more mutated PYR/PYL receptor polypeptides, wherein activation identifies the one or more mutated PYR/PYL receptor polypeptides as being agonized by dichlobenil.

In some embodiments, the method further comprises, prior to step (b), screening the dichlobenil to determine whether dichlobenil binds to the wild-type PYR/PYL receptor polypeptide prior to contacting the one or more mutated PYR/PYL receptor polypeptides with the dichlobenil.

Also provided is an expression cassette comprising a promoter operably linked to a polynucleotide encoding a mutated PYR/PYL receptor polypeptide, wherein the mutated PYR/PYL receptor polypeptide is agonized by dichlobenil when the dichlobenil is contacted to the mutated PYR/PYL receptor polypeptide. Also provided is an expression vector comprising the expression cassette.

Also provided is an isolated nucleic acid comprising a polynucleotide encoding a mutated PYR/PYL receptor polypeptide, wherein the mutated PYR/PYL receptor polypeptide is agonized by dichlobenil when the dichlobenil is contacted to the mutated PYR/PYL receptor polypeptide. Also provided is an expression vector comprising the nucleic acid.

Benzothiadiazole

The present application provides a plant or cell comprising a heterologous expression cassette, the expression cassette comprising a promoter operably linked to a polynucleotide encoding a mutated PYR/PYL receptor polypeptide, wherein the mutated PYR/PYL receptor polypeptide is agonized by benzothiadiazole when the benzothiadiazole is contacted to the mutated PYR/PYL receptor polypeptide. Further provided are isolated nucleic acids that encode such mutated PYR/PYL polypeptides, as well as expression casettes comprising a promoter operably linked to a polynucleotide encoding such mutated PYR/PYL polypeptides.

In some embodiments, the amino acid of the mutated PYR/PYL receptor polypeptide corresponding to position K59 of SEQ ID NO:1 is X, wherein X is alanine, cysteine, aspartic acid, glutamic acid, phenylalanine, glycine, histidine, leucine, methionine, glutamine, arginine, serine, threonine, valine, tyrosine, asparagine, or tryptophan. In some embodiments, the mutated PYR/PYL receptor polypeptide further comprises at least one additional mutation corresponding (relative to SEQ ID NO:1) to V81I, V83L, A89C, L117C, E141Y, E141K, M158I, M158T, M158C, M158V, F159L, F159T, F159C, F159I, F159V, F159A, F159M, A160G, T162Y, T162W, T162K, V164Y, and V164K, or combinations thereof.

In some embodiments, the amino acid of the mutated PYR/PYL receptor polypeptide corresponding to position A89 of SEQ ID NO:1 is a cysteine residue and further comprises at least one additional mutation corresponding to A141Y, A160G, V164K or L117C, or combinations thereof.

In some embodiments, the amino acid of the mutated PYR/PYL receptor polypeptide corresponding to position L117 of SEQ ID NO:1 is a cysteine residue and further comprises at least one additional mutation corresponding to V164K.

In some embodiments, the amino acid of the mutated PYR/PYL receptor polypeptide corresponding to position E141 of SEQ ID NO:1 is a tyrosine residue and further comprises at least one additional mutation corresponding to A160G.

In some embodiments, the amino acid of the mutated PYR/PYL receptor polypeptide corresponding to position A160 of SEQ ID NO:1 is a glycine residue and further comprises at least one additional mutation corresponding to L117C.

In some embodiments, the mutated PYR/PYL receptor polypeptide comprises at least one mutation at an amino acid residue comprising the ligand-binding pocket of the PYR/PYL receptor polypeptide.

In some embodiments, the plant has improved abiotic stress tolerance when contacted with benzothiadiazole as compared to a plant lacking the expression cassette.

In some embodiments, the cell is a plant, animal, mammalian, or fungal cell.

In some embodiments, a seed, flower, leaf, fruit, processed food, or food ingredient from a plant as described herein is provided.

Also provided is a method of improving abiotic stress in a plant as described herein by contacting the plant with benzothiadiazole.

Also provided is a method of inhibiting seed germination in a plant as described herein by contacting the plant with benzothiadiazole.

Also provided is a method of making a mutated PYR/PYL receptor polypeptide that is agonized by benzothiadiazole when the benzothiadiazole is contacted to the mutated PYR/PYL receptor polypeptide, wherein the benzothiadiazole does not significantly agonize a wild-type PYR/PYL receptor polypeptide when the benzothiadiazole is contacted to the wild-type PYR/PYL receptor polypeptide, the method comprising
(a) mutagenizing the wild-type PYR/PYL receptor polypeptide;
(b) contacting one or more mutated PYR/PYL receptor polypeptides with benzothiadiazole; and
(c) determining whether benzothiadiazole activates the one or more mutated PYR/PYL receptor polypeptides, wherein activation identifies the one or more mutated PYR/PYL receptor polypeptides as being agonized by benzothiadiazole.

In some embodiments, the method further comprises, prior to step (b), screening the benzothiadiazole to determine whether benzothiadiazole binds to the wild-type PYR/PYL receptor polypeptide prior to contacting the one or more mutated PYR/PYL receptor polypeptides with the benzothiadiazole.

Also provided is an expression cassette comprising a promoter operably linked to a polynucleotide encoding a mutated PYR/PYL receptor polypeptide, wherein the mutated PYR/PYL receptor polypeptide is agonized by benzothiadiazole when the benzothiadiazole is contacted to the mutated PYR/PYL receptor polypeptide. Also provided is an expression vector comprising the expression cassette.

Also provided is an isolated nucleic acid comprising a polynucleotide encoding a mutated PYR/PYL receptor polypeptide, wherein the mutated PYR/PYL receptor polypeptide is agonized by benzothiadiazole when the benzothiadiazole is contacted to the mutated PYR/PYL receptor polypeptide. Also provided is an expression vector comprising the nucleic acid.

Benoxacor

The present application provides a plant or cell comprising a heterologous expression cassette, the expression cassette comprising a promoter operably linked to a polynucleotide encoding a mutated PYR/PYL receptor polypeptide, wherein the mutated PYR/PYL receptor polypeptide is agonized by benoxacor when the benoxacor is contacted to the mutated PYR/PYL receptor polypeptide. Further provided are isolated nucleic acids that encode such mutated PYR/PYL polypeptides, as well as expression casettes comprising a promoter operably linked to a polynucleotide encoding such mutated PYR/PYL polypeptides.

In some embodiments, the amino acid of the mutated PYR/PYL receptor polypeptide corresponding to position K59 of SEQ ID NO:1 is X, wherein X is alanine, cysteine, aspartic acid, glutamic acid, phenylalanine, glycine, histidine, leucine, methionine, glutamine, arginine, serine, threonine, valine, tyrosine, asparagine, or tryptophan. In some embodiments, the mutated PYR/PYL receptor polypeptide further comprises at least one additional mutation corresponding (relative to SEQ ID NO:1) to L87F, A89I, A89W, S92I, S92W, M158C, M158V, M158T, F159V, and T162W, or combinations thereof.

In some embodiments, the amino acid of the mutated PYR/PYL receptor polypeptide corresponding to position A89 of SEQ ID NO:1 is an isoleucine residue and further comprises at least one additional mutation corresponding to S92I or S92W or combinations thereof.

In some embodiments, the mutated PYR/PYL receptor polypeptide comprises at least one mutation at an amino acid residue comprising the ligand-binding pocket of the PYR/PYL receptor polypeptide.

In some embodiments, the plant has improved abiotic stress tolerance when contacted with benoxacor as compared to a plant lacking the expression cassette.

In some embodiments, the cell is a plant, animal, mammalian, or fungal cell.

In some embodiments, a seed, flower, leaf, fruit, processed food, or food ingredient from a plant as described herein is provided.

Also provided is a method of improving abiotic stress in a plant as described herein by contacting the plant with benoxacor.

Also provided is a method of inhibiting seed germination in a plant as described herein by contacting the plant with benoxacor.

Also provided is a method of making a mutated PYR/PYL receptor polypeptide that is agonized by benoxacor when the benoxacor is contacted to the mutated PYR/PYL receptor polypeptide, wherein the benoxacor does not significantly agonize a wild-type PYR/PYL receptor polypeptide when the benoxacor is contacted to the wild-type PYR/PYL receptor polypeptide, the method comprising (a) mutagenizing the wild-type PYR/PYL receptor polypeptide;

(b) contacting one or more mutated PYR/PYL receptor polypeptides with benoxacor; and (c) determining whether benoxacor activates the one or more mutated PYR/PYL receptor polypeptides, wherein activation identifies the one or more mutated PYR/PYL receptor polypeptides as being agonized by benoxacor.

In some embodiments, the method further comprises, prior to step (b), screening the benoxacor to determine whether benoxacor binds to the wild-type PYR/PYL receptor polypeptide prior to contacting the one or more mutated PYR/PYL receptor polypeptides with the benoxacor.

Also provided is an expression cassette comprising a promoter operably linked to a polynucleotide encoding a mutated PYR/PYL receptor polypeptide, wherein the mutated PYR/PYL receptor polypeptide is agonized by benoxacor when the benoxacor is contacted to the mutated PYR/PYL receptor polypeptide. Also provided is an expression vector comprising the expression cassette.

Also provided is an isolated nucleic acid comprising a polynucleotide encoding a mutated PYR/PYL receptor polypeptide, wherein the mutated PYR/PYL receptor polypeptide is agonized by benoxacor when the benoxacor is contacted to the mutated PYR/PYL receptor polypeptide. Also provided is an expression vector comprising the nucleic acid.

Fludioxonil

The present application provides a plant or cell comprising a heterologous expression cassette, the expression cassette comprising a promoter operably linked to a polynucleotide encoding a mutated PYR/PYL receptor polypeptide, wherein the mutated PYR/PYL receptor polypeptide is agonized by fludioxonil when the fludioxonil is contacted to the mutated PYR/PYL receptor polypeptide. Further provided are isolated nucleic acids that encode such mutated PYR/PYL polypeptides, as well as expression cassettes comprising a promoter operably linked to a polynucleotide encoding such mutated PYR/PYL polypeptides.

In some embodiments, the amino acid of the mutated PYR/PYL receptor polypeptide corresponding to position K59 of SEQ ID NO:1 is X, wherein X is alanine, cysteine, aspartic acid, glutamic acid, phenylalanine, glycine, histidine, leucine, methionine, glutamine, arginine, serine, threonine, valine, tyrosine, asparagine, or tryptophan. In some embodiments, the mutated PYR/PYL receptor polypeptide further comprises at least one additional mutation corresponding (relative to SEQ ID NO:1) to V81Y, V81I, V83L, L87F, L87P, S92F, E94A, E94S, E94D, F108L, Y120F, Y120A, Y120G, Y120M, E141Y, M158C, M158V, M158I, M158T, F159T, F159V, F159A, A160C, T162W, V164K, N167C, N167H, and N167V, or combinations thereof.

In some embodiments, the amino acid of the mutated PYR/PYL receptor polypeptide corresponding to position E94 of SEQ ID NO:1 is an alanine residue and further comprises at least one additional mutation corresponding to Y120A or N167C or combinations thereof.

In some embodiments, the amino acid of the mutated PYR/PYL receptor polypeptide corresponding to position Y120 of SEQ ID NO:1 is an alanine residue and further comprises at least one additional mutation corresponding to N167C or E141Y or combinations thereof.

In some embodiments, the mutated PYR/PYL receptor polypeptide comprises at least one mutation at an amino acid residue comprising the ligand-binding pocket of the PYR/PYL receptor polypeptide.

In some embodiments, the plant has improved abiotic stress tolerance when contacted with fludioxonil as compared to a plant lacking the expression cassette.

In some embodiments, the cell is a plant, animal, mammalian, or fungal cell.

In some embodiments, a seed, flower, leaf, fruit, processed food, or food ingredient from a plant as described herein is provided.

Also provided is a method of improving abiotic stress in a plant as described herein by contacting the plant with fludioxonil.

Also provided is a method of inhibiting seed germination in a plant as described herein by contacting the plant with fludioxonil.

Also provided is a method of making a mutated PYR/PYL receptor polypeptide that is agonized by fludioxonil when the fludioxonil is contacted to the mutated PYR/PYL receptor polypeptide, wherein the fludioxonil does not significantly agonize a wild-type PYR/PYL receptor polypeptide when the fludioxonil is contacted to the wild-type PYR/PYL receptor polypeptide, the method comprising
(a) mutagenizing the wild-type PYR/PYL receptor polypeptide;
(b) contacting one or more mutated PYR/PYL receptor polypeptides with fludioxonil; and
(c) determining whether fludioxonil activates the one or more mutated PYR/PYL receptor polypeptides, wherein activation identifies the one or more mutated PYR/PYL receptor polypeptides as being agonized by fludioxonil.

In some embodiments, the method further comprises, prior to step (b), screening the fludioxonil to determine whether fludioxonil binds to the wild-type PYR/PYL receptor polypeptide prior to contacting the one or more mutated PYR/PYL receptor polypeptides with the fludioxonil.

Also provided is an expression cassette comprising a promoter operably linked to a polynucleotide encoding a mutated PYR/PYL receptor polypeptide, wherein the mutated PYR/PYL receptor polypeptide is agonized by fludioxonil when the fludioxonil is contacted to the mutated PYR/PYL receptor polypeptide. Also provided is an expression vector comprising the expression cassette.

Also provided is an isolated nucleic acid comprising a polynucleotide encoding a mutated PYR/PYL receptor polypeptide, wherein the mutated PYR/PYL receptor polypeptide is agonized by fludioxonil when the fludioxonil is contacted to the mutated PYR/PYL receptor polypeptide. Also provided is an expression vector comprising the nucleic acid.

BRIEF DESCRIPTION OF THE DRAWINGS

FIG. 1B shows graphs of data from assays determining the $IC_{50}$ values for mandipropamid-mediated inhibition of HAB1, ABI1 and ABI2.

DEFINITIONS

Figure 1A:
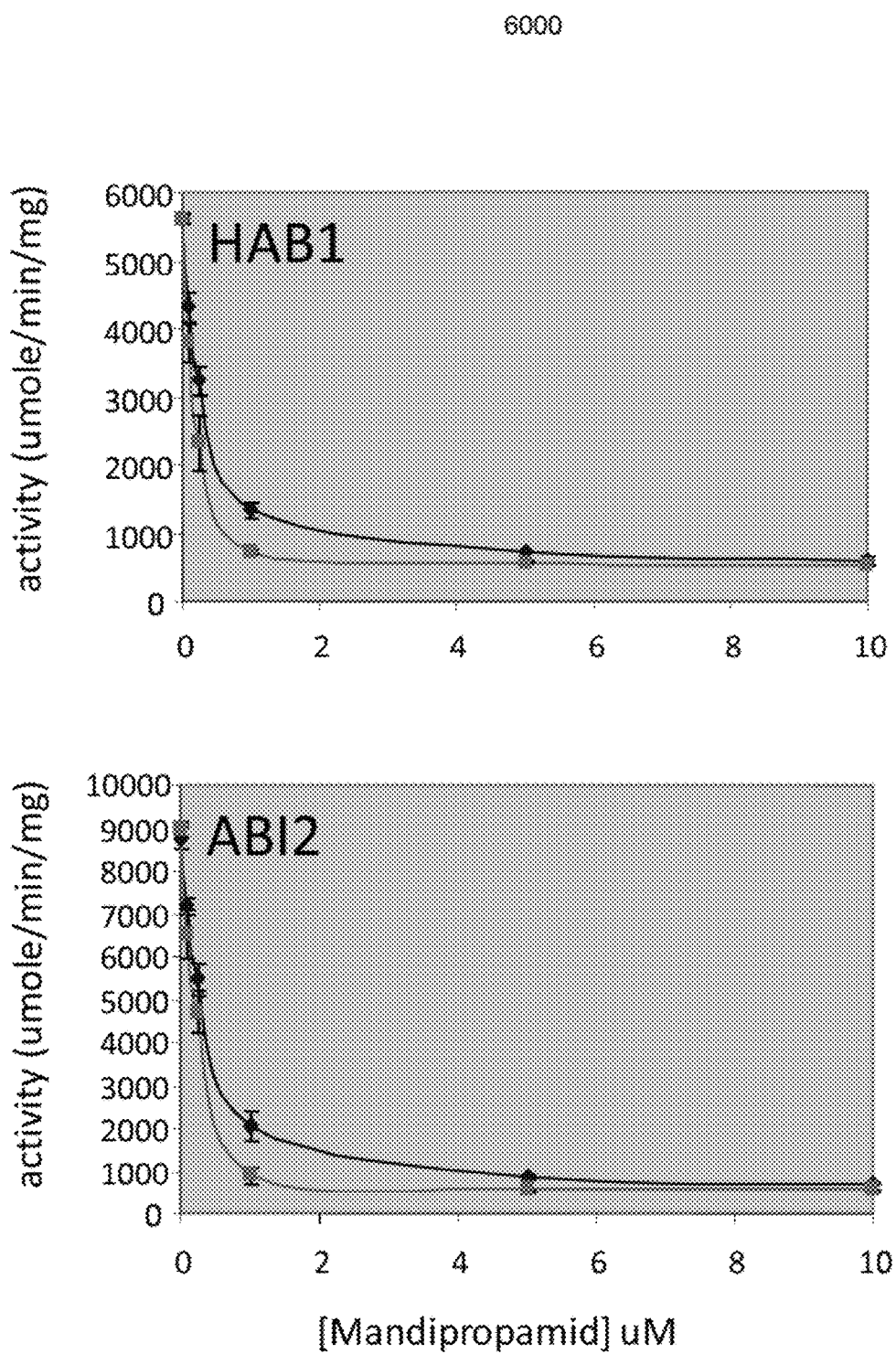
FIG. 1A summarizes data from saturable inhibition of HAB1 and ABI2 PP2C activity by manipropamid.

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to *Arabidopsis* PYR1 (SEQ ID NO:1), PYL1 (SEQ ID NO:2), PYL2 (SEQ ID NO:3), PYL3 (SEQ ID NO:4), PYL4 (SEQ ID NO:5), PYL5 (SEQ ID NO:6), PYL6 (SEQ ID NO:7), PYL7 (SEQ ID NO:8), PYL8 (SEQ ID NO:9), PYL9 (SEQ ID NO:10), PYL10 (SEQ ID NO:11), PYL11 (SEQ ID NO:12), PYL12 (SEQ ID NO:13), or PYL13 (SEQ ID NO:14), or to any of SEQ ID NOS:15-89.

A "wild-type PYR/PYL receptor polypeptide" refers to a naturally occurring PYR/PYL receptor polypeptide that mediates abscisic acid (ABA) and ABA analog signaling.

A "mutated PYR/PYL receptor polypeptide" or "modified PYR/PYL receptor polypeptide" refers to a PYR/PYL receptor polypeptide that is a variant from a naturally-occurring (i.e., wild-type) PYR/PYL receptor polypeptide. As used herein, a mutated or modified PYR/PYL receptor polypeptide comprises one or more amino acid substitutions relative to a corresponding wild-type PYR/PYL receptor polypeptide. In this context, a "mutated" polypeptide or "modified" polypeptide can be generated by any method for generating non-wild type nucleotide sequences. A mutated PYR/PYL receptor polypeptide may or may not mediate abscisic acid (ABA) and ABA analog signaling.

An amino acid "corresponding to position [X] of [specific sequence]" refers to an amino acid in a polypeptide of interest that aligns with the equivalent amino acid of a specified sequence. Generally, as described herein, the amino acid corresponding to a position of a PYR/PYL receptor polypeptide can be determined using an alignment algorithm such as BLAST. In typical embodiments, "correspondence" of amino acid positions is determined by aligning to a region of the PYR/PYL receptor polypeptide comprising SEQ ID NO:1, as discussed further herein. When a PYR/PYL receptor polypeptide sequence differs from SEQ ID NO:1 (e.g., by changes in amino acids or addition or deletion of amino acids), it may be that a particular mutation associated with agonization by a chemical that does not agonize wild-type PYR/PYL will not be in the same position number as it is in SEQ ID NO:1. For example, amino acid position K86 of PYL1 (SEQ ID NO:2) aligns with amino acid position K59 in SEQ ID NO:1, as can be readily illustrated in an alignment of the two sequences. In this example, a mutation at amino acid position 86 in SEQ ID NO:2 corresponds to position 59 in SEQ ID NO:1.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. Embodiments of the present invention provide for nucleic acids encoding polypeptides that are substantially identical to any of SEQ ID NOS:1-89 and have at least one of the amino acid mutations described herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

It is contemplated that a substitution mutation in a mutated PYR/PYL receptor polypeptide includes not only those specific amino acid substitutions called out in the specification, e.g. in the Examples section or in any of the Figures or Tables of the specification, but also includes amino acids that are conservative substitutions for those specific amino acids, so long as the conservatively substituted amino acid is not the wild-type amino acid. As a non-limiting example, where a mutated PYR/PYL receptor polypeptide comprises a serine-to-threonine substitution, it is contemplated that the mutated PYR/PYL receptor polypeptide may alternatively comprise a serine-to-alanine substitution, as threonine and alanine are conservative substitutions for one another; but the mutated PYR/PYL receptor polypeptide would not comprise a serine-to-serine substitution, as serine is the amino acid that is present in the wild-type PYR/PYL polypeptide.

As used herein, the term "agonist" or "agonists" refers to a molecule identified using in vitro and in vivo assays for activity of a described target protein as described elsewhere herein. Agonists are agents that, e.g., induce or activate the expression of a described target protein or bind to, stimulate, increase, open, activate, facilitate, enhance activation, sensitize or up-regulate the activity of described target protein (or encoding polynucleotide). Agonists include naturally occurring and synthetic molecules. In some embodiments, the agonists are agrichemicals, e.g., fungicides, herbicides, pesticides, and/or fertilizers. Assays for determining whether an agonist "agonizes" or "does not agonize" a target protein include, e.g., contacting putative agonists to purified target protein(s) and then determining the functional effects on the described target protein activity, as described above, or contacting putative agonists to cells expressing the target protein(s) and then determining the functional effects on the described target protein activity, as described above. One of skill in the art will be able to determine whether an assay is suitable for determining whether an agonist agonizes or does not agonize a target protein. Samples or assays comprising described target protein that are treated with a putative agonist are compared to control samples without the agonist to examine the extent of effect. Control samples (untreated with agonists) are assigned a relative activity value of 100%. Agonism of the described target protein is achieved when the activity value relative to the control is 110%, optionally 150%, optionally 200%, 300%, 400%, 500%, or 1000-3000% or more higher.

As used herein, the term "orthogonal receptor" refers to a receptor that has been modified to selectively recognize new ligands ("orthogonal ligands"). As used herein, the term "orthogonal ligand" refers to an agent that agonizes a mutated or modified PYR/PYL receptor polypeptide but which does not agonize (or substantially agonize) a wild-type PYR/PYL receptor polypeptide.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

As used herein, the terms "abiotic stress," "stress," or "stress condition" refer to the exposure of a plant, plant cell, or the like, to a non-living ("abiotic") physical or chemical agent that has an adverse effect on metabolism, growth, development, propagation, or survival of the plant (collectively, "growth"). A stress can be imposed on a plant due, for example, to an environmental factor such as water (e.g., flooding, drought, or dehydration), anaerobic conditions (e.g., a lower level of oxygen or high level of $CO_2$), abnormal osmotic conditions, salinity, or temperature (e.g., hot/heat, cold, freezing, or frost), a deficiency of nutrients or exposure to pollutants, or by a hormone, second messenger, or other molecule. Anaerobic stress, for example, is due to a reduction in oxygen levels (hypoxia or anoxia) sufficient to produce a stress response. A flooding stress can be due to prolonged or transient immersion of a plant, plant part, tissue, or isolated cell in a liquid medium such as occurs during monsoon, wet season, flash flooding, or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Salinity-induced stress (salt-stress) can be associated with or induced by a perturbation in the osmotic potential of the intracellular or extracellular environment of a cell. As used herein, the term "abiotic stress tolerance" or "stress tolerance" refers to a plant's increased resistance or tolerance to abiotic stress as compared to plants under normal conditions and the ability to perform in a relatively superior manner when under abiotic stress conditions. As used herein, the terms "drought resistance" and "drought tolerance" are used to refer to a plant's increased resistance or tolerance to stress induced by a reduction in water availability, as compared to normal circumstances, and the ability of the plant to function and survive in lower-water environments, and perform in a relatively superior manner.

DETAILED DESCRIPTION OF THE INVENTION

I. Introduction

Surprisingly, proteins belonging to a family of abscisic acid (ABA) receptors, the PYR/PYL receptor family, can be mutated to bind and respond to dichlorobenil, benzothiadiazole, benoxacor, mandipropamid and fludioxonil.

Thus, it is possible to alter PYR/PYL receptor polypeptides so that one of the above-listed compounds can be used to selectively activate them. Moreover, because the mutated PYR/PYL receptor (orthogonal receptor) can be selectively activated by applying an orthogonal ligand (e.g., as part of a program to improve plant response to water deficit), the problem of "yield drag" can be avoided. Yield drag is traditionally associated with receptor over-expression, in which gene over-expression during normal or optimal growth conditions (i.e., in the absence of drought or other stressors) is associated with slowed growth. This does not occur with the disclosed mutated receptors because they possess a K59R mutation, which abolishes ABA responsiveness.

II. Mutated PYR/PYL Receptor Polypeptides

Mutated PYR/PYL receptor polypeptides are provided that are agonized by chemicals (dichlorobenil, benzothiadiazole, benoxacor, and/or mandipropamid) that do not agonize wild-type PYR/PYL receptor polypeptides, as well as polynucleotides encoding mutated PYR/PYL receptor polypeptides that are agonized by the chemicals that do not agonize wild-type PYR/PYL receptor polypeptides; expression cassettes and expression vectors comprising polynucleotides encoding mutated PYR/PYL receptor polypeptides that are agonized by chemicals that do not agonize wild-type PYR/PYL receptor polypeptides; plants comprising mutated PYR/PYL receptor polypeptides that are agonized by chemicals that do not agonize wild-type PYR/PYL receptor polypeptides; methods of making plants comprising mutated PYR/PYL receptor polypeptides that are agonized by chemicals that do not agonize wild-type PYR/PYL receptor polypeptides; and methods of making mutated PYR/PYL receptor polypeptides.

A wide variety of wild-type (naturally occurring) PYR/PYL polypeptide sequences are known in the art. Although PYR1 was originally identified as an abscisic acid (ABA) receptor in *Arabidopsis*, in fact PYR1 is a member of a group of at least 14 proteins (PYR/PYL proteins) in the same protein family in *Arabidopsis* that also mediate ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, *BMC Evol. Biol.* 8:286 (2008). In some embodiments, a wild-type PYR/PYL receptor polypeptide comprises any of SEQ ID NOs:1-89. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs:1-89.

Mutated PYR/PYL receptor polypeptides are variants from (i.e., when compared to) naturally-occurring (i.e., wild-type) PYR/PYL receptor polypeptides. Variants can include, e.g., fusion proteins, deletions, insertions, or mutations that retain activity. In some embodiments, a mutated PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, or 89 and comprises 1, 2, 3, 4, 5, 6, or more mutations as described herein relative to a corresponding wild-type PYR/PYL receptor polypeptide. In addition, in some embodiments, the mutated PYR/PYL receptor polypeptide further comprises an amino- and/or carboxyl terminal fusion with a heterologous amino acid sequence.

In situations where additional variants or orthologs of the above sequences are desired for insertion of one or more of the mutations described herein, it can be useful to generate sequence alignments to identify conserved amino acid or motifs (i.e., where alteration in sequences may alter protein function) and regions where variation occurs in alignment of sequences (i.e., where variation of sequence is not likely to significantly affect protein activity). Some useful consensus sequences for identifying PYR/PYL polypeptides include, e.g., EXLXXXDXXXXXXXXXXXGGXHXL (SEQ ID NO:90), CxSxxxxxxxxAPxxxxWxxxxxFxxPxxxxxFxxxC (SEQ ID NO:91), GxxRxVxxxSxxPAxxSxExLxxxD (SEQ ID NO:92), and/or GGxHRLxNYxS (SEQ ID NO:93). In addition, more specific consensus sequences can be represented by aligning subsets of the 14 members of the *Arabidopsis* PYR/PYL proteins, though it is believed these consensus sequences are more broadly applicable to other plant orthologous sequences. Examples of such consensus sequences include, e.g.,

```
PYR1 to PYL12
                                          (SEQ ID NO: 94)
CxSxxxxxxxxAPxxxxWxxxxxFxxPxxxxxFxxxC (SEQ ID NO: 95)
GxxRxVxxxSxxPAxxSxExLxxxD (SEQ ID NO: 93)
GGxHRLxNYxS (SEQ ID NO: 96)
ESxxVDxPxGxxxxxTxxFxxxxxxxNLxxL PYL1-12 consensus
                                          (SEQ ID NO: 97)
CxSxxxxxxxxAPxxxxWxxxxxFxxPxxxKxFxxxC (SEQ ID NO: 98)
GxxRxVxxxSxLPAxxSxExLxxxD (SEQ ID NO: 93)
GGxHRLxNYxS (SEQ ID NO: 99)
ESxxVDxPxGNxxxxTxxFxxxxxxxNLxxL PYL1-6 Consensus
                                          (SEQ ID NO: 100)
HxxxxxxxxxCxSxxxxxxxAPxxxxWxxxxxFxxPxxYKxFxxxC (SEQ ID NO: 101)
VGxxRxVxVxSGLPAxxSxExLxxxDxxxxxxxFxxxGGxHRLxNYxSVT (SEQ ID NO: 102)
VxESYxVDxPxGNxxxxTxxFxDxxxxxNLQxL PYL7-10 Consensus
                                          (SEQ ID NO: 103)
HxHxxxxxQCxSxLVKxIxAPxHxVWSxVRRFDxPQKYKPFxSRCxVxGx (SEQ ID NO: 104)
ExGxxREVxxKSGLPATxSTExLExLDDxEHILxIxIxGGDHRLKNYSSxxxxHxExIxGx (SEQ ID NO: 105)
xGTxxxESFVVDVPxGNTKxxTCxFVExLIxCNLxSLAxxxERL PYL11-13 Consensus
                                          (SEQ ID NO: 106)
CxSxxVxTIxAPLxLVWSILRxFDxPxxxxxFVKxCxxxSGxGG (SEQ ID NO: 107)
GSVRxVTxVSxxPAxFSxERLxELDDESHVMxxSIIGGxHRLVNYxSKT (SEQ ID NO: 108)
KKTVVVESYVVDVPEGxxEExTxxFxDxIxxxNLxSLAKL.
```

Accordingly, in some embodiments, the mutated PYR/PYL polypeptides as described herein comprise one or more of the above-described consensus sequences or conservative variants thereof, albeit with at least one or more of the amino acid changes indicated herein for orthologous chemical responsiveness.

The inventors have found a number of mutations that affect response to chemicals. In becoming responsive to non-ABA chemicals as described herein, the mutated PYR/PYL polypeptides described herein can be triggered to generate ABA-like induced responses similar to responses observed in wild type plants contacted with exogenous ABA. For example, plants expressing mutated PYR/PYL polypeptides as described herein and contacted with the appropriate chemical (dichlorobenil, benzothiadiazole, benoxacor, fludioxonil and mandipropamid) will exhibit improved stress (e.g., cold, heat, salinity, drought or other stress) tolerance, increased bud dormancy, increased seed dormancy (inhibited seed germination) and/or maturation, abscission of leaves and fruits.

With regard to mandipropamid, the inventors have found a series of mutations can be introduced into PYR/PYL proteins to confer in vitro and in vivo responsiveness to mandipropamid. It has been discovered that a combination of a mutation corresponding to K59R in SEQ ID NO:1 and any of A89W, F108L, F108S, F108C, F108Q, F108I, F108T, F108N, F108V, F108A, F108E, F108G, S122G, F159L, F159I, F159C, F159T, F159V, F159A, F159M result in responsiveness of PYR/PYL polypeptides to mandipropamid. A K59 mutation disrupts ABA responsiveness in the modified PYR/PYL receptor protein. While a mutation corresponding to K59R was used in the Examples, it believed based on prior results (e.g., as described in US Patent Publication No. 2011/0271408) with other K59 mutations that any K59X (where X is alanine, cysteine, aspartic acid, glutamic acid, phenylalanine, glycine, histidine, leucine, methionine, glutamine, arginine, serine, threonine, valine, tyrosine, asparagine, or tryptophan) can be used in the mutation combinations described herein for mandipropamid (as well as other chemicals described herein). It has been further discovered that additional mutations described in more detail below further improve the sensitivity of response to mandipropamid. Accordingly, in some cases, the modified PYR/PYL receptor protein contains two, three, four, five, six, or more mutations in order for the protein to be agonized by a chemical agonist.

Similarly, mutated PYR/PYL polypeptides are also provided that are agonized for other chemicals (e.g., dichlorobenil, benzothiadiazole, fludioxonil and benoxacor).

Any of the mutations described herein can be made in the polypeptides of any of SEQ ID NOS:1-89 or in polypeptides substantially identical to any of SEQ ID NOS:1-89. Alternatively, any of the mutations described above can be made in a polypeptide comprising any of the consensus sequences that identify PYR/PYL proteins, for example as set forth herein.

Embodiments provide for use of the above polypeptides and/or nucleic acid sequences, encoding such polypeptides, in the methods and compositions (e.g., expression cassettes, plants, etc.). The isolation of a polynucleotide sequence encoding a plant wild-type PYR/PYL receptor (e.g., from plants where PYR/PYL sequences have not yet been identified) may be accomplished by a number of techniques. For instance, oligonucleotide probes based on the PYR/PYL coding sequences disclosed (e.g., as listed in the SEQUENCE LISTING) here can be used to identify the desired wild-type PYR/PYL gene in a cDNA or genomic DNA library. To construct genomic libraries, large segments of genomic DNA are generated by random fragmentation, e.g., using restriction endonucleases, and are ligated with vector DNA to form concatemers that can be packaged into the appropriate vector. To prepare a cDNA library, mRNA is isolated from the desired tissue, such as a leaf from a particular plant species, and a cDNA library containing the gene transcript of interest is prepared from the mRNA. Alternatively, cDNA may be prepared from mRNA extracted from other tissues in which PYR/PYL gene is expressed.

The cDNA or genomic library can then be screened using a probe based upon the sequence of a PYR/PYL gene disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids encoding PYR/PYL can be amplified from nucleic acid samples using amplification techniques. For instance, polymerase chain reaction (PCR) technology can be used to amplify the coding sequences of PYR/PYL directly from genomic DNA, from cDNA, from genomic libraries or cDNA libraries. PCR and other in vitro amplification methods may also be useful, for example, to clone polynucleotide sequences encoding PYR/PYL to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M., Gelfand, D., Sninsky, J. and White, T., eds.), Academic Press, San Diego (1990). Appropriate primers and probes for identifying sequences from plant tissues are generated from comparisons of the sequences provided here with other related genes.

In some embodiments, the partial or entire genome of a number of plants has been sequenced and open reading frames identified. By a BLAST search, one can identify the coding sequence for wild-type PYR/PYL in various plants.

III. Chemical Agonists and Agonist Formulations

Embodiments of the present invention provide for agricultural chemical formulations formulated for contacting to mutated PYR/PYL receptor polypeptides and/or plants comprising mutated PYR/PYL receptor polypeptides, wherein the formulation comprises an agonist of a mutated PYR/PYL polypeptide of the present invention. Agrochemicals are often prepared and applied to plants as esters or salts, which may improve uptake and efficacy. The action of ubiquitous cellular esterases can convert esters (or homologous compounds such as the S-methyl derivatives of acibenzolar) into free acids or alcohols, which are the bioactive forms.

Mandipropamid

It was found that mutating the amino acid corresponding to K59 in SEQ ID NO:1, along with introducing at least one more amino acid mutation (corresponding to the designated position at SEQ ID NO:1) selected from A89W, F108L, F108S, F108C, F108Q, F108I, F108T, F108N, F108V, F108A, F108E, F108G, S122G, F159L, F159I, F159C, F159T, F159V, F159A, and F159M in the PYR/PYL receptor polypeptide, resulted in activation of the modified receptor by mandipropamid. A non-limiting list of exemplary combinations of mutations that result in modified PYR/PYL receptor being agonized by mandipropamid includes:

| | | | | | |
|---|---|---|---|---|---|
| K59R | A89W | | | | |
| K59R | F108L | | | | |
| K59R | F108S | | | | |
| K59R | F108C | | | | |
| K59R | F108Q | | | | |
| K59R | F108I | | | | |
| K59R | F108T | | | | |
| K59R | F108N | | | | |
| K59R | F108V | | | | |
| K59R | F108A | | | | |
| K59R | F108E | | | | |
| K59R | F108G | | | | |
| K59R | S122G | | | | |
| K59R | F159L | | | | |
| K59R | F159I | | | | |
| K59R | F159C | | | | |
| K59R | F159T | | | | |
| K59R | F159V | | | | |
| K59R | F159A | | | | |
| K59R | F159M | | | | |
| K59R | F108Q | S122G | | | |
| K59R | F108A | S122G | | | |
| K59R | F108I | S122G | | | |
| K59R | F108A | S122G | V81C | | |
| K59R | F108A | S122G | V81I | | |
| K59R | F108A | S122G | V81T | | |
| K59R | F108A | S122G | V83L | | |
| K59R | F108A | S122G | L87A | | |
| K59R | F108A | S122G | F159L | | |
| K59R | F108A | S122G | F159M | | |
| K59R | F108A | S122G | F159V | | |
| K59R | F108A | S122G | A160V | | |
| K59R | F108A | S122G | V164I | | |
| Y58H | K59R | F108A | S122G | | |
| Y58H | K59R | V81I | F108A | S122G | |
| | K59R | V81I | F108A | S122G | A160V |
| Y58H | K59R | V81I | F108A | F159L | |
| Y58H | K59R | V81I | F108A | S122G | V164I |
| Y58H | K59R | V81I | F108A | S122G | F159L |
| Y58H | K59R | V83L | F108A | S122G | |

In some embodiments, the modified PYR/PYL receptor proteins comprise one of the combinations of the mutations described above and are substantially identical to any of SEQ ID NOS:1-89. In some embodiments, the present invention provides for a polynucleotide encoding one or more of said modified PYR/PYL receptor polypeptides, or a plant expressing such a polypeptide.

Dichlobenil

It was found that mutating the amino acid corresponding to K59 in SEQ ID NO:1, along with introducing at least one more amino acid mutation (corresponding to the designated position at SEQ ID NO:1) selected from V83L, L87P, E94D, F108E, I110M, H115N, E141F, E141L, E141Y, E141H, E141Q, M158L, M158S, M158C, M158I, M158T, M158V, M158A, M158G, F159L, F159I, F159V, A160C, A160S, A160Y, A160I, A160T, A160N, A160V, T162L, T162Y, T162W, T162K, V164F, V164L, V164S, V164Y, V164C, V164H, V164Q, V164T, V164T, V164N, V164K, V164A, V164E, V164G, V164M, N167S, N167C, N167Q, N167T, N167A, N167D, N167G, V81I, V83L, A89C, L117C, E141Y, E141K, F159T, F159C, F159A, F159M, and A160G in the PYR/PYL receptor polypeptide, resulted in activation of the modified receptor by dichlobenil. A non-limiting list of exemplary combinations of mutations (with the triple mutants at the bottom having further increased sensitivity to dichlobenil) that result in modified PYR/PYL receptor being agonized by dichlobenil includes:

| | | |
|---|---|---|
| K59R | V83L | |
| K59R | L87P | |
| K59R | E94D | |
| K59R | F108E | |
| K59R | I110M | |
| K59R | H115N | |
| K59R | E141F | |
| K59R | E141L | |
| K59R | E141Y | |
| K59R | E141H | |
| K59R | E141Q | |
| K59R | M158L | |
| K59R | M158S | |
| K59R | M158C | |
| K59R | M158I | |
| K59R | M158T | |
| K59R | M158V | |
| K59R | M158A | |
| K59R | M158G | |
| K59R | F159L | |
| K59R | F159I | |
| K59R | F159V | |
| K59R | A160G | |
| K59R | A160S | |
| K59R | A160Y | |
| K59R | A160I | |
| K59R | A160T | |
| K59R | A160N | |
| K59R | A160V | |
| K59R | T162L | |
| K59R | T162Y | |
| K59R | T162W | |
| K59R | T162K | |
| K59R | V164F | |
| K59R | V164L | |
| K59R | V164S | |
| K59R | V164Y | |
| K59R | V164C | |
| K59R | V164H | |
| K59R | V164Q | |
| K59R | V164T | |
| K59R | V164N | |
| K59R | V164K | |
| K59R | V164A | |
| K59R | V164E | |
| K59R | V164G | |
| K59R | V164M | |
| K59R | N167S | |
| K59R | N167C | |
| K59R | N167Q | |
| K59R | N167T | |
| K59R | N167A | |
| K59R | N167D | |
| K59R | N167G | |
| K59R | A89C | E141Y |
| K59R | A89C | A160G |
| K59R | A89C | V164K |
| K59R | A89C | L117C |
| K59R | L117C | V164K |
| K59R | E141Y | A160G |
| K59R | A160G | V164K |
| K59R | A160G | L117C |

In some embodiments, the modified PYR/PYL receptor proteins comprise one of the combinations of the mutations described above and are substantially identical to any of SEQ ID NOS:1-89. In some embodiments, the present invention provides for a polynucleotide encoding one or more of said modified PYR/PYL receptor polypeptides, or a plant expressing such a polypeptide.

Benzothiadiazole

It was found that mutating the amino acid corresponding to K59 in SEQ ID NO:1, along with introducing at least one more amino acid mutation (corresponding to the designated position at SEQ ID NO:1) selected from V81I, V83L, A89C, L117C, E141Y, E141K, M158I, M158T, M158C, M158V, F159L, F159T, F159C, F159I, F159V, F159A, F159M, A160G, T162Y, T162W, T162K, V164Y, and V164K in the PYR/PYL receptor polypeptide, resulted in activation of the modified receptor by benzothiadiazole. A non-limiting list of exemplary combinations of mutations (with the triple mutants at the bottom having further increased sensitivity to benzothiadiazole) that result in modified PYR/PYL receptor being agonized by benzothiadiazole includes:

| | | |
|---|---|---|
| K59R | V81I | |
| K59R | V83L | |
| K59R | A89C | |
| K59R | L117C | |
| K59R | E141Y | |
| K59R | E141K | |
| K59R | M158I | |
| K59R | M158T | |
| K59R | M158C | |
| K59R | M158V | |
| K59R | F159L | |
| K59R | F159T | |
| K59R | F159C | |
| K59R | F159I | |
| K59R | F159V | |
| K59R | F159A | |
| K59R | F159M | |
| K59R | A160G | |
| K59R | T162Y | |
| K59R | T162W | |
| K59R | T162K | |
| K59R | V164Y | |
| K59R | V164K | |
| K59R | A89C | E141Y |
| K59R | A89C | A160G |
| K59R | A89C | V164K |
| K59R | A89C | L117C |
| K59R | L117C | V164K |
| K59R | E141Y | A160G |
| K59R | A160G | V164K |
| K59R | A160G | L117C |

In some embodiments, the modified PYR/PYL receptor proteins comprise one of the combinations of the mutations described above and are substantially identical to any of SEQ ID NOS:1-89. In some embodiments, the present invention provides for a polynucleotide encoding one or more of said modified PYR/PYL receptor polypeptides, or a plant expressing such a polypeptide.

Benoxacor

It was found that mutating the amino acid corresponding to K59 in SEQ ID NO:1, along with introducing at least one more amino acid mutation (corresponding to the designated position at SEQ ID NO:1) selected from L87F, A89I, A89W, S92I, S92W, M158C, M158V, M158T, F159V, and T162W in the PYR/PYL receptor polypeptide, resulted in activation of the modified receptor by benoxacor. A non-limiting list of exemplary combinations of mutations (with the triple mutants at the bottom having further increased sensitivity to benoxacor) that result in modified PYR/PYL receptor being agonized by benoxacor includes:

| | | |
|---|---|---|
| K59R | L87F | |
| K59R | A89I | |
| K59R | A89W | |
| K59R | S92I | |
| K59R | S92W | |
| K59R | M158C | |
| K59R | M158V | |
| K59R | M158T | |
| K59R | F159V | |
| K59R | T162W | |
| K59R | A89I | S92I |
| K59R | A89I | S92W |

In some embodiments, the modified PYR/PYL receptor proteins comprise one of the combinations of the mutations described above and are substantially identical to any of SEQ ID NOS:1-89. In some embodiments, the present invention provides for a polynucleotide encoding one or more of said modified PYR/PYL receptor polypeptides, or a plant expressing such a polypeptide.

Fludioxonil

It was found that mutating the amino acid corresponding to K59 in SEQ ID NO:1, along with introducing at least one more amino acid mutation (corresponding to the designated position at SEQ ID NO:1) selected from V81Y, V81I, V83L, L87F, L87P, S92F, E94A, E94S, E94D, F108L, Y120F, Y120A, Y120G, Y120M, E141Y, M158C, M158V, M158I, M158T, F159T, F159V, F159A, A160C, T162W, V164K, N167C, N167H, and N167V in the PYR/PYL receptor polypeptide, resulted in activation of the modified receptor by fludioxonil. A non-limiting list of exemplary combinations of mutations (with the triple mutants at the bottom having further increased sensitivity to benoxacor) that result in modified PYR/PYL receptor being agonized by fludioxonil includes:

| | | |
|---|---|---|
| K59R | V81Y | |
| K59R | V81I | |
| K59R | V83L | |
| K59R | L87F | |
| K59R | L87P | |
| K59R | S92F | |
| K59R | E94A | |
| K59R | E94S | |
| K59R | E94D | |
| K59R | F108L | |
| K59R | Y120F | |
| K59R | Y120A | |
| K59R | Y120G | |
| K59R | Y120M | |
| K59R | E141Y | |
| K59R | M158C | |
| K59R | M158V | |
| K59R | M158I | |
| K59R | M158T | |
| K59R | F159T | |
| K59R | F159V | |
| K59R | F159A | |
| K59R | A160C | |
| K59R | T162W | |
| K59R | V164K | |
| K59R | N167C | |
| K59R | N167H | |
| K59R | N167V | |
| K59R | E94A | Y120A |
| K59R | E94A | N167C |
| K59R | Y120A | N167C |
| K59R | Y120A | E141Y |

In some embodiments, the modified PYR/PYL receptor proteins comprise one of the combinations of the mutations described above and are substantially identical to any of SEQ ID NOS:1-89. In some embodiments, the present invention provides for a polynucleotide encoding one or more of said modified PYR/PYL receptor polypeptides, or a plant expressing such a polypeptide.

Chemical agonists can be prepared by a variety of methods known to one of skill in the art, for example, those described in Comprehensive Organic Transformations, 2nd ed., Richard C. Larock, 1999. The starting materials for the methods described above are commercially available (Sigma-Aldrich) or can be prepared by methods known to one of skill in the art.

In some embodiments, the agricultural chemical formulations contemplated are formulated for contacting to plants. The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal). Any agriculturally suitable carrier known to one skilled in the art would be acceptable and is contemplated for use in the present invention. Optionally, the formulations can also include at least one surfactant, herbicide, fungicide, pesticide, or fertilizer.

Contacting the agricultural chemical formulation to the mutated PYR/PYL receptor polypeptide can be performed in vitro (e.g., wherein the mutated PYR/PYL receptor polypeptide exists in a purified form or is expressed in yeast cells) or in vivo (e.g., wherein the mutated PYR/PYL receptor polypeptide is expressed by a plant). Contacting the agricultural chemical formulation to the mutated PYR/PYL receptor polypeptide in vitro can be performed using a variety of known methods, e.g., by applying the formulation to protein binding assays, mammalian or yeast two-hybrid assays, competition assays, or cell-based assays using other organisms.

Contacting the agricultural chemical formulation to the mutated PYR/PYL receptor polypeptide in vivo (e.g., to a plant) can be performed using a variety of known methods, e.g., by spraying, atomizing, dusting or scattering the compositions over the propagation material or brushing or pouring or otherwise contacting the compositions over the plant or, in the event of seed, by coating, encapsulating, or otherwise treating the seed. In an alternative to directly treating a plant or seed before planting, the formulations of the invention can also be introduced into the soil or other media into which the seed is to be planted. In some embodiments, a carrier is also used in this embodiment. The carrier can be solid or liquid, as noted above. In some embodiments peat is suspended in water as a carrier of the chemical agonist, and this mixture is sprayed into the soil or planting media and/or over the seed as it is planted.

IV. Methods of Making Mutated PYR/PYL Receptor Polypeptides

Embodiments of the present invention provide for methods of making mutated PYR/PYL receptor polypeptides that are agonized by a chemical agonist that does not agonize a wild-type PYR/PYL receptor polypeptide. In some embodiments the method comprises mutagenizing the wild-type PYR/PYL receptor polypeptide, contacting one or more mutated PYR/PYL receptor polypeptides with the putative chemical agonist, and determining whether the chemical activates the one or more mutated PYR/PYL receptor polypeptides, wherein activation identifies the one or more mutated PYR/PYL receptor polypeptides as being agonized by the chemical.

Mutated PYR/PYL receptor polypeptides can be constructed by mutating the DNA sequences that encode the corresponding wild-type PYR/PYL receptor polypeptide (e.g., a wild-type PYR/PYL polypeptide of any of SEQ ID NOS:1-89 or a corresponding variant from which the mutant PYR/PYL receptor polypeptide of the invention is derived), such as by using techniques commonly referred to as site-directed mutagenesis. Nucleic acid molecules encoding the wild-type PYR/PYL receptor polypeptide can be mutated by a variety of polymerase chain reaction (PCR) techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, N Y, 1990).

By way of non-limiting example, mutagenesis may be accomplished by means of error-prone PCR amplification (ePCR), which modifies PCR reaction conditions (e.g., using error-prone polymerases, varying magnesium or manganese concentration, or providing unbalanced dNTP ratios) in order to promote increased rates of error in DNA replication. Kits for ePCR mutagenesis are commercially available, such as the GeneMorph® PCR Mutagenesis kit (Stratagene) and Diversify® PCR Random Mutagenesis Kit (Clontech). Briefly, DNA polymerase (e.g., Taq polymerase), salt (e.g., $MgCl_2$, $MgSO_4$, or $MnSO_4$), dNTPs in unbalanced ratios, reaction buffer, and DNA template are combined and subjected to standard PCR amplification according to manufacturer's instructions. Following ePCR amplification, the reaction products are cloned into a suitable vector to construct a mutagenized library, which can then be transformed into suitable cells (e.g., yeast cells) for subsequent screening (e.g., via a two-hybrid screen) as described below.

Alternatively, mutagenesis can be accomplished by recombination. Briefly, a mutant library is generated through using in vitro homologous recombination by random fragmentation of a parent DNA followed by reassembly using PCR, resulting in randomly introduced point mutations. Methods of performing DNA recombination-based mutagenesis are known in the art (see, e.g., Stebel, S. C. et al., *Methods Mol Biol* 352:167-190 (2007)).

Optionally, multiple rounds of mutagenesis may be performed in order to improve the efficiency of mutant proteins isolated. Thus, in some embodiments, PYR/PYL mutants isolated from ePCR and subsequent screening may be pooled and used as templates for later rounds of mutagenesis.

V. Screening for Agonism of Mutated PYR/PYL Receptor Polypeptides

Embodiments of the present invention also provide for methods of screening putative chemical agonists to determine whether the putative agonist agonizes a mutated PYR/PYL receptor polypeptide, but does not significantly agonize a wild-type PYR/PYL receptor polypeptide, when the putative agonist is contacted to the PYR/PYL receptor polypeptide. As used herein, an agent "agonizes" a PYR/PYL receptor protein if the presence of the agent results in activation or up-regulation of activity of the receptor, e.g., to increase downstream signaling from the PYR/PYL receptor. For the present invention, an agent agonizes a PYR/PYL receptor if, when the agent is present at a concentration no greater than 200 μM, contacting the agent to the PYR/PYL receptor results in activation or up-regulation of the activity of the PYR/PYL receptor. If an agent does not induce activation or up-regulation of a PYR/PYL receptor protein's activity when the agent is present at a concentration no greater than 200 μM, then the agent does not significantly agonize the PYR/PYL receptor. As used herein, "activation" requires a minimum threshold of activity to be induced by the agent. Determining whether this minimum threshold of activity has been met can be accomplished, e.g., by using an enzymatic phosphatase assay that sets a minimum value for the level of enzymatic activity that must be induced, or by using an enzymatic phosphatase assay in the presence of a colorimetric detection reagent (e.g., para-nitrophenylphosphate) wherein the minimum threshold of activity has been met if a color change is observed.

A number of different screening protocols can be utilized to identify chemical agents that agonize a mutated PYR/PYL receptor polypeptide but not a wild-type PYR/PYL receptor polypeptide. Screening can take place using isolated, purified or partially purified reagents. In some embodiments, purified or partially purified PYR/PYL polypeptide can be used.

Alternatively, cell-based or plant-based methods of screening can be used. For example, cells that naturally express a wild-type PYR/PYL receptor polypeptide or that recombinantly express a wild-type or mutated PYR/PYL receptor polypeptide can be used. In some embodiments, the cells used are plant cells, animal cells, bacterial cells, fungal cells, including but not limited to yeast cells, insect cells, or mammalian cells. In general terms, the screening methods involve screening one or more chemical agents to identify an agent that agonizes the activity of a mutated PYR/PYL receptor polypeptide (e.g., activating the mutated PYR/PYL receptor polypeptide or increasing expression of the mutated PYR/PYL receptor polypeptide or of a transcript encoding a mutated PYR/PYL receptor polypeptide), but that does not agonize the activity of a wild-type PYR/PYL receptor polypeptide. Optionally, the screening method may involve two screening processes: first, screening a plurality of putative agonists to identify compounds that weakly interact with a wild-type PYR/PYL receptor polypeptide ("weak ligands"), then screening those weak ligands against wild-type PYR/PYL receptor polypeptide and a plurality of mutagenized PYR/PYL receptor polypeptides to determine which mutated PYR/PYL receptor polypeptides are agonized by weak ligands and which weak ligands selectively agonize only mutated PYR/PYL receptor polypeptides and not wild-type PYR/PYL receptor polypeptides.

Binding Assays

Optionally, preliminary screens can be conducted by screening for agents capable of binding to a wild-type PYR/PYL receptor polypeptide. Pre-selection of weak-binding ligands improves the frequency of isolating mutated PYR/PYL receptor polypeptides that are agonized by the agent, presumably because fewer alterations of the ligand binding site are required to achieve molecular recognition.

Binding assays can involve contacting a wild-type PYR/PYL receptor polypeptide with one or more chemical agents and allowing sufficient time for the protein and chemical agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to the PYR/PYL polypeptide or displacement of labeled substrates (e.g., labeled agrochemical). The PYR/PYL polypeptide protein utilized in such assays can be naturally expressed, cloned or synthesized.

Agonist Assays

Agonist assays can involve screening putative chemical agonists (which may or may not have been pre-selected as weak binding ligands) to determine which putative agonists agonize at least one mutated PYR/PYL receptor polypeptides but not a wild-type PYR/PYL receptor polypeptide, and/or screening mutagenized PYR/PYL receptor polypeptides with putative chemical agonists (which may or may not have been pre-selected as weak binding ligands) to determine which mutagenized PYR/PYL receptor polypeptides are agonized by the putative agonist.

Any number of assays can be used to screen for agonists of mutated PYR/PYL receptor polypeptides. One activity assay involves testing whether a putative agonist can induce binding of a mutated PYR/PYL protein to a type 2 protein phosphatase (PP2C) polypeptide in an agonist-specific fashion. Mammalian or yeast two-hybrid approaches (see, e.g., Bartel, P. L. et. al. *Methods Enzymol*, 254:241 (1995)) can be used to identify polypeptides or other molecules that interact or bind when expressed together in a cell. In some embodiments, agents that agonize a mutated PYR/PYL receptor polypeptide, but not a wild-type PYR/PYL receptor polypeptide, are identified in a two-hybrid assay between a PYR/PYL polypeptide and a type 2 protein phosphatase (PP2C) polypeptide, wherein an agonist is identified as an agent that activates or enables binding of the PYR/PYL polypeptide and the PP2C polypeptide. Thus, the two polypeptides bind in the presence, but not in the absence of the agent. Optionally, both positive and negative selection schemes can be utilized in the two-hybrid assay. For example, a yeast two-hybrid assay may utilize a URA3 reporter strain to conduct both positive and negative selection; growth of the URA strain in the absence of exogenously supplied uracil enables positive selection for mutants that improve agonist responsiveness (i.e. agonist-promoted protein-protein interaction), while growth on FOA (5-fluoro-orotic acid, which is metabolized by URA3 to a toxic metabolite) allows selection against mutants that promote agonist response (e.g. to remove mutants that lead to constitutive, i.e. unliganded, interactions).

Screening for a compound that increases the expression of a mutated PYR/PYL receptor polypeptide, but not a wild-type PYR/PYL receptor polypeptide, is also provided. Screening methods generally involve conducting cell-based or plant-based assays in which test compounds are contacted with one or more cells expressing PYR/PYL polypeptide, and then detecting an increase in PYR/PYL expression (either transcript or translation product). Assays can be performed with cells that naturally express wild-type PYR/PYL or in cells recombinantly altered to express mutated or wild-type PYR/PYL. Various controls can be conducted to ensure that an observed activity is authentic, including running parallel reactions with cells that lack the reporter construct or by not contacting a cell harboring the reporter construct with test compound.

Agents and mutated PYR/PYL receptor polypeptides that are initially identified by any of the foregoing screening methods can be further tested to validate the apparent activity and/or determine other biological effects of the agent and/or mutated PYR/PYL receptor polypeptide. In some cases, the identified agent and/or mutated PYR/PYL receptor polypeptide is tested for the ability to effect plant stress (e.g., drought tolerance), seed germination, or another phenotype affected by ABA. A number of such assays and phenotypes are known in the art and can be employed according to the methods of the invention.

VI. Recombinant Expression Vectors

Once a polynucleotide sequence encoding a mutated PYR/PYL receptor polypeptide is obtained, it can also be used to prepare an expression cassette for expressing the mutated PYR/PYL receptor polypeptide in a transgenic plant, directed by a heterologous promoter. Increased expression of mutated PYR/PYL polynucleotide is useful, for example, to produce plants that will be able to respond to a chemical agonist that does not agonize an endogenous PYR/PYL receptor protein, thereby enhancing abiotic stress resistance.

Any of a number of means well known in the art can be used to drive mutated PYR/PYL activity or expression in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, the mutated PYR/PYL polynucleotide can be expressed constitutively (e.g., using the CaMV 35S promoter).

To use a polynucleotide sequence for a mutated PYR/PYL receptor polypeptide in the above techniques, recombinant DNA vectors suitable for transformation of plant cells are prepared. Techniques for transforming a wide variety of higher plant species are well known and described in the technical and scientific literature. See, e.g., Weising et al. *Ann. Rev. Genet.* 22:421-477 (1988). A DNA sequence coding for the mutated PYR/PYL receptor polypeptide preferably will be combined with transcriptional and translational initiation regulatory sequences which will direct the transcription of the sequence from the gene in the intended tissues of the transformed plant.

For example, a plant promoter fragment may be employed to direct expression of the mutated PYR/PYL polynucleotide in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill in the art.

Alternatively, the plant promoter may direct expression of the mutated PYR/PYL receptor protein in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO/2005/085449; U.S. Pat. No. 6,653,535; Li et al., *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include anaerobic conditions, elevated temperature, or the presence of light.

If proper protein expression is desired, a polyadenylation region at the 3'-end of the coding region should be included. The polyadenylation region can be derived from a naturally occurring PYR/PYL gene, from a variety of other plant genes, or from T-DNA.

The vector comprising the sequences (e.g., promoters or PYR/PYL coding regions) will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, the mutated PYR/PYL nucleic acid sequence is expressed recombinantly in plant cells. A variety of different expression constructs, such as expression cassettes and vectors suitable for transformation of plant cells can be prepared. Techniques for transforming a wide variety of higher plant species are well known and described in the technical and scientific literature. See, e.g., Weising et al. *Ann. Rev. Genet.* 22:421-477 (1988). A DNA sequence coding for a PYR/PYL protein can be combined with cis-acting (promoter) and trans-acting (enhancer) transcriptional regulatory sequences to direct the timing, tissue type and levels of transcription in the intended tissues of the transformed plant. Translational control elements can also be used.

Embodiments of the present invention also provide for a mutated PYR/PYL nucleic acid operably linked to a promoter which, in some embodiments, is capable of driving the transcription of the PYR/PYL coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoter can be chosen and employed to differentially direct gene expression, e.g., in some or all tissues of a plant or animal.

Constitutive Promoters

A promoter fragment can be employed to direct expression of a mutated PYR/PYL nucleic acid in all transformed cells or tissues, e.g., as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a mutated PYR/PYL receptor protein (Comai et al., *Plant Mol. Biol.* 15:373 (1990)).

Other examples of constitutive promoters include the 1'- or 2'-promoter derived from T-DNA of *Agrobacterium tumefaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al. *Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Riot* 208:551-565 (1989)), Gpc2 from maize (GenBank No. U45855, Manjunath et al., *Plant Mol. Biol.* 33:97-112 (1997)), other transcription initiation regions from various plant genes known to those of skill in the art. See also Holtorf *Plant Mol. Biol.* 29:637-646 (1995).

Inducible Promoters

Alternatively, a plant promoter may direct expression of the mutated PYR/PYL polynucleotide under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention can incorporate a drought-specific promoter such as a drought-inducible promoter of maize (e.g., the maize rab17 drought-inducible promoter (Vilardell et al. (1991) *Plant Mol. Biol.* 17:985-993; Vilardell et al. (1994) *Plant Mol. Biol.* 24:561-569)); or alternatively a cold, drought, and high salt inducible promoter from potato (Kirch (1997) *Plant Mol. Biol.* 33:897-909).

Alternatively, plant promoters which are inducible upon exposure to plant hormones, such as auxins, are used to express the mutated PYR/PYL polynucleotide. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10:955-966); the auxin-inducible parC promoter from tobacco (Sakai (1996) *Plant Cell Physiol.* 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902).

Plant promoters inducible upon exposure to chemicals reagents that may be applied to the plant, such as herbicides or antibiotics, are also useful for expressing the mutated PYR/PYL polynucleotide. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. A PYR/PYL coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Examples of useful inducible regulatory elements include copper-inducible regulatory elements (Mett et al., *Proc.*

Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Röder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible regulatory elements (Takahashi et al., Plant Physiol. 99:383-390 (1992); Yabe et al., Plant Cell Physiol. 35:1207-1219 (1994); Ueda et al., Mol. Gen. Genet. 250: 533-539 (1996)); and lac operon elements, which are used in combination with a constitutively expressed lac repressor to confer, for example, IPTG-inducible expression (Wilde et al., EMBO J. 11:1251-1259 (1992)). An inducible regulatory element useful in the transgenic plants of the invention also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)).

Tissue-Specific Promoters

Alternatively, the plant promoter may direct expression of the mutated PYR/PYL polynucleotide in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Other tissue-specific promoters include seed promoters. Suitable seed-specific promoters are derived from the following genes: MAC1 from maize (Sheridan (1996) Genetics 142:1009-1020); Cat3 from maize (GenBank No. L05934, Abler (1993) Plant Mol. Biol. 22:10131-1038); vivparous-1 from Arabidopsis (Genbank No. U93215); atmyc1 from Arabidopsis (Urao (1996) Plant Mol. Biol. 32:571-57; Conceicao (1994) Plant 5:493-505); napA from Brassica napus (GenBank No. J02798, Josefsson (1987) JBC 26:12196-1301); and the napin gene family from Brassica napus (Sjodahl (1995) Planta 197:264-271).

A variety of promoters specifically active in vegetative tissues, such as leaves, stems, roots and tubers, can also be used to express polynucleotides encoding mutated PYR/PYL receptor polypeptides. For example, promoters controlling patatin, the major storage protein of the potato tuber, can be used, see, e.g., Kim (1994) Plant Mol. Biol. 26:603-615; Martin (1997) Plant J. 11:53-62. The ORF13 promoter from Agrobacterium rhizogenes that exhibits high activity in roots can also be used (Hansen (1997) Mol. Gen. Genet. 254:337-343). Other useful vegetative tissue-specific promoters include: the tarin promoter of the gene encoding a globulin from a major taro (Colocasia esculenta L. Schott) corm protein family, tarin (Bezerra (1995) Plant Mol. Biol. 28:137-144); the curculin promoter active during taro corm development (de Castro (1992) Plant Cell 4:1549-1559) and the promoter for the tobacco root-specific gene TobRB7, whose expression is localized to root meristem and immature central cylinder regions (Yamamoto (1991) Plant Cell 3:371-382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) FEBS Lett. 415:91-95). A ribulose bisphosphate carboxylase promoters expressed almost exclusively in mesophyll cells in leaf blades and leaf sheaths at high levels, described by Matsuoka (1994) Plant J. 6:311-319, can be used. Another leaf-specific promoter is the light harvesting chlorophyll a/b binding protein gene promoter, see, e.g., Shiina (1997) Plant Physiol. 115:477-483; Casal (1998) Plant Physiol. 116:1533-1538. The Arabidopsis thaliana myb-related gene promoter (Atmyb5) described by Li (1996) FEBS Lett. 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) Plant J. 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) Cell 86:423-433; and, Long (1996) Nature 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) Plant Cell. 7:517-527). Also useful are kn1-related genes from maize and other species which show meristem-specific expression, see, e.g., Granger (1996) Plant Mol. Biol. 31:373-378; Kerstetter (1994) Plant Cell 6:1877-1887; Hake (1995) Philos. Trans. R. Soc. Lond. B. Biol. Sci. 350:45-51. For example, the Arabidopsis thaliana KNAT1 promoter (see, e.g., Lincoln (1994) Plant Cell 6:1859-1876) can be used.

One of skill in the art will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the mutated PYR/PYL polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

VII. Production of Transgenic Plants

As detailed herein, embodiments of the present invention provide for transgenic plants comprising recombinant expression cassettes for expressing a mutant PYR/PYL receptor protein as described herein in a plant. In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

A recombinant expression vector comprising a PYR/PYL coding sequence driven by a heterologous promoter may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of mutated PYR/PYL is encompassed by the invention, generally expression of a construct of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced abiotic stress resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplast Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer abiotic stress resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is selected from the group consisting of rice, maize, wheat, soybeans, cotton, canola, turfgrass, and alfalfa. In some embodiments, the plant is an ornamental plant. In some embodiments, the plant is a vegetable- or fruit-producing plant.

Those of skill in the art will recognize that a number of plant species can be used as models to predict the phenotypic effects of transgene expression in other plants. For example, it is well recognized that both tobacco (*Nicotiana*) and *Arabidopsis* plants are useful models of transgene expression, particularly in other dicots.

In some embodiments, the plants have enhanced sensitivity to certain chemical agonists compared to plants are otherwise identical except for expression of the mutated PYR/PYL receptor polypeptide. Sensitivity to agonists that agonize the PYR/PYL family of ABA receptors can be monitored by observing or measuring any phenotype mediated by ABA. Those of skill in the art will recognize that ABA is a well-studied plant hormone and that ABA mediates many changes in characteristics, any of which can be monitored to determine whether ABA sensitivity has been modulated. In some embodiments, modulated ABA sensitivity is manifested by altered timing of seed germination or altered stress (e.g., drought) tolerance.

Abiotic stress resistance can assayed according to any of a number of well-known techniques. For example, for drought tolerance, plants can be grown under conditions in which less than optimum water is provided to the plant. Drought resistance can be determined by any of a number of standard measures including turgor pressure, growth, yield, and the like.

As a further note, cells other than plant cells can comprise a polynucleotide encoding the mutated PYR/PYL polypeptides as described herein. In some embodiments, the cells comprise a heterologous expression cassette comprising the encoding polynucleotide operably linked to a promoter functional in the cell. The non-plant cells can be, for example (animal, e.g., mammalian), fungal, or bacterial cells. In some embodiments, the cells are responsive to the chemicals described herein, e.g., proposed in Liang et al., *Sci Signal.* 2011 Mar. 15; 4(164).

EXAMPLES

The following examples are offered to illustrate, but not to limit the claimed invention.

The plant hormone abscisic acid (ABA) regulates numerous physiological processes and plays a major role in abiotic stress responses and tolerance to water deficit (i.e. drought). ABA biosynthesis is stimulated by decreases in soil water content, which lead to elevated hormone levels that in turn stimulate large-scale alterations in transcript abundance, guard cell closure, increased production of protective osmolytes, and numerous other physiological changes (Cutler et al., 2010). A land-plant specific signaling pathway composed of receptors, phosphatases and kinases mediates ABA responses (Cutler et al., 2010). In this pathway, the phosphorylation status of three closely related ABA regulated SnRK2 protein kinases is tied to environmental stress. When activated, by phosphorylation on a critical activation loop near their ATP-binding site, these kinases phosphorylate downstream transcription factors, ion channels and most likely other proteins involved in ABA action (Weiner et al., 2010). Under ideal growth conditions the SnRK2s are continuously dephosphorylated and inactivated by a family of protein phosphatases (clade A PP2Cs), this results in nearly undetectable SnRK2 kinase activity in the absence of abiotic stress. ABA gains control over SnRK2 kinase activity via a family of soluble ABA receptors (PYR/PYL proteins) that inhibit PP2C activity in an ABA-dependent manner. When PP2C activity is inhibited by ABA-bound receptors, SnRK2s become highly active, most probably by virtue of their intrinsic ability to autoactivate via cis- and transautophosphorylation on their activation loops (Ng et al., 2011). Thus, ABA ultimately controls SnRK2 activity by receptor-mediated inhibition of PP2C activity.

The *Arabidopsis* genome encodes 13 ABA receptors that share sequence similarity to one another and Pyrabactin resistance 1 (PYR1), a founding member of the receptor family (Park et al., 2009). Biochemical studies have revealed that PYR1 and its two closest relatives, PYL1 and PYL2, (PYR1-like 1 and 2) are stable dimers in solution (Dupeux et al., 2011; Hao et al., 2011; Nishimura et al., 2009). X-ray crystallographic studies of the dimeric receptors alone and in complex with PP2Cs revealed that the homo-dimer interface of these receptors overlaps with the interface that binds and inhibits PP2C activity (Melcher et al., 2009; Miyazono et al., 2009; Yin et al., 2009). These structural observations initially implied that dimeric receptors require an ABA-meditated dimer-disruption step in order to inhibit PP2Cs and activate ABA signaling (Yin et al., 2009). Indeed, experimental data has demonstrated that ABA directly destabilizes the PYR1 dimer in vitro (Dupeux et al., 2011). The mechanism of dimer destabilization is not yet fully understood, but likely involves a conformational change of H60, a residue at the PYR1 homo-dimer interface that adopts a conformation unfavorable for dimer formation in the presence of ABA (Dupeux et al., 2011). H60 is adjacent to K59, an invariant residue that directly contacts ABA's carboxylate, and mutating K59 to any residue other than F or N abolishes ABA responsiveness (US20110271408). It has been proposed that dimer destabilization upon ligand binding is facilitated by a conformational change at H60 that is mediated by K59-ABA contacts (Dupeux et al., 2011). Dimer disruption is therefore a key aspect of dimeric ABA receptor activation.

It is well known that the exogenous application of ABA to plants reduces their water use, improves abiotic stress tolerance and can have a number of other useful effects. There has therefore been interest in using ABA, ABA analogs or synthetic ABA agonists to directly control stress tolerance. For example, ABA analogs with improved resistance to metabolic degradation have been disclosed (US20080200339; U.S. Pat. No. 6,004,905) and these compounds have more persistent effects than ABA itself. It has also been disclosed that natural ABA can be used for improving drought tolerance in horticultural species (US2008/0227645), as well several other uses. A number of synthetic compounds that activate ABA receptors (i.e. agonists) have also been described. The first synthetic ABA agonist identified was the naphthalene sulfonamide named pyrabactin (Park et al., 2009), which efficiently activates ABA signaling in seeds but has limited activity in vegetative tissues, where the most critical aspects of abiotic stress tolerance occur. Sulfonamides highly similar to pyrabactin have been disclosed as ABA agonists (US20130045952) and abiotic stress modulating compounds (US20110230350); and non-sulfonamide ABA agonists have also been described (US20130045952, US20110271408). There is therefore active interest in gaining chemical control over ABA receptor activity and the concomitant ability to modulate abiotic stress responses that such control affords.

Achieving control of a receptor with a synthetic compound typically involves a lengthy development process in which a molecule that interacts with a receptor is optimized by structure-activity-studies and/or other methods to maximize activity and potency at its target site. Optimized compounds are then subjected to further testing, during which their development can fail due to a multitude of undesirable properties that include toxicity, environmental persistence, poor solubility, rapid metabolism and lack of suitable uptake and/or in vivo mobility. Thus, a commercial agrichemical has a number of important properties in addition to potency at its target site. The process of imbuing the collection of necessary features into a single molecule remains a major challenge in agrichemical development.

An alternate path to gaining chemical control over a plant physiological process involves modifying a receptor so that it can be activated by an existing agrichemical. With such a system the receptor's activity can be controlled by an agrichemical ligand in transgenic plants that express the modified receptor. This approach has the intrinsic advantage that validated agrichemicals can be harnessed for selective control of receptor activity, which bypasses a development cycle that would otherwise be required to create agrichemicals active at the new target site. Another advantage relates to target-organism selectivity. In the case of compounds that modulate plant physiological processes, there is an inherent problem that compounds active at a conserved target sites often have activity on a broad range of non-target plant species. As a consequence, the compound may indiscriminately benefit both target and non-target organism (such as competing weeds), which may be undesirable. By expressing a modified receptor in a target plant, the beneficial effects of a compound can be restricted to the target organism. Thus, engineering a receptor to recognize an existing agrichemical ligand, as opposed to inventing a new agrichemical from scratch, allows for many challenging aspects of the agrichemical development process to be bypassed and affords a level of target-organism selectivity that is difficult to achieve otherwise.

We have recently disclosed modified ABA receptors that can be activated by non-natural agrichemical ligands (US20110271408). These receptor variants were identified by error-prone PCR-mutatageneses of receptors coupled with functional selections for receptor variants activated by specific agrichemical ligands. The selection experiments exploited the ability of the ligand-mediated receptor-PP2C interaction to be coupled to *S. cerevisiae* growth using a yeast two-hybrid system (Peterson et al., 2010). The mutations described primarily alter amino acids located in the receptor's ligand-binding pocket, which creates sensitivity to an agrichemical ligand while simultaneously eliminating intrinsic ABA sensitivity. This specific pairing of a defined ligand and mutant receptor allows for selective activation of the mutant receptor by the agrichemical ligand and frees the receptor from control by the endogenous ligand—such a system therefore enables orthogonal control of ABA receptor activity. Here we disclose methods for creating new orthogonal receptor systems. Orthogonal control over whole plant ABA responses, including robust drought stress tolerance, is demonstrated using the agrichemical mandipropamid in combination with transgenic plants expressing a mandipropamid responsive PYR1 variant.

Examples

1. An Improved Method for Discovering Ligand-Activated PYR1 Variants

An unexpected discovery in our initially disclosed selection experiments was that we independently isolated K59 substitution mutations in receptors that could be activated by a diversity of structurally unrelated ligands. As described in the background section, K59 contacts ABA's carboxylate and is adjacent to H60. Given the role of K59 and H60 in dimer destabilization, the K59 mutations may lower the threshold for ligand-induced dimer disruption, however their precise biochemical mechanism remains unknown. We reasoned that the process of identifying orthogonal receptor-ligand pairs could be improved by mutagenizing a PYR1 template that already harbors a K59 mutation, given the sensitizing effects of K59 substitutions. Additionally, the majority of mutations isolated in our selection experiments were located at ligand-contacting residues, which suggested that we might further improve the process by targeting mutagenesis to ligand-contacting residues. It is also understood that error-prone induced PCR mutations are strongly biased towards certain amino acid substitutions due to the structure of the genetic code. Consequently, any error-prone PCR mutagenesis is highly unlikely to sample all possible single amino acid substitutions in a target gene. Given these considerations, we reasoned that site-saturation mutagenesis of ligand contacting residues in a K59 mutant PYR1 backbone would improve the process of identifying orthogonal receptor-ligand pairs.

Site saturation mutagenesis involves directly constructing all 19 possible single amino acid substitution mutations at target residues of interest. To test our proposed method, we constructed a library of site-saturated mutants at 25 ligand-contacting residues in the PYR1$^{K59R}$ backbone. This particular K59 variant was selected because it was isolated in our earlier selection experiments (US20110271408); however, several other K59 mutations are beneficial for improving ligand sensitivity (all except K59I and K59P, as disclosed in US20110271408). Site-saturation libraries made with other K59 mutant backbones should also be beneficial for engineering orthogonal receptors. We define ligand-contacting residues as residues located within 5 Å of ABA, or 4 ABA-contacting water molecules, as deduced from inspecting publicly available PYR1-ABA-ABI1 X-ray crystallographic coordinates (the selection of these residues is described in (Mosquna et al., 2011)). The 25 ligand-contacting residues defined in PYR1 are: P55, F61, I62, V81, V83, L87, P88, A89, S92, E94, E141, F108, I110, H115, R116, L117, Y120, S122, M158, F159, A160, T162, V163, V164 and N167. A set of site-saturated mutations at these positions was previously constructed in a wild type PYR1 backbone as part of a larger effort focused on engineering constitutively active ABA variants (Mosquna et al., 2011). The PYR1 template mutagenized in those experiments was a pBD-PYR1 plasmid that encodes a GAL4-DNA binding domain fusion (BD) to PYR1; this plasmid can be directly utilized for assaying mutant receptor-PP2C interactions in an appropriate yeast strain co-transformed with pACT-PP2C, which express a GAL4 activation domain fusion (ACT) to a PP2C of interest.

We incorporated the K59R mutations in to each of the original PYR1 wild type backbone mutants using PCR-based mutagenesis to yield a collection of 475 PYR1$^{K59R}$ mutants. This was accomplished in two ways. Plasmids containing mutations in twenty-two of the sites targeted (all except P55, F61 and I62) were mutagenized using inverse PCR with two mutagenic primers (K59RB5 and K59RB3) oriented in opposite directions and directly flanking K59. After phosphorylating with polynucleotide kinase, these primers were used for PCR amplification of each of 418 pBD-PYR1 mutant templates. Three ligand-contacting residues (P55, F61 and I62) are too close to K59 to utilize this method. To introduce K59R into mutants at these sites, individual K59R mutagenic primers were designed complementary to each of the 57 remaining mutant templates. These primers were then utilized for inverse PCR mutagenesis, as described above. The linear PCR products generated using either method were ligated using T4 DNA ligase, digested with the restriction enzyme Dpn1 (to remove original template DNA) and transformed into competent E. coli cells. Transformed colonies were screened by PCR using K59R allele-specific primers to identify plasmids that had successfully incorporated the K59R mutation. K59R mutant plasmids were isolated and sequenced to verify that they contained both the introduced K59R mutation and the original ligand-site mutation. This mutagenesis effort created a set of 475 PYR1$^{K59R}$ variants containing all possible single amino acid substitutions at 25 ligand-contacting residues.

The set of 475 mutant plasmids were individually transformed into the Y190 yeast two hybrid reporter strain co-transformed with pACT-HAB1, as previously described (Park et al., 2009). The yeast strains generated were arrayed into 96-well plates yielding what we refer to as the "pocket library". The pocket library strains were spotted onto agar plates containing selective synthetic dextrose (minus Leu & Trp) medium that was supplemented with a single test compound at 100 µM. The pocket library strains were separately tested for responsiveness to the following compounds: dichlobenil, benzothiadiazole, mandipropamid, fludioxonil, and benoxacor. After incubating test plates at 30° C. for two days, colonies were chloroform lysed and stained to reveal β-galactosidase expression levels, using previously described methods (Park et al., 2009). Mutants displaying responsiveness to the test compound, if present, were identified by virtue of X-gal staining and then subjected to subsequent optimization efforts. Using this approach we identified mutations that conferred detectable sensitivity to the compounds tested (see entries labeled "Pocket Library Screens" in Table 1).

This screening approach yielded mutants at ligand contacting residues that alter sensitivity to specific ligands. We reasoned that receptor sensitivity could be improved by systematically constructing combinations of the best mutant variants identified in the first round of screening. To test this, we constructed mutant combinations using the strongest mutations identified for mandipropamid, benzothiadiazole, benoxacor or fludioxonil sensitivity. The mutations selected for combinatorial mutagenesis are listed in bold type in Table 1; The mutant combinations were constructed using the QuickChange Lightning Multi Site-Directed PCR Mutagenesis kit (Agilent, USA) using pBD-PYR1$^{K59R}$ template DNA and mutagenic primers, essentially as previously described (Mosquna et al., 2011). The mutant combinations were sequence validated, introduced into the pACT-HAB1 Y190 reporter strain and then tested for responsiveness to a range of compound concentrations (100, 50, 25, 10, 1, 0.2, 0.1 or 0 μM each test compound). These efforts yielded double mutant receptor variants with improved sensitivity for the 4 compound/receptor pairs examined (see entries labeled "Combinatorial Mutagenesis Screen I" in Table 1).

Example 2

Construction of Improved Mandipropamid Receptors

The preceding efforts identified PYR1$^{K59R,F108A,S122G}$, which is responsive to mandipropamid concentrations as low as 1 μM. We next attempted to improve the mandipropamid receptor by screening for additional pocket-located mutations that improve compound responsiveness. We subjected PYR1$^{K59R,F108A,S122G}$ to two separate mutagenesis experiments. We first examined the effects of adding single additional mutations at each of the other 23 ligand-contacting residues that are not altered in the PYR1$^{K59R,F108A,S122G}$ backbone, using NNK codon-randomization primers. Each NNK primer was used to generate a pool of PYR1$^{K59R,F108A,S122G}$ receptors containing additional mutations at a single ligand-contacting residue. DNA for this mutant pool was prepared and then transformed into a pACT-HAB1 MAV99 reporter strain, which allows URA3 based selection of active receptors (Peterson et al., 2010). The pooled yeast cells were plated on media containing 0.5 μM mandipropamid, a concentration too low to allow growth of a control MAV99 pACT-HAB1 reporter strain expressing pBD-PYR1$^{K59R,F108A,S122G}$. Positives were subsequently tested for growth on selective media in the absence of mandipropamid to establish if the variants possessed constitutive (i.e. not ligand dependent) interactions. Mutants enabling ligand-dependent interactions were sequenced and plasmid DNA for these mutants was isolated and introduced into Y190 pACT-HAB1 so that X-gal staining could be utilized to evaluate receptor sensitivity. This process was repeated for each of the remaining 22 NNK primers. These efforts yielded 10 mutations (V81C, V81I, V81T, V83L, L87A, F159L, F159M, F159V, A160V, V164I) that enhance the mandipropamid sensitivity of PYR1$^{K59R,F108A,S122G}$ (see entries labeled "NNK Mutagenesis Screen" in Table 1).

As a second approach, we used recombination-based mutagenesis to search for mutant combinations that enhance the sensitivity of PYR1$^{K59R,F108A,S122G}$ to mandipropamid. Nucleotide excision and exchange technology (NExT) (Müller et al., 2005) was used to mutagenize an equal amount of PYR1$^{K59R,F108A,S122G}$ template with an equal amount of template DNA that was made by pooling plasmid DNA from the NNK plasmid libraries made above for each of the 23 ligand-contacting residues in the PYR1$^{K59R,F108A,S122G}$ backbone. Thus, PYR1$^{K59R,F108A,S122G}$ was mutagenized with recombination-based mutagenesis using a library of pocket site mutations. An ~200,000 member library of mutagenized clones was generated and was transformed into the MAV99 pACT-HAB1 reporter strain. Selections were conducted on plates containing 0.5 μM mandipropamid and appropriate nutrients and amino acids. To establish if strain growth was ligand dependent, the positive clones were subsequently tested for growth on selective plates lacking mandipropamid. Next, plasmids were isolated from strains showing ligand-dependent growth and the mandipropamid sensitivity of mutant receptors characterized using X-gal staining (after transformation into the into the Y190 pACT-HAB1 reporter strain). These efforts led to the identification of a single new mutation, Y58H, that improves the mandipropamid sensitivity of the PYR1$^{K59R,F108A,S122G}$ receptor (see entries labeled "Recombination-based Mutagenesis Screen" in Table 1). Interestingly, Y58 was not targeted in the pooled NNK template utilized in the recombination reactions; this mutation was therefore a spontaneous mutant that arose during the mutagenesis process. The side chain of Y58 projects into PYR1's ligand binding pocket but is not within the 5 Å cut-off we initially employed for targeting ligand-binding residues in our site-saturation mutagenesis; extending the pocket library to include all residues that project into PYR1's ligand binding pocket should therefore improve the receptor discovery process.

Both of the above optimization experiments led to the identification of the following mutations that, when introduced one at a time, enhance the mandipropamid sensitivity of PYR1$^{K59R,F108A,S122G}$: Y58H, V81C, V81I, V81T, V83L, L87A, F159L, F159M, F159V, A160V and V164I. Given that these each enhance sensitivity on their own, we tested if combinations of these mutations might generate more sensitive receptors. Mutagenic primers for each of the mutations were designed and used simultaneously with the QuickChange Lightning Multi Site-Directed Mutagenesis kit (Agilent, USA) with PYR1$^{K59R,F108A,S122G}$ template DNA. Individual clones were sequenced to identify bona fide combination mutants, which were transformed into the Y190 pACT-HAB1 yeast strain and assayed for mandipropamid sensitivity. These efforts led to the identification of several improved receptors ("Combinatorial Mutagenesis Screen II", Table 1), including PYR1$^{Y58H,K59R,V81I,F108A,S122G,F159L}$, a hextuple mutant that we have named PYR1$^{MANDI}$. Yeast reporter strains expressing this mutant are responsive to mandipropamid concentrations as low as 2 nM (Table 1). Thus, the 5-step mutagenesis protocol we followed led to the construction of a mandipropamid responsive receptor with nanomolar sensitivity.

Example 3

PYR1$^{MANDI}$ Potently Inhibits PP2C Activity in a Mandipropamid-Selective Manner One possibility in any functional screen conducted in a heterologous organism such as *S. cerevisiae* is that mutants identified may only work in the context of the heterologous expression system. We therefore examined whether recombinant PYR1$^{K59R,F108A,S122G}$ and PYR1$^{MANDI}$ proteins inhibit PP2C activity in vitro, as is well documented for wild type PYR1 in response to ABA (Park et al., 2009). Both receptors were cloned into pET28 to generate 6×-His (SEQ ID NO:109) tagged receptors. These were expressed in BL21[DE3]pLysS *E. coli* host cells at 18° C. overnight. 6×-His-fusion proteins were purified from sonicated lysates using Ni-NTA agarose (Qiagen, USA), according to the manufacturer's instructions. For PP2C assays, recombinant GST-HAB1 and GST-ABI2 were expressed and purified as described previously (Park et al., 2009) and PP2C activity assayed conducted using the colorimetric phosphatase substrate para-nitrophenyl phosphate (pNPP) as previously described (Park et al., 2009). PP2C assays were conducted using 600 nM of PP2C and 1200 nM recombinant receptors. We note that the low sensitivity of pNPP based assays necessitates a higher than ideal concentration of PP2C; as a result, accurate $IC_{50}$ values can be not be inferred from the data shown, however the data demonstrate saturable inhibition of HAB1 and ABI2 PP2C activity by mandipropamid in the presence of PYR1$^{MANDI}$ (FIG. 1A, bottom lines) and PYR1$^{K59R,F108A,S122G}$(FIG. 1A, top lines). We note that these mutant receptors cannot respond to ABA due to the K59R mutation they contain, which abolishes ABA responsiveness.

We next characterized the effects of recombinant PYR1$^{MANDI}$ on PP2C activity using the fluorogenic substrate 4-methylumbelliferyl-phosphate. Recombinant receptor and PP2C proteins were prepared as described above and used to examine PP2C inactivation in response to mandipropamid or ABA. Enzyme inhibition assays were conducted using the following assay conditions: 100 nM 6×-His-PYR1$^{MANDI}$, 50 nM GST-PP2C, 100 mM Tris-OAc (pH 7.9), 100 mM NaCl, 1 mM MnCl$_2$, 1% β-mercaptoethanol. The 2:1 ratio of receptor to PP2C concentration was based on titration experiments, which showed that maximal inhibition of HAB1 PP2C activity (at saturating ABA concentrations, 10 µM) required a 2-fold excess of receptor to PP2C. This suggests that a sub-population of the recombinant receptor is likely inactive. Thus, under these reaction conditions the concentrations of active receptors and PP2Cs is approximately equimolar, although it may lower than 50 nM given that we do not know the precise concentration of active PP2C. The three ABA-regulated clade A PP2Cs, GST-HAB1, GST-ABI1 and GST-ABI2 were each tested under the same enzyme conditions in separate reactions. The assays were conducted at a variety of mandipropamid or ABA concentrations so that IC$_{50}$ values could be determined. As shown in FIG. 1B, these assays reveal IC$_{50}$ values of 32.2, 26.8 and 75.5 nM for mandipropamid mediated inhibition of HAB1, ABI1 and ABI2. Thus, the PYR1$^{MANDI}$ receptor is highly sensitive to activation by mandipropamid and interacts with multiple clade A PP2Cs in response to mandipropamid. This high level of sensitivity is consistent with the yeast two hybrid results described above in which a detectable interaction between PYR1$^{MANDI}$ and HAB1 could be observed at concentrations as low as 2 nM (see Table 1). We note that the yeast two hybrid reporter systems requires only a small percentage of PYR1$^{MANDI}$ receptors to bind HAB1 for an interaction signal and is therefore a potentially more sensitive indicator than in vitro assays. Additionally, the data indicated that the receptors are not appreciably activated by ABA. Thus these in vitro assays confirm that PYR1$^{MANDI}$ is selectively activated by mandipropamid. Collectively the in vitro and yeast two hybrid based assays show that PYR1$^{MANDI}$ potently inhibits PP2C activity in a mandipropamid-selective manner.

Example 4

PYR1$^{MANDI}$ Binds HAB1 in Response to Mandipropamid in Planta

Figure 2:
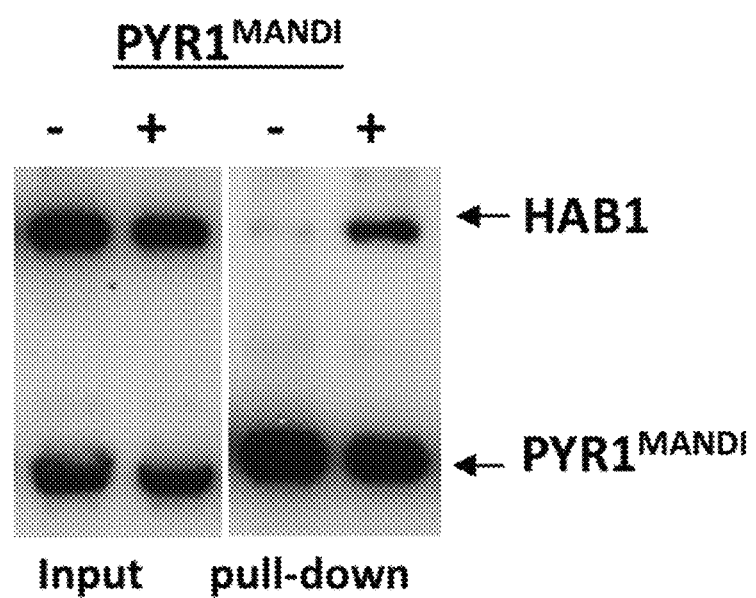
FIG. 2 shows protein expression data as discussed further in the Examples.
Figure 3:
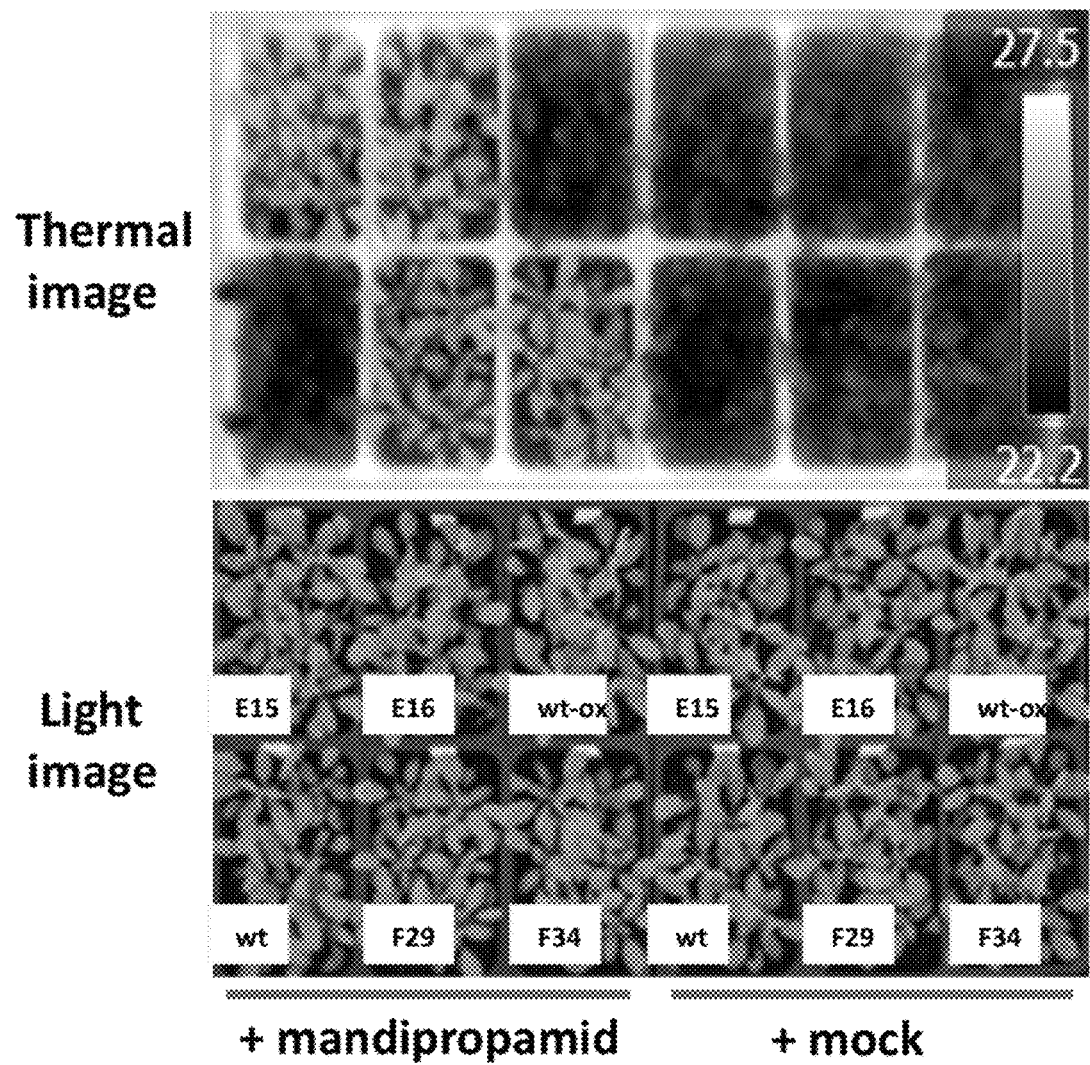
FIG. 3 shows thermal imaging results of mandipropamid treatment of PYR1$^{mandi}$ transgenic plants.
Figure 4:
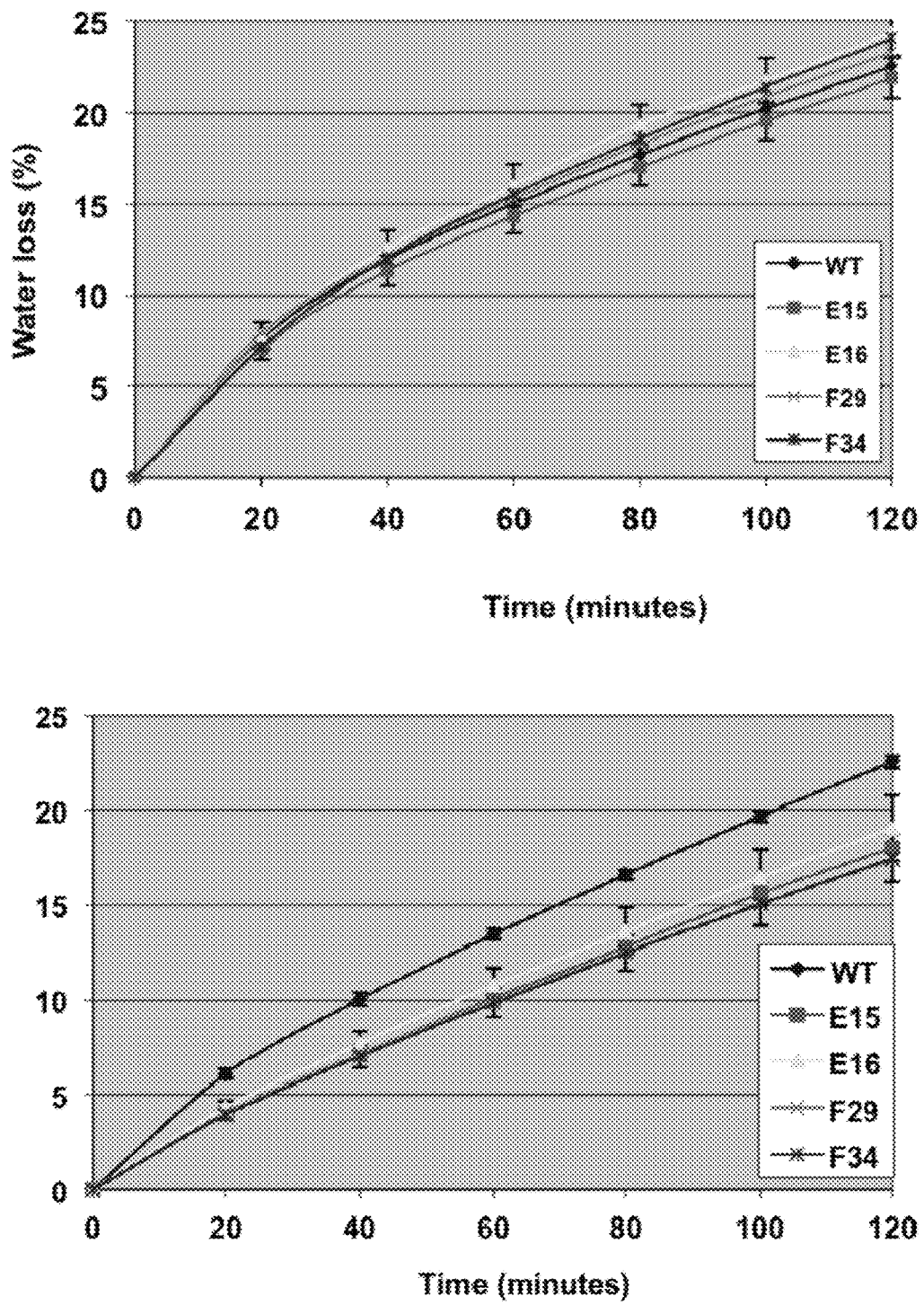
FIG. 4 summarizes data for water loss vs. time for PYR1$^{mandi}$ transgenic plants.
Figure 5:
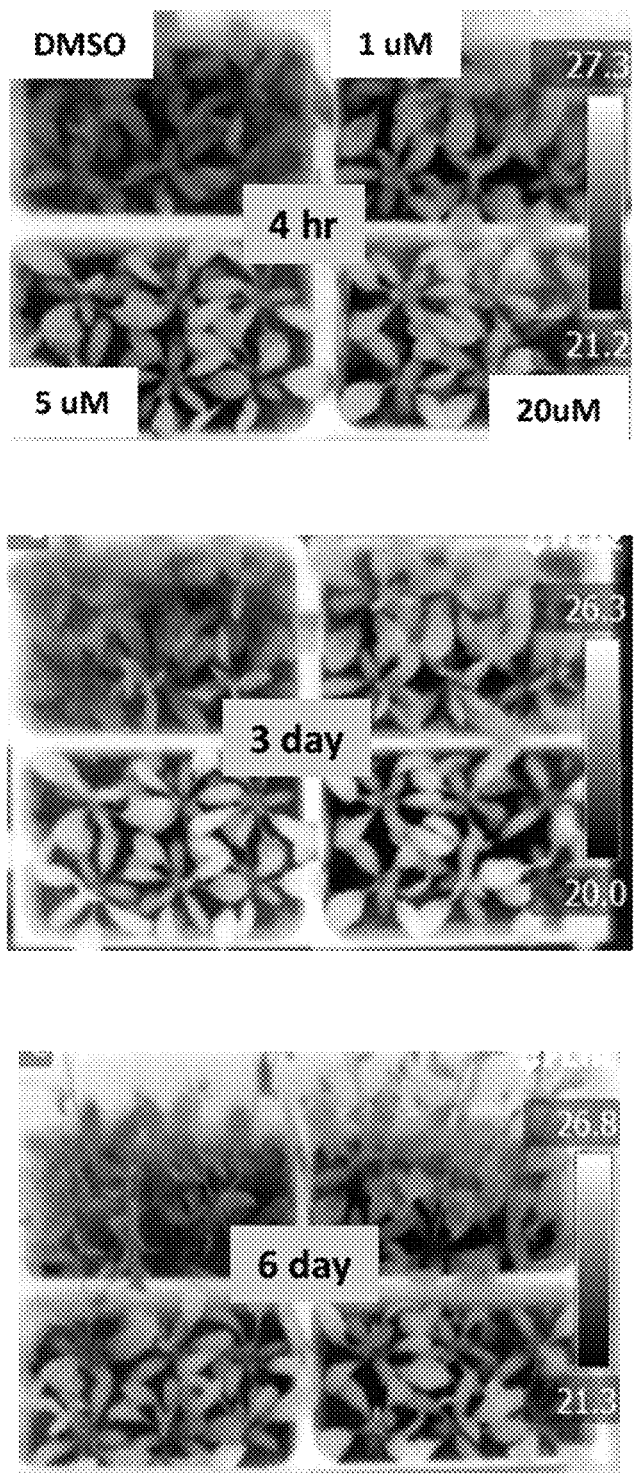
FIG. 5 shows that the effects of mandipropamid on PYR1$^{mandi}$ transgenic plants lasted at least 6 days.
Figure 6:
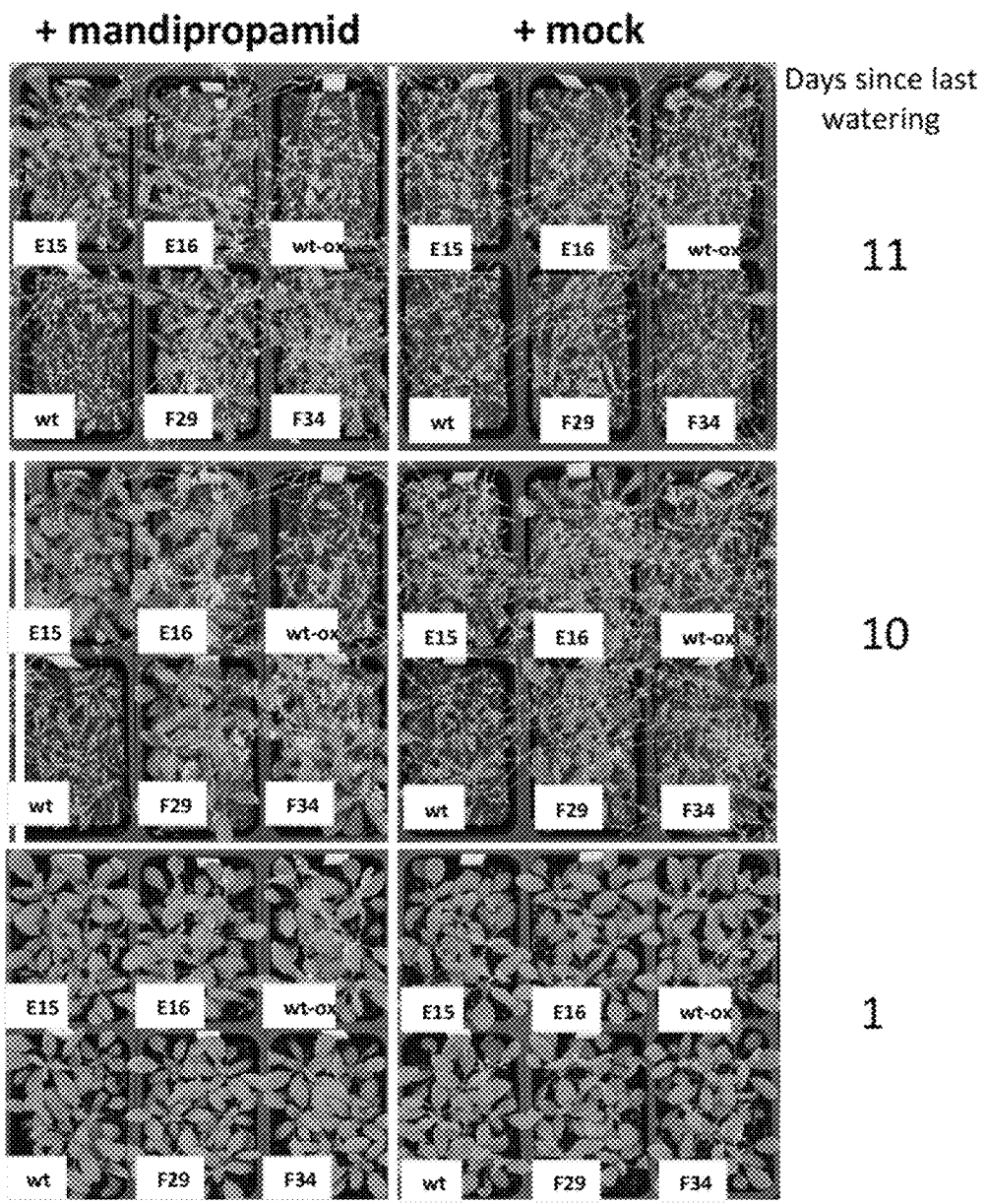
FIG. 6 shows effects of progressive water loss on control and PYR1$^{mandi}$ transgenic plants.

It has previously been demonstrated that the ABA-modulated interaction of PYR1 with PP2Cs can be monitored by co-precipitation experiments using proteins transiently co-expressed in Nicotiana benthamiana (Park et al., 2009). We therefore investigated if the mandipropamid promoted interaction between PYR1$^{MANDI}$ and the PP2C HAB1 could be observed using similar experiments. To conduct these experiments PYR1$^{MANDI}$ was cloned as a 6×-His-GFP fusion protein in the vector pEGAD (Cutler et al., 2000). HAB1 was cloned as a GFP fusion protein in the vector pEGAD. Both constructs were transformed into Agrobacterium tumefaciens (GV3101) and utilized in transient expression experiments. The Agrobacterium strains harboring the receptor, PP2C and the silencing suppressor p19 were mixed together in ratios corresponding to 0.1, 1.0 and 0.5 final OD$_{600}$ units respectively. The mixture was infiltrated into two separate N. benthamiana leaves and 2 days later the leaves were treated with either 50 µM mandipropamid or mock solutions made in water containing 0.02% Silwet L-77. 20 hours later the leaves were homogenized in liquid nitrogen, re-suspended in an extraction buffer composed of 1×TBS, 0.1% NP-40, 1 mM DTT, 10% glycerol, and 1× plant protease inhibitor cocktail (Sigma, USA) and clarified by centrifugation. 25 mg of PrepEase nickel-NTA agarose (USB, USA) was added to the extracts to isolate 6×-HIS tagged PYR1$^{MANDI}$ receptors and any associated proteins. The resin was washed 3 times; bound proteins were eluted in SDS-PAGE loading buffer, separated by SDS-PAGE and then electroblotted onto nitrocellulose membranes. Both PYR1$^{MANDI}$ and HAB1 were expressed as GFP fusion proteins and could therefore be detected with an anti-GFP antibody. The blots were probed with an anti-GFP monoclonal primary antibody and detected using an anti-mouse IgG-HP sheep secondary antibody using ECL (Amersham, USA) development. As shown in FIG. 2, treatment of N. benthamiana leaves co-expressing 6×-His-GFP-PYR1$^{MANDI}$ and GFP-HAB1 leads to a mandipropamid-dependent physical interaction between the two proteins, which demonstrates that the receptor is functional in planta.

Example 5

PYR1$^{MANDI}$ Inhibits Seed Germination in Response to Mandipropamid

We generated a series of transgenic plants expressing PYR1$^{MANDI}$ under the control of either the cauliflower mosaic virus 35S or Arabidopsis Rubisco small subunit 3B promoters (RBCS). These were generated for the purpose of examining the physiological efficacy of the PYR1$^{MANDI}$-mandipropamid system for regulating ABA responses in planta. The PYR1$^{MANDI}$ coding sequence was PCR amplified from pBD-PYR1$^{MANDI}$ template and cloned into the plant transformation vector pEGAD under control of the 35S promoter. For the RBCS driven construct, the 35S promoter in pEGAD was replaced with the RBCS promoter, which was amplified from Arabidopsis genomic DNA by PCR; the pEGAD vector contains a glufosinate resistance gene and allows selection of transgenics in soil using commercially available formulations of glufosinate. These two constructs, p35S::PYR1$^{MANDI}$ and pRBCS::PYR1$^{MANDI}$, were introduced into Agrobacterium tumefacians GV3101 and then used to transform Arabidopsis using the floral dip method (Clough and Bent, 1998) and the resultant seed germinated in soil and treated with glufosinate to identify transformed plants. Seed from approximately 15-16 transgenic plants were harvested individually and then characterized. It is well known that ABA inhibits seed germination. To investigate if the PYR1$^{MANDI}$ receptors could activate ABA signaling in response to mandipropamid in seeds, we germinated seeds from wild type and the transgenic plants on growth medium containing 1 µM mandipropamid. As shown in Table 2, the germination of 5 of the 15 35S::PYR1$^{MANDI}$ expressing transgenic plants were inhibited by mandipropamid and 7 of the 16 RBCS:PYR1$^{MANDI}$ expressing transgenic plants were inhibited by mandipropamid. Therefore, approximately half of the transgenic plants made using either promoter respond to mandipropamid in a germination assay, which indicates that PYR1$^{MANDI}$ is capable of activating ABA signaling in seeds in response to mandipropamid. It is understood that independent transgenic plants containing the same DNA construct will display variation in expression levels of the transgene due to position and other effects. It is therefore likely that some of the transgenic plants lack sufficient receptor expression to elicit ABA signaling in response to mandipropamid. Thus, PYR1$^{MANDI}$ can activate ABA signaling seeds.

Example 6

PYR1$^{MANDI}$ Elicits Guard Cell Closure in Response to Mandipropamid

Figure 7:
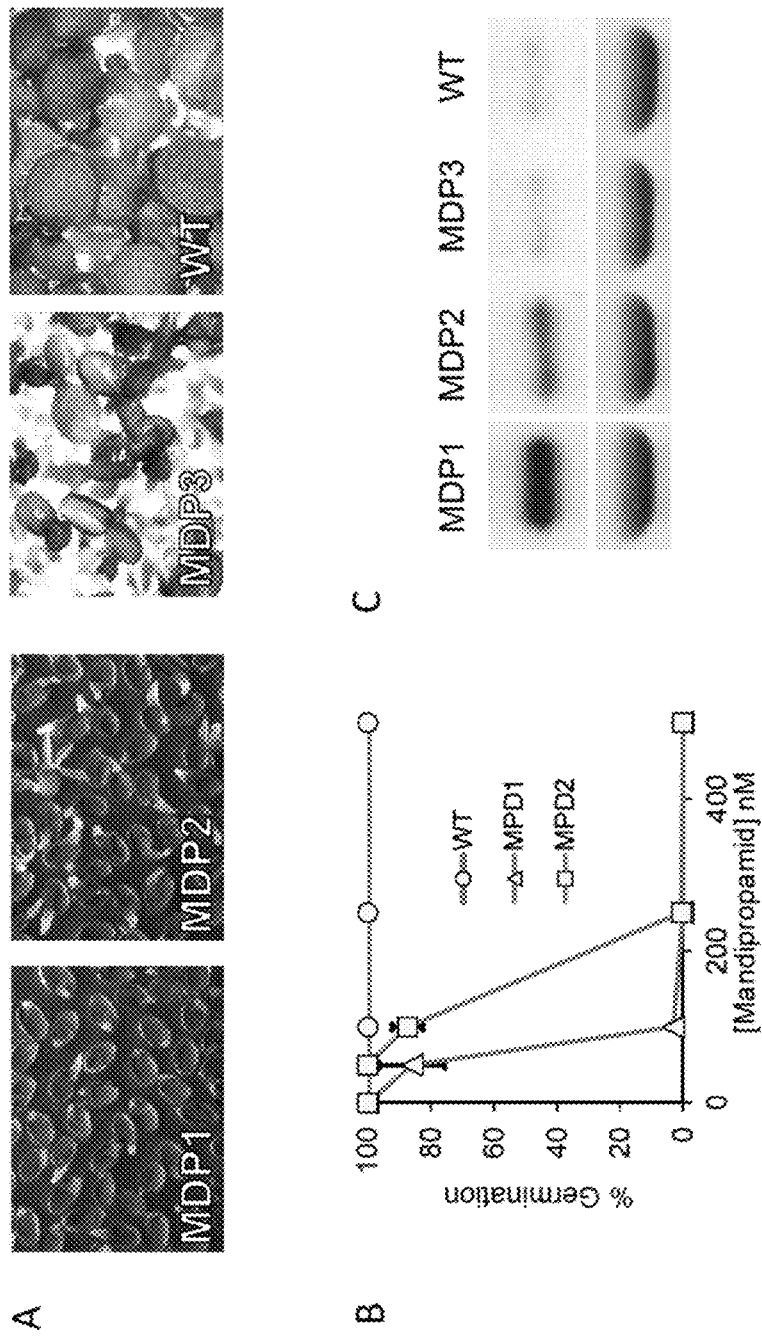
FIG. 7A shows results of a seed germination assay.
FIG. 7B shows a summary of dose-response of seed germination in response to mandipropamid.
FIG. 7C shows a western blot indicating PYR1 PYR1$^{mandi}$ protein levels.

The ability of mandipropamid to inhibit germination in PYR1$^{MANDI}$ expressing transgenic plants indicates that ABA signaling can be activated with this ligand-receptor pair. To investigate if the system is sufficient to control ABA responses in vegetative tissues, we generated homozygous transgenic lines for two 35S-driven lines (E15 and E16) and 2 RBCS-driven lines (F29 and F34). These materials were grown along side wild type plants and a previously constructed 35S::GFP-PYR1 over expression line (Park et al., 2009). These plants were grown until three weeks old and then treated with a solution containing either 2 μM mandipropamid and 0.02% Silwet or a mock treatment containing 0.02% Silwet and the mandipropamid carrier solvent (DMSO). 24 hours after treatment, the leaf temperatures were examined using a thermal imaging camera. It is well known that ABA-induced guard cell closure reduces transpiration, which leads to increases in leaf temperatures. It has been estimated that a 1° C. increase in leaf temperature correlates with a decrease in transpiration rates by approximately 50% (Sirault et al., 2009). Since guard cell aperture is the primary determinant of transpiration rates, thermal imaging is a useful way to indirectly infer relative transpiration rates and guard cell aperture at the whole plant level. As is shown in FIG. 3, mandipropamid treatment of homozygous PYR1$^{MANDI}$ expressing transgenic plants leads to large changes in leaf temperature (~2° C. increase) within 24 hours of treatment. This effect of mandipropamid is not observed in wild type or 35S::GFP-PYR1 expressing transgenic plants, indicating that the temperature effect induced by mandipropamid is mediated by the PYR1$^{MANDI}$ transgene.

As another measure of guard cell physiology, we measured rates of water loss in transgenic and control plants exposed to mock or mandipropamid treatments. It is well known that ABA treatments reduce leaf water loss via guard cell closure. 3 week-old homozygous transgenic plants (E15, E16, F29 and F34) and control wild type plants were treated with 2 μM mandipropamid or mock solutions (with 0.02% Silwet as described above). After 24 hours, whole rosettes were detached and their masses monitored over time. Experiments were conducted in triplicate and the means and standard deviations of the measurements are shown in FIG. 4. Mandipropamid, but not mock, treatments lower water loss PYR1$^{MANDI}$ expressing transgenic plants but not wild type plants. These experiments, together with the thermal imaging experiments, indicate that mandipropamid can reduce guard cell aperture and reduce transpiration rates in PYR1$^{MANDI}$ expressing transgenic plants, just as ABA is well known to do to wild type plants.

Example 7

PYR1$^{MANDI}$ Responses are Very Persistent

Treatment of plants with abscisic acid leads to the induction of CYP707A cytochrome P450s, which hydroxylate ABA at its 8' methyl group. This ultimately leads to the spontaneous formation of phaseic acid, an inactive ABA metabolite (Nambara and Marion-Poll, 2005). Thus, ABA applications lose effect over time due to metabolic inactivation. Given that mandipropamid is a non-native molecule, it is likely not a degraded by the CYP707A enzyme system. We therefore investigated the persistence of the increased leaf temperature observed in mandipropamid treated PYR1$^{MANDI}$ transgenic plants. Plants were treated with mock, 1, 5 or 20 μM mandipropamid and then analyzed by thermography at 4 hours, 3 and 6 days after treatment. As shown in FIG. 5, the effects of 5 μM and 20 μM mandipropamid persisted for at least 6 days. Additionally, control and 1 μM treated plants flowered during the experiment while flowering was prevented in the 5 μM and 20 μM treated mandipropamid plants. These data show that the effects of mandipropamid treatments are persistent and dose dependent. They also show that the effects occur rapidly since increased leaf temperature was observed within 4 hours of mandipropamid treatment.

Example 8

PYR1$^{MANDI}$ Enables Orthogonal Control of Drought Stress Tolerance

Treatment of plants with ABA delays water loss and additionally improves the ability of plants to recover from drought. We therefore examined the behavior of wild type, 35S::GFP-PYR and 4 homozygous PYR1$^{MANDI}$ expressing transgenic plants (E15, E16, F29 and F34) during a progressive water loss regime. Six sets of plants were grown, three for control mock treatments and three for experimental treatments; Figure six shows data for one of the three replicates, similar behaviors of transgenic plants and controls were observed in all three replicates. Plants were grown for three weeks in pots containing the same mass of soil and receiving the same amount of water at each watering. At three weeks after germination, regular watering of the plants was ceased and plants were treated with mock or 2 μM mandipropamid. These treatments were repeated 4 days later. Plants were photographed at 1, 10 and 11 days after initiation of water deprivation. As is evident from FIG. 6, by day 10 mock treated plants display evidence of water stress as indicated by collapsed leaves, by day 11 all mock treated plants have experienced severe desiccation. Both PYR1$^{MANDI}$ and 35S::GFP-PYR1 transgenic plants have increased drought tolerance relative to wild type at day 10; this is likely a PYR1 overexpression phenotype, since overexpression of PYR/PYL genes have previously been shown to improve drought tolerance (Santiago et al., 2009). This is also observed for wild type and 35S::GFP-PYR plants treated with mandipropamid at day 10. However, the data demonstrate that mandipropamid treated PYR1$^{MANDI}$ transgenic plants have not desiccated at day 11. This is in contrast to wild type and 35S::GFP-PYR1 control plants treated with mandipropamid and all mock treated lines. Thus, mandipropamid is able to improve drought stress tolerance in PYR1$^{MANDI}$ expressing transgenic plants. The beneficial effects of mandipropamid are restricted to PYR1$^{MANDI}$ expressing transgenic plants. These data indicate that the PYR1$^{MANDI}$/mandipropamid system enables orthogonal control of drought stress tolerance.

Example 9

PYR1$^{MANDI}$ Protein Expression Levels Control Mandipropamid Sensitivity in Planta.

To further characterize the physiological effects of the PYR1$^{MANDI}$/mandipropamid interaction, we characterized three independently generated transgenic *Arabidopsis* lines in more detail. These lines, initially named E9, E16 and E31 are henceforth referred to as MPD1, MPD2 and MPD3. Each of these lines is homozygous for a single 35S::PYR1$^{MANDI}$ insertion site and is the result of independent transformation events. We first used germination assays to characterize the relative mandipropamid sensitivity of these lines. Seeds for the transgenics and wild type control were surface sterilized with bleach and then stratified for 4 days at 4° C. on 0.7% agar petri plates containing ½ MS salts and 0.5% sucrose in addition to either 250 nM mandipropamid or a mock treatment of 0.1% DMSO (the carrier solvent). After stratification, the plates were transferred to a growth chamber operating on a 16-hour day length cycle. Seed germination was scored 3 days post-stratification. As shown in FIG. 7A, the relative sensitivity of the lines to mandipropamid is MDP1>MDP2>MDP3. MDP1 seed show near complete germination inhibition by 250 nM mandipropamid and MDP3 displays minimal sensitivity during germination, but weak growth reduction after germination growth, which indicates that it is somewhat sensitive to mandipropamid. To more definitively assess the relative sensitivity of the MDP1 and MDP2 lines to mandipropamid, we conducted germination dose-response experiments (using the same procedure described above) and confirmed that the MDP1 line is more sensitive to mandipropamid than MDP2 (FIG. 7B).

A possible explanation for the differing sensitivities between the MDP1 and MDP2 lines is that the MDP1 line has a higher level of PYR1$^{MANDI}$ expression. To investigate this, western blot analyses were conducted using a previously described anti-PYR1 antibody (Nishimura et al. 2010). Total proteins were extracted from 7-day old transgenic and wild type Columbia control seedlings in TBS buffer (10 mM Tris-HCl pH=7.4 150 mM NaCl) supplemented with 1% protease inhibitor cocktail (Sigma). Each protein sample (25 µg protein) was separated using a 10% SDS-PAGE gel, transferred to nitrocellulose by electrotransfer and then probed with anti-PYR1 anti-sera and detected using ECL (Amersham). As shown in FIG. 7C, the levels of PYR1$^{MANDI}$ protein correlate with mandipropamid sensitivity (levels of protein detected follow the order MDP1>MDP2>MDP3). These data suggest that the level of receptor protein is an important determinant of mandipropamid sensitivity. This is consistent with the mechanism of action of PYR/PYL receptors, which are competitive inhibitors of PP2C activity when activated by ligands. These, data show that PYR1$^{MANDI}$ protein expression levels control mandipropamid sensitivity in planta.

Example 9

Mandipropamid Inhibits Root Growth in Transgenic *Arabidopsis* Plants Expressing PYR1$^{MANDI}$.

Figure 8:
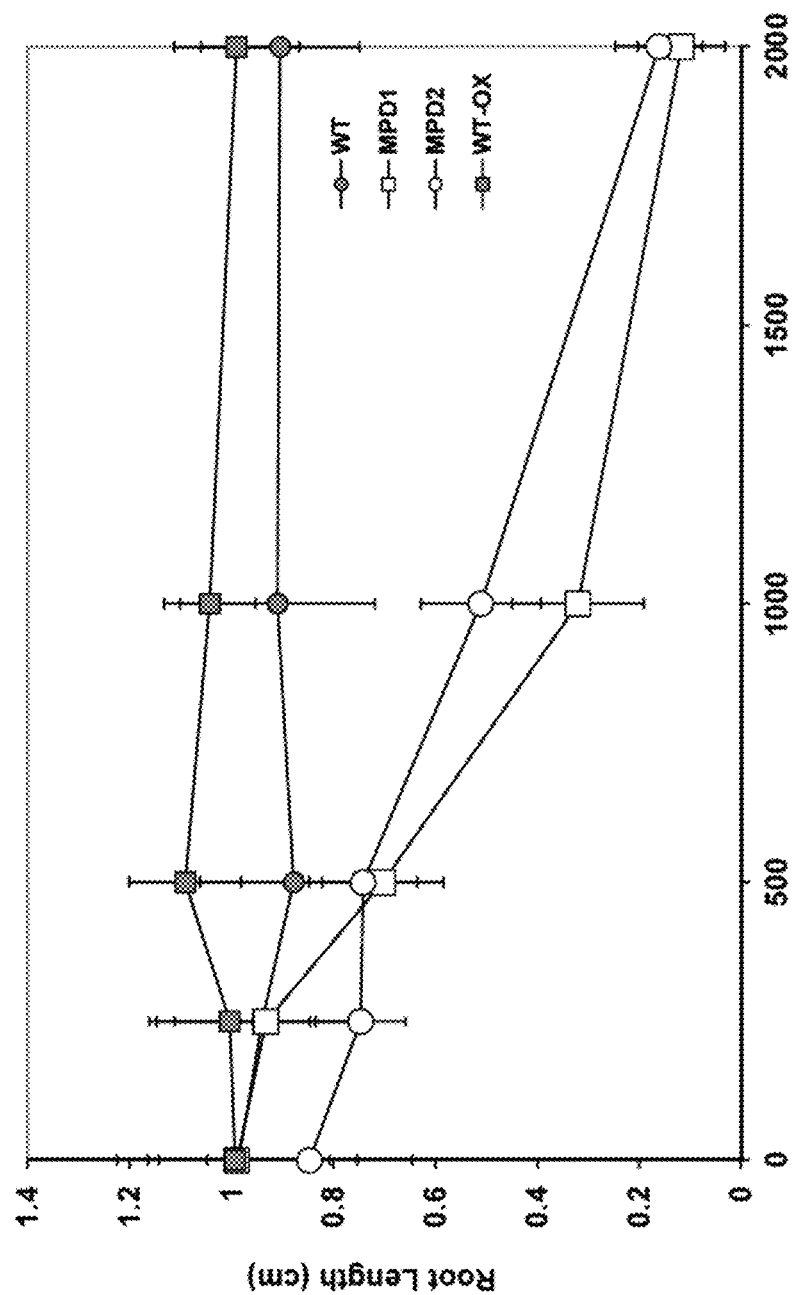
FIG. 8 shows results of a root growth inhibition assay.

Given the relatively high mandipropamid sensitivity of the MDP1 and MDP2 transgenic lines, these lines were subjected to further physiological characterization. One of ABA's physiological effects is to inhibit root growth. Mandipropamid should therefore inhibit root growth in the MDP1 and MDP2 transgenic lines, but not wild type, if it is successfully activating this ABA response. To test this, seeds of the wild type, PYR1-OX, MDP1 and MDP2 genotypes were surface sterilized in bleach and plated on to 0.7% agar petri plates containing ½ MS salts and 0.5% sucrose. After 4 days of stratification at 4° C., the plates were transferred to a growth chamber operating on a 16-hour day length cycle and allowed to germinate for 24 hours and then transferred to petri plates (0.7% agar containing ½ MS salts and 0.5% sucrose) supplemented with differing concentrations of mandipropamid. These plates were then grown vertically in a growth chamber operating on a 16-hour day length cycle. The amount of root growth after transfer was measured 72-hours later after transfer. As shown in FIG. 8, the root growth of MDP1 and MDP2 transgenic genotypes is inhibited by mandipropamid but the wild type and PYR1-OX genotypes show negligible inhibition by mandipropamid. These results provide further evidence that expression the PYR1$^{MANDI}$ receptor enables activation of ABA signaling in response to mandipropamid in planta.

Example 10

Mandipropamid Increases RAB18 and RD29B Transcript Levels in Transgenic *Arabidopsis* Plants Expressing PYR1$^{MANDI}$.

One of ABA's major effects is to regulate gene expression. We therefore examined the effects of ABA and mandipropamid on gene expression in wild type, PYR-OX, MDP1 and MPD2 transgenic plants. Seed of the wild type or transgenic lines were surface sterilized, stratified for 4 days at 4° C. and then grown for 10 days at room temperature under continuous illumination in a liquid culture consisting of 0.5×MS salts and 0.5% sucrose and grown with continuous shaking to provide aeration. After 10 days, the culture solutions were adjusted to contain 50 µM ABA, 2 µM mandipropamid, or a mock treatment. After 8 hours exposure to the test compounds RNA was isolated using RNAEasy™ Plant RNA isolation kit (Qiagen, USA) and treated with DNAse. The purified RNA was utilized in qRT-PCR reactions using primers for the ABA-regulated genes RD29B or RAB18. Biological triplicate and triple technical replicate measurements were conducted. To perform qRT-PCR analyses, cDNA was generated from 5 µg of total RNA using superscript reverse transcriptase III (Invitrogen, USA), in reaction mixture containing a oligo-dT$_{20}$ (SEQ ID NO:110) and a ribosomal RNA primer. Real-time quantitative PCR analysis was performed by ΔCt method of relative quantification. PCR mixtures contained cDNA, Maxima® SYBR green/Fluorescein qPCR master mix (Fermentas, USA) and 330 nM of each gene-specific primer. RT-PCRs were conducted using a BioRad CFX96 Real-Time PCR System and the data were processed using the BioRad CFX Manager software (BioRad, USA). PCRs were performed under the following cycling conditions: 3 min at 95° C., followed by 40 cycles of 10 sec at 95° C., 10 sec at 55° C. and 30 sec at 72° C. in 96-well optical reaction plates (BioRad, USA). The specificity of amplicons was verified by melting curve (disassociation) analysis (60-95° C.) after 40 cycles. Input cDNA was normalized using an internal control gene, PEX4 (AT5G25760).

Figure 9:
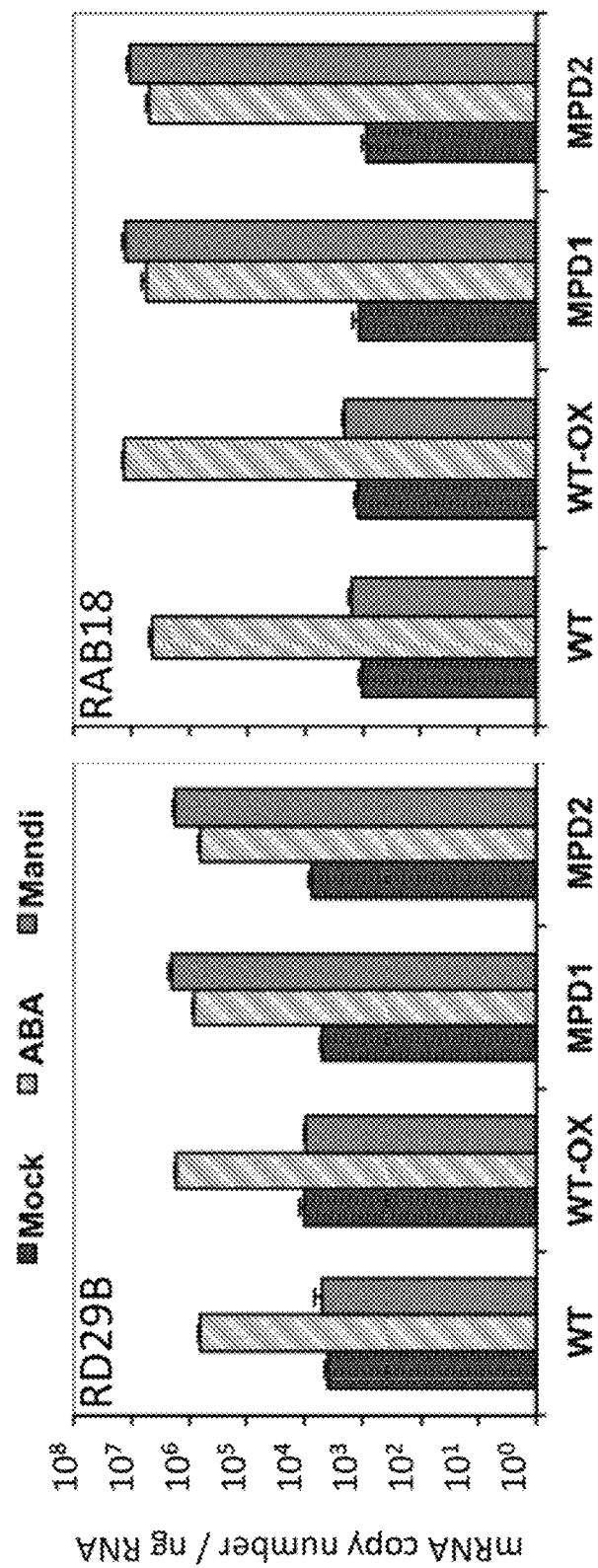
FIG. 9 shows results of gene expression levels of genes responsive to ABA in 35S::PYR1$^{MANDI}$ transgenic plants.

The data from these gene expression experiments are shown in FIG. 9. These experiments show that mandipropamid induces high-level transcription of RD29B and RAB18 in the PYR1$^{MANDI}$ expressing transgenic plans MDP1 and MDP2, but it does not do so in either wild type or PYR1-OX controls. Thus, consistent with other observations, mandipropamid is able to regulate ABA responses in transgenic *Arabidopsis* plants expressing PYR1$^{MANDI}$, as measured using RAB18 and RD29B transcript levels. Additionally, these data show that the ability of endogenous ABA to regulate RD29B and RAB18 gene induction is not compromised by expression of the PYR1$^{MANDI}$ protein. Furthermore, the levels of RAB18 and RD29 induced by ABA in PYR1-OX lines are higher than the levels induced by the same concentration of ABA in wild type plants. Since these lines over-express PYR1, these observations, together with those reported in Example 8, are consistent with the hypothesis that that PYR1 protein levels control the magnitude of response to ABA (or mandipropamid in the case of PYR1$^{MANDI}$).

Example 11

Mandipropamid Induces a Genome Wide ABA-Like Transcription Response in Transgenic *Arabidopsis* Plants Expressing PYR1$^{MANDI}$.

The experiments of Example 10 show that mandipropamid can modulate ABA responsive gene expression in 35::PYR1$^{MANDI}$ transgenic lines, however they do not provide a genome-wide portrait of how closely it mimics ABA's effects. We therefore examined the effects of ABA and mandipropamid on gene expression in wild type and MDP1 transgenic plants using RNASeq experiments. The total RNA obtained in Example 10 was prepared for RNASeq using the NEBNext platform, which consists of a Poly(A) mRNA Magnetic Isolation Module, NEBNext Multiplex Oligos for Illumina, and NEBNext Ultra RNA Library Prep Kit for Illumina, New England BioLabs. poly(A) mRNA was isolated using NEBNext oligo d(T)$_{25}$ (SEQ ID NO:111) magnetic beads and 5 µg total RNA input, as described by the manufacturer. mRNA was eluted using the kit's first strand synthesis reaction buffer and hybridized to a random primer mix by incubating the sample at 94° C. for 15 minutes followed by cooling. First strand cDNA was synthesized using ProtoScript II Reverse transcriptase and subsequently second strand synthesis reactions were conducted using the kit's components. The double stranded cDNA produced was purified using Agencourt AMPure XP beads and NEBNext adaptors were ligated to the purified cDNAs. The adaptor-ligated DNA was then size-selected using Agencourt AMPure XP beads. Quantities of the size-selected cDNA were increased by PCR enrichment (using the manufacturers protocol) and purified using AMPure XP beads. Library quality subsequently assessed using a Bioanalyzer. The libraries were then sequenced using a HiSeq instrument. Each lane was used to analyze six barcoded libraries. Data from 51 cycles of single-end reads were collected. This ultimately yielded approximately 20 million mapped reads per barcoded sample.

Figure 10:
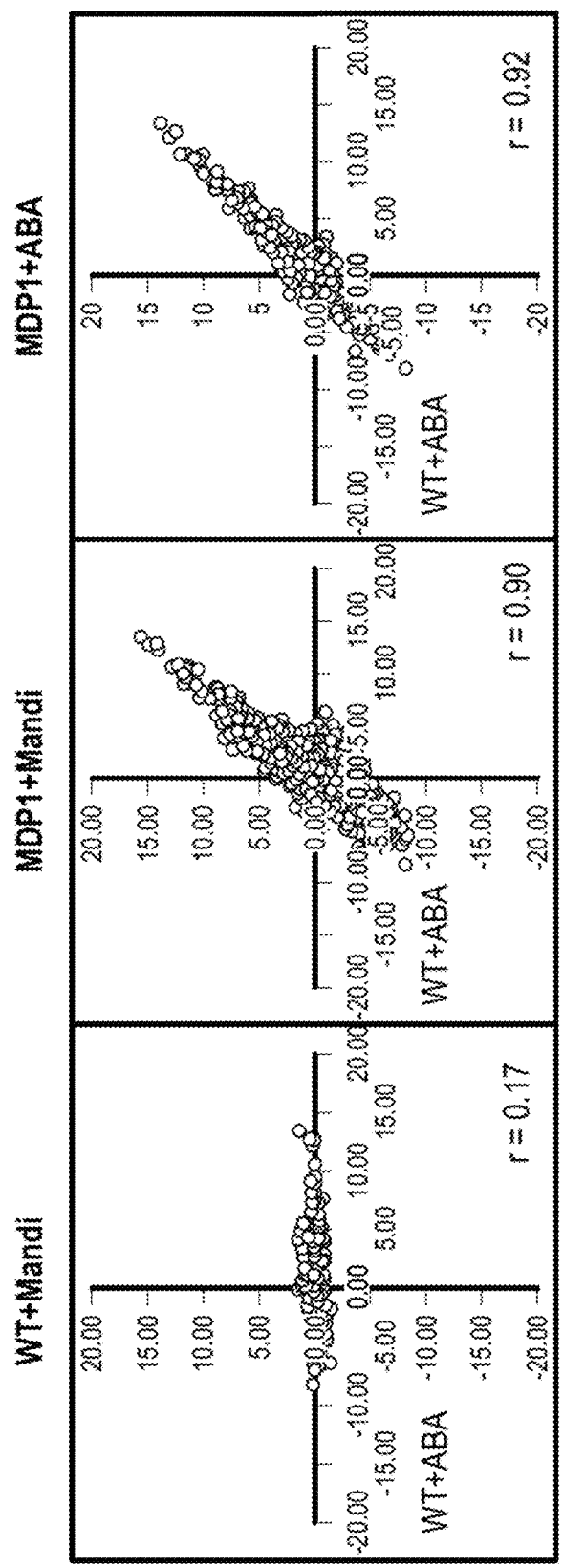
FIG. 10A shows the effect of mandipropamid on gene expression in wildtype *Arabidopsis* plants.
FIG. 10B shows the effect of mandipropamid on gene expression in PYR1$^{mandi}$ transgenic *Arabidopsis* plants.
FIG. 10C shows the effect of ABA on gene expression in PYR1$^{mandi}$ transgenic *Arabidopsis* plants.

The raw HiSeq data was mapped to the *Arabidopsis* genome using the R-based next generation sequencing analysis package, TOPHat, which matches Illumina reads to the *Arabidopsis* reference genome sequence and then calculates the abundance of each gene using the FPKM metric (FPKM=fragments per kilobase of exon per million fragments mapped). TOPHat identified 22,326 genes displaying non-zero FPKM mean values in all samples. There were 20,533 genes with FPKM values greater than 0.1 across all samples and these were used to make comparisons of global gene expression patterns. As shown in FIG. 10A, mandipropamid does not induce a substantial ABA response in wild type plants (r=0.17), however it does induce an ABA-like response in transgenic plants expressing PYR1$^{MANDI}$ (r=0.90; FIG. 10B). Additionally, the PYR1$^{MANDI}$ transgene does not interfere with the endogenous ABA-transcriptional response, as the response of the wild type and MDP1 transgenic genotypes to ABA are highly correlated (r=0.92; FIG. 10C). Thus, mandipropamid induces a genome-wide ABA-like transcription response selectively in transgenic *Arabidopsis* plants expressing PYR1$^{MANDI}$.

Example 12

Expression of PYR1$^{MANDI}$ Causes Modest Alterations in Basal Gene Expression

The PYR1$^{MANDI}$ receptor offers a means to control ABA responses using an orthogonal ligand however the its utility could be affected if expression of the PYR1$^{MANDI}$ protein in is associated with large changes in basal gene expression. We therefore used the RNASeq data generated in the previous example to compare the genome-wide basal levels of mRNAs in wild type Columbia and MDP1 (35S::PYR1$^{MANDI}$) transgenic plants. The Cufflinks software package was used to identify statistically significant differences between samples. Amongst the 20,533 genes with FPKM values greater that 0.1 in all samples, 702 show a statistically significant expression levels (q<0.05) between untreated wild type and MDP1 genotypes. Of these, only 32 genes displayed a difference of greater than 2-fold between the two lines. Of these, PYR1 itself showed the greatest difference (it was 55-fold higher in the MDP1 transgenic line) as a consequence of the 35S::PYR1$^{MANDI}$ transgene. The mean fold-change difference in expression across the 702 significantly different genes was ~43±23%. Thus, these analyses show that expression of PYR1$^{MANDI}$ under the 35S promoter is associated with relatively small changes in basal gene expression in *Arabidopsis*.

Example 13

Additional Evidence that PYR1$^{MANDI}$ Enables Orthogonal Control of Drought Stress Tolerance.

Figure 11:
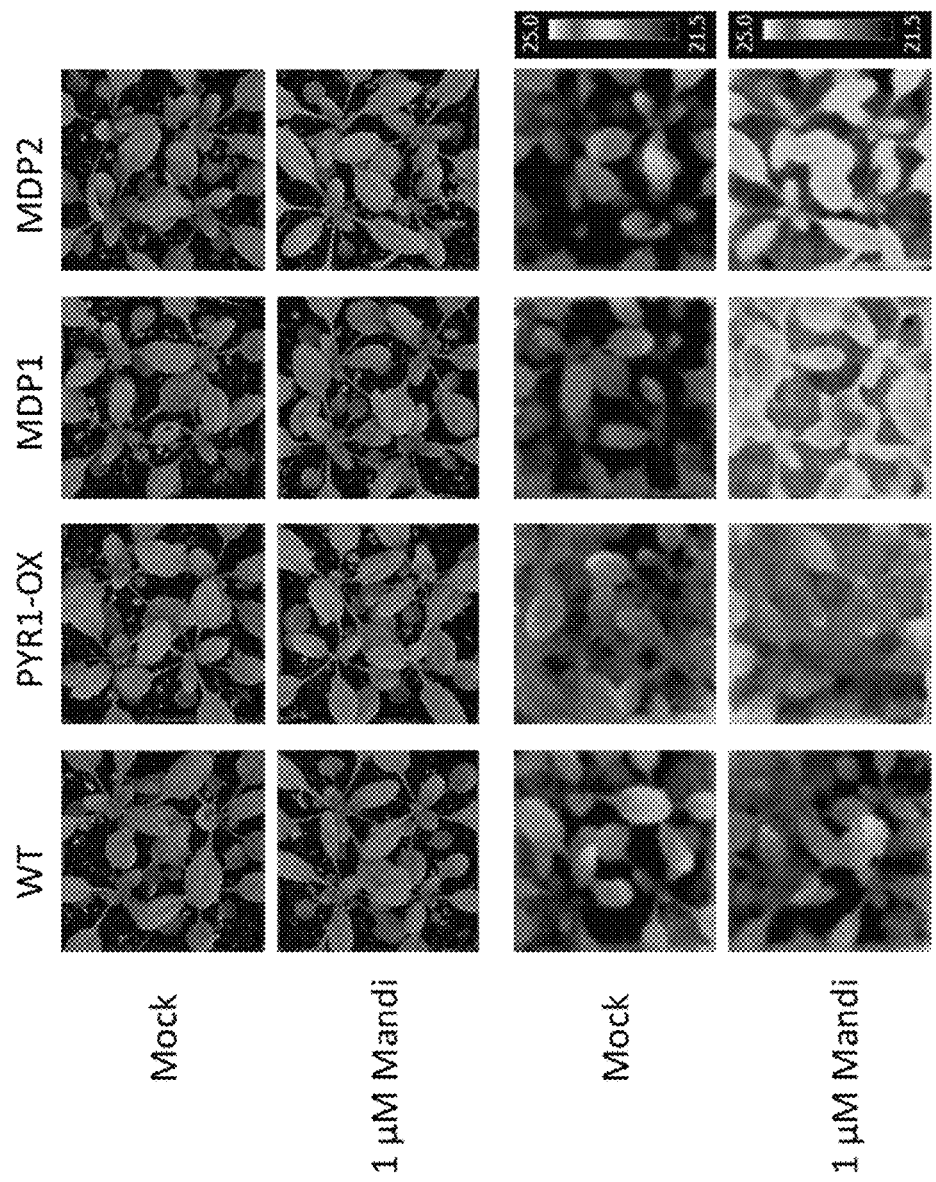
FIG. 11 shows standard imaging (first two rows) and thermal imaging (bottom two rows) results for plants mock-treated or treated with mandipropamid.
Figure 12:
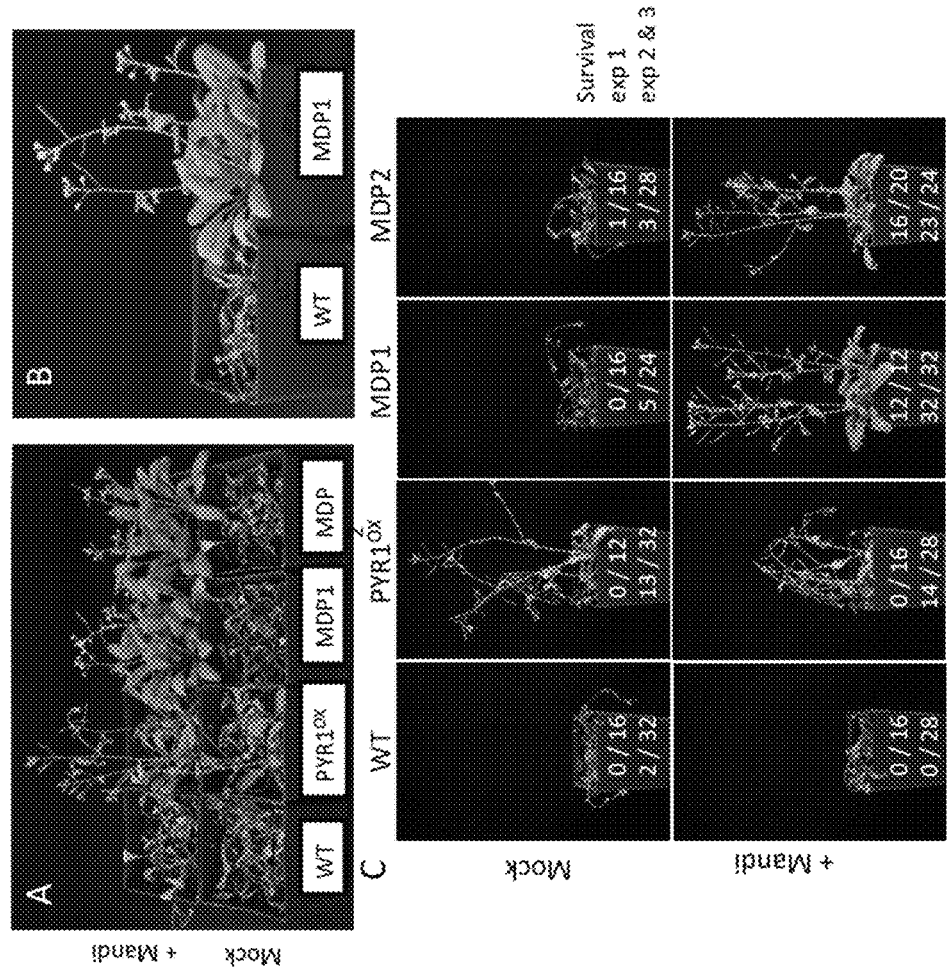
FIG. 12 shows representative p plants following water deprivation of plants of various genotypes, mock-treated or treated with mandipropamid.
Figure 13:
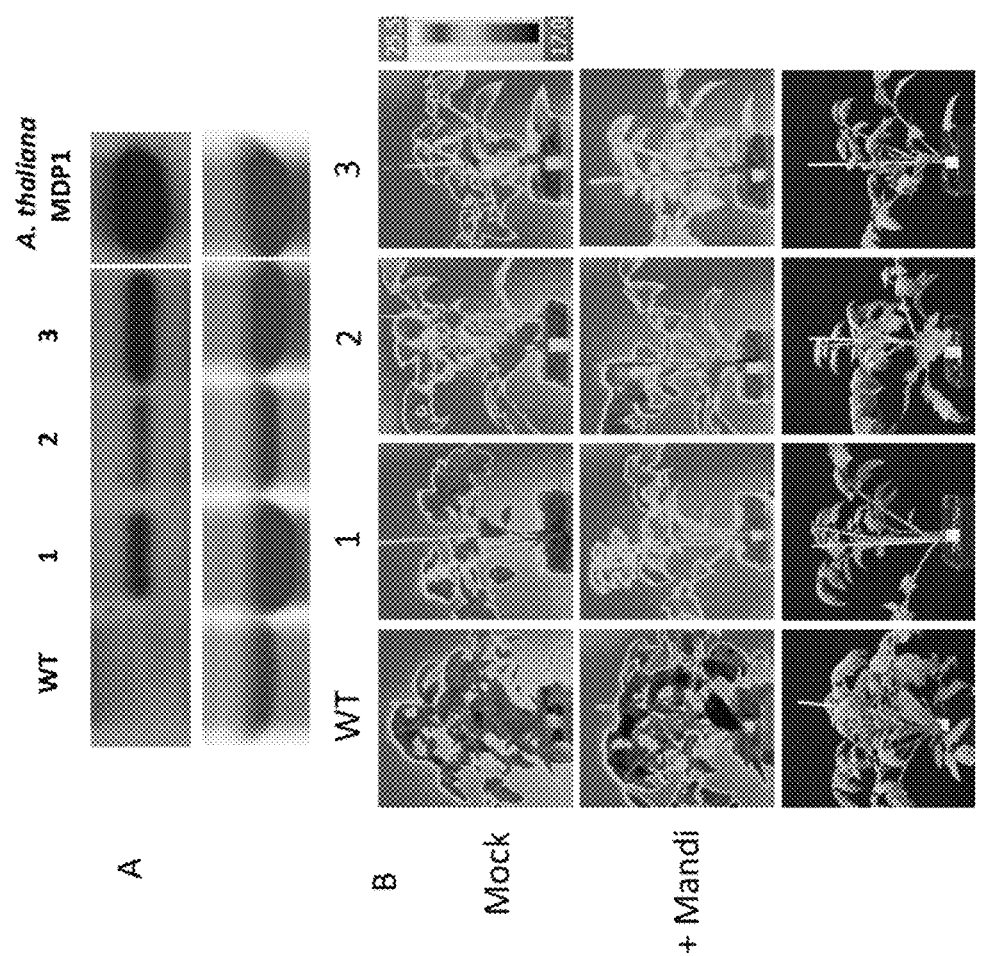
FIG. 13A shows protein expression levels of PYR1$^{MANDI}$ transgenic tomato plants.
FIG. 13B shows thermal imaging of various tomato plants that were mock-treated or treated with mandipropamid.

Examples 6 and 8 disclosed that mandipropamid treatments of PYR1$^{MANDI}$ transgenic plants are sufficient to close guard cells (as indicated by thermal imaging) and confer drought tolerance. To investigate these responses further we performed three additional experiments using wild type Columbia, PYR1-OX and the MDP1 and MDP2 genotypes. Each experiment was conducted independently of the other at different times over the course of 8 months. Each experiment characterized 3 pots of each genotype (each pot contained 4 plants). After 2 weeks (exp. 1) or 3 weeks (Experiments 2 and 3) watering was ceased and the plants were treated with a mock or 1 µM mandipropamid solution made in water containing 0.02% Silwet L-77. These treatments were repeated every 4 (Experiment 1) or 3 days (Experiments 2 and 3). Thermal images were acquired 24 hours post treatment; FIG. 11 shows a representative set of thermal responses that were observed in experiment 3. After 10 to 11 days of water deprivation the plants were re-watered to assess survival rates after extreme water deprivation. FIG. 12 shows representative images of plants 2 days after re-watering from Experiment 3. Inset in each image are the survival counts from Experiment 1 (upper numbers) and Experiments 2 and 3 (lower numbers). The survival rates have been separated because the experimental protocol for Experiment 1 differed from Experiments 2 and 3.

Plants were grown for ~4 weeks until initial floral meristems became obvious, after which watering was ceased and the plants were treated with either a mock or 1 µM mandipropamid solution. These treatments were repeated 3, 6, and 9 days later. 24 hours after the first applications, thermal images were collected and results from a representative experiment are shown in FIG. 11. The MDP1 and MDP2 transgenic lines displayed increased leaf temperature after mandipropamid, but not mock, treatments. These observations indicate that guard cell closure, an ABA-mediated response, is selectively triggered in the PYR1$^{MANDI}$ transgenic plants, as expected based on the experiments described in Example 8. After 11 days of water deprivation the plants were rewatered to assess survival after extreme water deprivation. As shown in FIG. 12 the survival rates of the mandipropamid treated MDP1 and MDP2 genotypes are greatly improved relative to wild type and PYR1-OX controls. The data also show that over-expression of PYR1 is associated with improved stress tolerance, which is consistent with previously published observations of transgenic plants over-expressing different PYR/PYL receptors (Santiago et al. 2009). 35S::PYR1$^{MANDI}$ overexpression does not provide protection in the absence of mandipropamid, presumably because the mutant proteins are unable to be activated by endogenous ABA.

Example 14

Mandipropamid Elicits Guard Cell Closure in Transgenic Tomato Expressing PYR1$^{MANDI}$.

The core ABA response pathway is highly conserved and it is therefore expected that PYR1$^{MANDI}$ should be able to activate ABA responses in response to mandipropamid in most land plants. To investigate if the physiological activity of PYR1$^{MANDI}$ is functional in other species besides *Arabidopsis* we made transgenic 35S::$PYR1^{MANDI}$ tomato. The same construct utilized for construction of *Arabidopsis* transgenics (described in Example 5) was modified to contain a kanamycin selection marker. Tomato was transformed by *Agrobacterium*-mediated transformation, which was conducted as described by Sun et al. (2006) with a few modifications. Surface sterilized tomato seeds (strain UC82B) were germinated on sterilized wet filter paper in a petridish. Cotyledons from 7-day old seedlings were excised and dipped into a suspension of *Agrobacterium* in MS medium containing 100 μM acetosyringone and 10 μM 2-mercaptoethanol for 10 minutes. Explants were then placed on co-cultivation medium containing MS salts, 3% sucrose, 0.3% Gelite and 1.5 mg/L zeatin. After 3 days of co-culture in darkness, the explants were transferred onto callus induction medium containing MS salts, 3% sucrose, 0.3% Gelite, 1.5 mg/L zeatin and 100 mg/L kanamycin and 125 mg/L carbenicillin. Explants were transferred to freshly prepared medium every 2 weeks. Calli displaying shoot buds were transferred to the medium containing 1 mg/L zeatin to simulate shoot elongation. Transgenic shoots 1 cm in length were cut and transferred onto rooting medium containing MS salts, 1.5% sucrose, 0.3% Gelite, 1 mg/L isobutyric acid, 50 mg/L kanamycin, and 125 mg/L carbenicillin. After 2-3 weeks young plants displaying well-developed roots were transferred to the soil.

Three transgenic tomato lines were selected for further characterization (lines 1-3). Leaf protein from these lines was subjected to western blot analyses using an α-PYR1 antibody, as described in Example 9. Given that expression levels affect mandipropamid responsiveness, we compared the $PYR1^{MANDI}$ protein levels between the tomato transgenic and *Arabidopsis* MDP1 lines. As shown in FIG. 13A, the three tomato lines all possess detectable $PYR1^{MANDI}$ protein, although at levels lower than those present in the *Arabidopsis* MDP1 line.

To investigate the physiological activity of $PYR1^{MANDI}$ in these transgenic plants, we propagated the primary transgenics by making cuttings, which allowed us to select similarly sized plants for physiological analyses. To make these clones, ~5 cm long shoots were excised and planted in soil after treatment with a commercial rooting powder (Bonide, Oriskany, N.Y.). Plants were grown in a growth chamber on a 16 hour light and cycle at 25° C. ~3 weeks after clone establishment, the tomato seedlings and wild type controls were treated with a mock solution (0.1% DMSO and 0.05% silwet-77) and then thermal images were collected after 24 hours. Three days later the plants were treated with a solution containing 10 μM mandipropamid, 0.1% DMSO and 0.05% silwet-77. Thermal images were then taken again 24 hours post treatment. As shown in FIG. 13B, the transgenic 35S::$PYR1^{MANDI}$ tomato plants showed an increase in leaf temperature in response to mandipropamid, which demonstrates that $PYR1^{MANDI}$ is functional in tomato. Moreover, the strength of the response correlates with $PYR1^{MANDI}$ protein levels, as was observed with experiments in *Arabidopsis*. These data indicate that mandipropamid elicits guard cell closure in transgenic tomato expressing $PYR1^{MANDI}$ and indicate that the physiological action of the mutant $PYR1^{MANDI}$ receptor is not restricted to *Arabidopsis*.

TABLE 1

| | | Threshold | Signal strength |
|---|---|---|---|
| Dichlobenil | | | |
| Pocket Library Screen | | | |
| K59R | V83L | 100 | +++ |
| K59R | L87P | 100 | + |
| K59R | E94D | 100 | + |
| K59R | F108E | 100 | + |
| K59R | I110M | 100 | + |
| K59R | H115N | 100 | +++ |
| K59R | E141F | 100 | + |
| K59R | E141L | 100 | + |
| K59R | E141Y | 100 | + |
| K59R | E141H | 100 | + |
| K59R | E141Q | 100 | + |
| K59R | M158L | 100 | +++ |
| K59R | M158S | 100 | +++ |
| K59R | M158C | 100 | +++ |
| K59R | M158I | 100 | +++ |
| K59R | M158T | 100 | +++ |
| K59R | M158V | 100 | +++ |
| K59R | M158A | 100 | +++ |
| K59R | M158G | 100 | +++ |
| K59R | F159L | 100 | + |
| K59R | F1591 | 100 | + |
| K59R | F159V | 100 | + |
| K59R | A160C | 100 | + |
| K59R | A160S | 100 | + |
| K59R | A160Y | 100 | + |
| K59R | A160I | 100 | + |
| K59R | A160T | 100 | + |
| K59R | A160N | 100 | + |
| K59R | A160V | 100 | + |
| K59R | T162L | 100 | + |
| K59R | T162Y | 100 | + |
| K59R | T162W | 100 | + |
| K59R | T162K | 100 | + |
| K59R | V164F | 100 | +++ |
| K59R | V164L | 100 | + |
| K59R | V164S | 100 | + |
| K59R | V164Y | 100 | + |
| K59R | V164C | 100 | + |
| K59R | V164H | 100 | + |
| K59R | V164Q | 100 | + |
| K59R | V164T | 100 | + |
| K59R | V164N | 100 | + |
| K59R | V164K | 100 | + |
| K59R | V164A | 100 | + |
| K59R | V164E | 100 | + |
| K59R | V164G | 100 | + |
| K59R | V164M | 100 | + |
| K59R | N167S | 100 | +++ |
| K59R | N167C | 100 | + |
| K59R | N167Q | 100 | + |
| K59R | N167T | 100 | + |
| K59R | N167A | 100 | + |
| K59R | N167D | 100 | + |
| K59R | N167G | 100 | +++ |

TABLE 1-continued

| | | | Signal Threshold | strength |
|---|---|---|---|---|
| Benzothiadiazole | | | | |
| Pocket Library Screen | | | | |
| K59R | V81I | | 100 | + |
| K59R | V83L | | 100 | +++ |
| K59R | A89C | | 100 | ++ |
| K59R | L117C | | 100 | ++ |
| K59R | E141Y | | 100 | ++ |
| K59R | E141K | | 100 | + |
| K59R | M158I | | 100 | + |
| K59R | M158T | | 100 | + |
| K59R | M158C | | 100 | + |
| K59R | M158V | | 100 | + |
| K59R | F159L | | 100 | + |
| K59R | F159T | | 100 | + |
| K59R | F159C | | 100 | + |
| K59R | F159I | | 100 | + |
| K59R | F159V | | 100 | + |
| K59R | F159A | | 100 | +++ |
| K59R | F159M | | 100 | + |
| K59R | A160G | | 100 | ++ |
| K59R | T162Y | | 100 | + |
| K59R | T162W | | 100 | + |
| K59R | T162K | | 100 | + |
| K59R | V164Y | | 100 | + |
| K59R | V164K | | 100 | ++ |
| Combinatorial Mutagenesis Screen I | | | | |
| K59R | A89C | E141Y | 0.2 | |
| K59R | A89C | A160G | 5 | |
| K59R | A89C | V164K | 0.2 | |
| K59R | A89C | L117C | 25 | |
| K59R | L117C | V164K | 100 | |
| K59R | E141Y | A160G | 5 | |
| K59R | A160G | V164K | 5 | |
| K59R | A160G | L117C | 25 | |
| Benoxacor | | | | |
| Pocket Library Screen | | | | |
| K59R | L87F | | 100 | + |
| K59R | A89I | | 100 | + |
| K59R | A89W | | 100 | + |
| K59R | S92I | | 50 | +++ |
| K59R | S92W | | 50 | + |
| K59R | M158C | | 100 | + |
| K59R | M158V | | 100 | + |
| K59R | M158T | | 100 | + |
| K59R | F159V | | 100 | + |
| K59R | T162W | | 50 | + |
| Combinatorial Mutagenesis Screen I | | | | |
| K59R | A89I | S92I | 50 | |
| K59R | A89I | S92W | 50 | |
| Mandipropamid | | | | |
| Pocket Library Screen | | | | |
| K59R | A89W | | 100 | + |
| K59R | F108L | | 100 | + |
| K59R | F108S | | 100 | + |
| K59R | F108C | | 100 | + |
| K59R | F108Q | | 100 | +++ |
| K59R | F108I | | 100 | +++ |
| K59R | F108T | | 100 | ++ |
| K59R | F108N | | 100 | + |
| K59R | F108V | | 100 | + |
| K59R | F108A | | 100 | +++ |
| K59R | F108E | | 100 | + |
| K59R | F108G | | 100 | + |
| K59R | S122G | | 100 | + |
| K59R | F159L | | 100 | +++ |
| K59R | F159I | | 100 | +++ |
| K59R | F159C | | 100 | + |
| K59R | F159T | | 100 | + |
| K59R | F159V | | 100 | + |
| K59R | F159A | | 100 | + |
| K59R | F159M | | 100 | + |
| Combinatorial Mutagenesis Screen I | | | | | |
| K59R | F108Q | S122G | | 10 | |
| K59R | F108A | S122G | | 1 | |
| K59R | F108I | S122G | | 10 | |
| NNK Mutagenesis | | | | | |
| K59R | F108A | S122G | V81C | 0.25 | |
| K59R | F108A | S122G | V81I | 0.25 | |
| K59R | F108A | S122G | V81T | 0.25 | |
| K59R | F108A | S122G | V83L | 0.05 | |
| K59R | F108A | S122G | L87A | 0.25 | |
| K59R | F108A | S122G | F159L | 0.05 | |
| K59R | F108A | S122G | F159M | 0.25 | |
| K59R | F108A | S122G | F159V | 0.25 | |
| K59R | F108A | S122G | A160V | 0.25 | |
| K59R | F108A | S122G | V164I | 0.25 | |
| Recombination Mutagenesis | | | | | |
| Y58H | K59R | F108A | S122G | 0.25 | |
| Combinatorial Mutagenesis II | | | | | |
| Y58H | K59R | V81I | F108A | S122G | 0.05 |
| | K59R | V81I | F108A | S122G | A160V | 0.05 |
| Y58H | K59R | V81I | F108A | S122G | F159L | 0.01 |
| Y58H | K59R | V81I | F108A | S122G | V164I | 0.01 |
| Y58H | K59R | V81I | F108A | S122G | F150L | 0.002 |
| Y58H | K59R | V83L | F108A | S122G | 0.01 |
| Fludioxonil | | | | | |
| Pocket Library Screen | | | | | |
| K59R | V81Y | | | 100 | + |
| K59R | V81I | | | 100 | + |
| K59R | V83L | | | 100 | +++ |
| K59R | L87F | | | 100 | + |
| K59R | L87P | | | 100 | + |
| K59R | S92F | | | 100 | + |
| K59R | E94A | | | 1 | +++ |
| K59R | E94S | | | 100 | ++ |
| K59R | E94D | | | 100 | ++ |
| K59R | F108L | | | 100 | + |
| K59R | Y120F | | | 100 | + |
| K59R | Y120A | | | 100 | ++ |
| K59R | Y120G | | | 100 | + |
| K59R | Y120M | | | 100 | + |
| K59R | E141Y | | | 100 | +++ |
| K59R | M158C | | | 100 | ++ |
| K59R | M158V | | | 100 | + |
| K59R | M158I | | | 100 | ++ |
| K59R | M158T | | | 100 | ++ |
| K59R | F159T | | | 100 | + |
| K59R | F159V | | | 100 | + |
| K59R | F159A | | | 100 | + |
| K59R | A160C | | | 100 | + |
| K59R | T162W | | | 100 | + |
| K59R | V164K | | | 100 | + |
| K59R | N167C | | | 100 | ++ |
| K59R | N167H | | | 100 | + |
| K59R | N167V | | | 100 | + |
| Combinatorial Mutagenesis Screen I | | | | | |
| K59R | E94A | Y120A | | 10 | |
| K59R | E94A | N167C | | 10 | |
| K59R | Y120A | N167C | | 10 | |
| K59R | Y120A | E141Y | | 10 | |

TABLE 2

| 35S promoter lines | Germination on 1 μM mandipropamid | RBCS promoter lines | Germination on 1 μM mandipropamid |
|---|---|---|---|
| WT Control | +++ | | |
| E1 | − | F3 | − |
| E7 | − | F5 | + |
| E8 | − | F6 | + |
| E9 | − | F8 | − |
| E10 | + | F15 | − |
| E15 | − | F18 | + |
| E16 | − | F20 | + |
| E22 | + | F22 | + |
| E23 | + | F23 | + |
| E24 | + | F24 | − |
| E30 | + | F25 | − |
| E31 | − | F26 | − |
| E32 | − | F28 | − |
| E34 | − | F29 | − |
| E36 | − | F32 | − |
| | | F34 | + |

REFERENCES

Clough, S. J., and Bent, A. F. (1998). Floral dip: a simplified method for *Agrobacterium*-mediated transformation of *Arabidopsis thaliana*. The Plant Journal 16, 735-743.

Cutler, S. R., Ehrhardt, D. W., Griffitts, J. S., and Somerville, C. R. (2000). Random GFP cDNA fusions enable visualization of subcellular structures in cells of *Arabidopsis* at a high frequency. PNAS 97, 3718-3723.

Cutler, S. R., Rodriguez, P. L., Finkelstein, R. R., and Abrams, S. R. (2010). Abscisic acid: emergence of a core signaling network. Annual Reviews Plant Biology 61, 651-679.

Dupeux, F., Santiago, J., Betz, K., Twycross, J., Park, S.-Y., Rodriguez, L., Gonzalez-Guzman, M., Jensen, M. R., Krasnogor, N., Blackledge, M., et al. (2011). A thermodynamic switch modulates abscisic acid receptor sensitivity. The EMBO Journal 30, 4171-4184.

Hao, Q., Yin, P., Li, W., Wang, L., Yan, C., Lin, Z., Wu, J. Z., Wang, J., Yan, S. F., and Yan, N. (2011). The molecular basis of ABA-independent inhibition of PP2Cs by a subclass of PYL proteins. Molecular Cell 42, 662-672.

Melcher, K., Ng, L. M., Zhou, X. E., Soon, F. F., Xu, Y., Suino-Powell, K. M., Park, S. Y., Weiner, J. J., Fujii, H., Chinnusamy, V., et al. (2009). A gate-latch-lock mechanism for hormone signalling by abscisic acid receptors. Nature 462, 602-608.

Miyazono, K., Miyakawa, T., Sawano, Y., Kubota, K., Kang, H. J., Asano, A., Miyauchi, Y., Takahashi, M., Zhi, Y., Fujita, Y., et al. (2009). Structural basis of abscisic acid signalling. Nature 462, 609-614.

Mosquna, A., Peterson, F. C., Park, S. Y., Lozano-Juste, J., Volkman, B. F., and Cutler, S. R. (2011). Potent and selective activation of abscisic acid receptors in vivo by mutational stabilization of their agonist-bound conformation. Proceedings of the National Academy of Sciences 108, 20838-20843.

Müller, K. M., Stebel, S. C., Knall, S., Zipf, G., Bernauer, H. S., and Arndt, K. M. (2005). Nucleotide exchange and excision technology (NExT) DNA shuffling: a robust method for DNA fragmentation and directed evolution. Nucl. Acids Res. 33, e117-e117.

Nambara, E., and Marion-Poll, A. (2005). Abscisic acid biosynthesis and catabolism. Annu Rev Plant Biol 56, 165-185.

Ng, L.-M., Soon, F.-F., Zhou, X. E., West, G. M., Kovach, A., Suino-Powell, K. M., Chalmers, M. J., Li, J., Yong, E.-L., Zhu, J.-K., et al. (2011). Structural basis for basal activity and autoactivation of abscisic acid (ABA) signaling SnRK2 kinases. PNAS 108, 21259-21264.

Nishimura, N., Hitomi, K., Arvai, A. S., Rambo, R. P., Hitomi, C., Cutler, S. R., Schroeder, J. I., and Getzoff, E. D. (2009). Structural mechanism of abscisic acid binding and signaling by dimeric PYR1. Science Signalling 326, 1373.

Park, S.-Y., Fung, P., Nishimura, N., Jensen, D. R., Fujii, H., Zhao, Y., Lumba, S., Santiago, J., Rodrigues, A., Chow, T. F., et al. (2009). Abscisic Acid Inhibits Type 2C Protein Phosphatases via the PYR/PYL Family of START Proteins. Science 324, 1068-1071.

Peterson, F. C., Burgie, E. S., Park, S. Y., Jensen, D. R., Weiner, J. J., Bingman, C. A., Chang, C. E. A., Cutler, S. R., Phillips Jr, G. N., and Volkman, B. F. (2010). Structural basis for selective activation of ABA receptors. Nature Structural & Molecular Biology 17, 1109-1113.

Santiago, J., Rodrigues, A., Saez, A., Rubio, S., Antoni, R., Dupeux, F., Park, S. Y., Márquez, J. A., Cutler, S. R., and Rodriguez, P. L. (2009). Modulation of drought resistance by the abscisic acid receptor PYL5 through inhibition of clade A PP2Cs. The Plant Journal 60, 575-588.

Sirault, X. R. R., James, R. A., and Furbank, R. T. (2009). A new screening method for osmotic component of salinity tolerance in cereals using infrared thermography. Funct. Plant Biol. 36, 970-977.

Weiner, J. J., Peterson, F. C., Volkman, B. F., and Cutler, S. R. (2010). Structural and functional insights into core ABA signaling. Current Opinion in Plant Biology 13, 495-502.

Yin, P., Fan, H., Hao, Q., Yuan, X., Wu, D., Pang, Y., Yan, C., Li, W., Wang, J., and Yan, N. (2009). Structural insights into the mechanism of abscisic acid signaling by PYL proteins. Nature Structural & Molecular Biology 16, 1230-1236.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A plant or cell comprising a heterologous expression cassette, the expression cassette comprising a promoter operably linked to a polynucleotide encoding a mutated PYR/PYL receptor polypeptide, wherein the mutated PYR/PYL receptor polypeptide is agonized by mandipropamid when the mandipropamid is contacted to the mutated PYR/PYL receptor polypeptide, wherein the amino acid of the mutated PYR/PYL receptor polypeptide corresponding to position K59 of SEQ ID NO:1 is X, wherein X is alanine, cysteine, aspartic acid, glutamic acid, phenylalanine, glycine, histidine, leucine, methionine, glutamine, arginine, serine, threonine, valine, tyrosine, asparagine, or tryptophan, and wherein:

the mutated PYR/PYL receptor polypeptide further comprises at least one additional mutation at an amino acid corresponding to positions 89, 108, 122, and/or 159 in PYR1 (SEQ ID NO:1) wherein the mutation is selected from A89W, F108L, F108S, F108C, F108Q, F108I, F108T, F108N, F108V, F108A, F108E, F108G, S122G, F159I, F159C, F159T, F159V, F159A, F159M, or combinations thereof; or the amino acid of the mutated PYR/PYL receptor polypeptide corresponding to position S122 of SEQ ID NO:1 is a glycine residue and position F108 of SEQ ID NO:1 is X, wherein X is leucine, serine, cysteine, glutamine, isoleucine, threonine, asparagine, valine, alanine, glutamic acid, or glycine; or the mutated PYR/PYL receptor polypeptide comprises mutations at amino acids corresponding to positions 58, 108, and 122 in PYR 1 (SEQ ID NO:1) wherein the mutations are Y58H, F108A, and S122G; or the mutated PYR/PYL receptor polypeptide comprises mutations at amino acids corresponding to positions 81, 108, 122, and 160 in PYR 1 (SEQ ID NO:1) wherein the mutations are V81I, F108A, S122G, and A160V; or the mutated PYR/PYL receptor polypeptide comprises mutations at amino acids corresponding to positions 58, 81, 108, 122, and 159 in PYR 1 (SEQ ID NO:1) wherein the mutations are Y58H, V81I, F108A, S122G, and F159L; or the mutated PYR/PYL receptor polypeptide comprises mutations at amino acids corresponding to positions 58, 81, 108, 122, and 164 in PYR 1 (SEQ ID NO:1) wherein the mutations are Y58H, V81I, F108A, S122G, and V164I.

2. The plant or cell of claim 1, wherein the mutated PYR/PYL receptor polypeptide further comprises at least one additional mutation at an amino acid corresponding to positions 89, 108, 122, and/or 159 in PYR1 (SEQ ID NO:1) wherein the mutation is selected from A89W, F108L, F108S, F108C, F108Q, F108I, F108T, F108N, F108V, F108A, F108E, F108G, S122G, F159I, F159C, F159T, F159V, F159A, F159M, or combinations thereof.

3. The plant or cell of claim 1, wherein the amino acid of the mutated PYR/PYL receptor polypeptide corresponding to position S122 of SEQ ID NO:1 is a glycine residue and position F108 of SEQ ID NO:1 is X, wherein X is leucine, serine, cysteine, glutamine, isoleucine, threonine, asparagine, valine, alanine, glutamic acid, or glycine.

4. The plant or cell of claim 3, wherein the mutated PYR/PYL receptor polypeptide further comprises at least one additional mutation at an amino acid corresponding to positions 58, 81, 83, 87, 159, 160, and/or 164 in PYR 1 (SEQ ID NO:1) wherein the mutation is selected from Y58H, V81C, V81I, V81T, V83L, L87A, F159L, F159M, F159V, A160V, V164I, or combinations thereof.

5. The plant or cell of claim 1, wherein the mutated PYR/PYL receptor polypeptide comprises mutations at amino acids corresponding to positions 58, 108, and 122 in PYR 1 (SEQ ID NO:1) wherein the mutations are Y58H, F108A, and S122G.

6. The plant or cell of claim 5, wherein the mutated PYR/PYL receptor polypeptide further comprises at least one additional mutation at an amino acid corresponding to positions 81 and/or 83 in PYR1 (SEQ ID NO:1) wherein the mutation is selected from V81I, V83L, or combinations thereof.

7. The plant or cell of claim 5 wherein the mutated PYR/PYL receptor polypeptide further comprises at least one additional mutation at an amino acid corresponding to positions 159 and/or 160 in PYR1 (SEQ ID NO:1) wherein the mutation is selected from A160V, V164I, F159L, or combinations thereof.

8. The plant or cell of claim 1, wherein the mutated PYR/PYL receptor polypeptide comprises mutations at amino acids corresponding to positions 81, 108, 122, and 160 in PYR 1 (SEQ ID NO:1) wherein the mutations are V81I, F108A, S122G, and A160V.

9. The plant or cell of claim 1, wherein the mutated PYR/PYL receptor polypeptide comprises mutations at amino acids corresponding to positions 58, 81, 108, 122, and 159 in PYR 1 (SEQ ID NO:1) wherein the mutations are Y58H, V81I, F108A, S122G, and F159L.

10. The plant or cell of claim 1, wherein the mutated PYR/PYL receptor polypeptide comprises mutations at amino acids corresponding to positions 58, 81, 108, 122, and 164 in PYR 1 (SEQ ID NO:1) wherein the mutations are Y58H, V81I, F108A, S122G, and V164I.

11. The plant or cell of claim 1, wherein the mutated PYR/PYL receptor polypeptide comprises at least one mutation at an amino acid residue comprising the ligand-binding pocket of the PYR/PYL receptor polypeptide.

12. The plant of claim 1, wherein the plant has improved abiotic stress tolerance when contacted with mandipropamid as compared to a plant lacking the expression cassette.

13. The cell of claim 1, wherein the cell is a plant, animal, mammalian, or fungal cell.

14. A plant cell from the plant of claim 1.

15. A method of improving abiotic stress or inhibiting seed germination in the plant of claim 1 by contacting the plant with mandipropamid.

16. An isolated nucleic acid comprising a polynucleotide encoding the mutated PYR/PYL receptor polypeptide of claim 1.

* * * * *

SEQUENCE LISTING

<160> NUMBER OF SEQ ID NOS: 111

<210> SEQ ID NO 1
<211> LENGTH: 191
<212> TYPE: PRT
<213> ORGANISM: Arabidopsis thaliana -continued

```
<220> FEATURE:
<223> OTHER INFORMATION: thale cress PYR/PYL receptor, Pyrabactin
      resistance 1, abscisic acid receptor PYR1 (PYR1), ABI1-binding
      protein 6 (ABIP6), regulatory components of ABA receptor 11
      (RCAR11), At4g17870, T6K21.50

<400> SEQUENCE: 1

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 2
<211> LENGTH: 221
<212> TYPE: PRT
<213> ORGANISM: Arabidopsis thaliana
<220> FEATURE:
<223> OTHER INFORMATION: thale cress PYR/PYL receptor, abscisic acid
      receptor PYL1, PYR1-like protein 1 (PYL1), ABI1-binding protein 6
      (ABIP6), regulatory components of ABA receptor 9 (RCAR12),
      At5g46790, MZA15.21

<400> SEQUENCE: 2

Met Ala Asn Ser Glu Ser Ser Ser Pro Val Asn Glu Glu Asn
1               5                   10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
        35                  40                  45

Thr Tyr Gln Leu Gly Asn Gly Arg Cys Ser Ser Leu Leu Ala Gln Arg
    50                  55                  60

Ile His Ala Pro Pro Glu Thr Val Trp Ser Val Val Arg Arg Phe Asp
65                  70                  75                  80

Arg Pro Gln Ile Tyr Lys His Phe Ile Lys Ser Cys Asn Val Ser Glu
                85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
```

```
            115                 120                 125
Asp Arg Arg Val Thr Gly Phe Ser Ile Thr Gly Gly Glu His Arg Leu
        130                 135                 140
Arg Asn Tyr Lys Ser Val Thr Thr Val His Arg Phe Glu Lys Glu Glu
145                 150                 155                 160
Glu Glu Glu Arg Ile Trp Thr Val Val Leu Glu Ser Tyr Val Val Asp
                165                 170                 175
Val Pro Glu Gly Asn Ser Glu Glu Asp Thr Arg Leu Phe Ala Asp Thr
            180                 185                 190
Val Ile Arg Leu Asn Leu Gln Lys Leu Ala Ser Ile Thr Glu Ala Met
        195                 200                 205
Asn Arg Asn Asn Asn Asn Asn Ser Ser Gln Val Arg
    210                 215                 220

<210> SEQ ID NO 3
<211> LENGTH: 190
<212> TYPE: PRT
<213> ORGANISM: Arabidopsis thaliana
<220> FEATURE:
<223> OTHER INFORMATION: thale cress PYR/PYL receptor, abscisic acid
      receptor PYL2, PYR1-like protein 2 (PYL2), ABI1-binding protein
      6 (ABIP6), regulatory components of ABA receptor 14 (RCAR14), Bet
      v I allergen family protein, At2g26040, T19L18.15

<400> SEQUENCE: 3

Met Ser Ser Ser Pro Ala Val Lys Gly Leu Thr Asp Glu Glu Gln Lys
  1               5                  10                  15
Thr Leu Glu Pro Val Ile Lys Thr Tyr His Gln Phe Glu Pro Asp Pro
             20                  25                  30
Thr Thr Cys Thr Ser Leu Ile Thr Gln Arg Ile His Ala Pro Ala Ser
         35                  40                  45
Val Val Trp Pro Leu Ile Arg Arg Phe Asp Asn Pro Glu Arg Tyr Lys
     50                  55                  60
His Phe Val Lys Arg Cys Arg Leu Ile Ser Gly Asp Gly Asp Val Gly
 65                  70                  75                  80
Ser Val Arg Glu Val Thr Val Ile Ser Gly Leu Pro Ala Ser Thr Ser
                 85                  90                  95
Thr Glu Arg Leu Glu Phe Val Asp Asp Asp His Arg Val Leu Ser Phe
            100                 105                 110
Arg Val Val Gly Gly Glu His Arg Leu Lys Asn Tyr Lys Ser Val Thr
        115                 120                 125
Ser Val Asn Glu Phe Leu Asn Gln Asp Ser Gly Lys Val Tyr Thr Val
    130                 135                 140
Val Leu Glu Ser Tyr Thr Val Asp Ile Pro Glu Gly Asn Thr Glu Glu
145                 150                 155                 160
Asp Thr Lys Met Phe Val Asp Thr Val Val Lys Leu Asn Leu Gln Lys
                165                 170                 175
Leu Gly Val Ala Ala Thr Ser Ala Pro Met His Asp Asp Glu
            180                 185                 190

<210> SEQ ID NO 4
<211> LENGTH: 209
<212> TYPE: PRT
<213> ORGANISM: Arabidopsis thaliana
<220> FEATURE:
<223> OTHER INFORMATION: thale cress PYR/PYL receptor, abscisic acid
      receptor PYL3, PYR1-like protein 3 (PYL3), regulatory components
      of ABA receptor 13 (RCAR13), At1g73000, F3N23.20
```

```
<400> SEQUENCE: 4

Met Asn Leu Ala Pro Ile His Asp Pro Ser Ser Ser Thr Thr Thr
1               5                   10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
        35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65              70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
        115                 120                 125

Ile Leu Ser Phe Arg Val Leu Gly Gly Glu His Arg Leu Asn Asn Tyr
    130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
        195                 200                 205

Thr

<210> SEQ ID NO 5
<211> LENGTH: 207
<212> TYPE: PRT
<213> ORGANISM: Arabidopsis thaliana
<220> FEATURE:
<223> OTHER INFORMATION: thale cress PYR/PYL receptor, abscisic acid
      receptor PYL4, PYR1-like protein 4 (PYL4), ABI1-binding protein 2
      (ABIP2), regulatory components of ABA receptor 10 (RCAR10),
      At2g38310, T19C21.20

<400> SEQUENCE: 5

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
            20                  25                  30

Leu Ser Arg Asp Ser Thr Ala Ala Arg Phe His Thr His Glu Val Gly
        35                  40                  45

Pro Asn Gln Cys Cys Ser Ala Val Ile Gln Glu Ile Ser Ala Pro Ile
    50                  55                  60

Ser Thr Val Trp Ser Val Val Arg Arg Phe Asp Asn Pro Gln Ala Tyr
65              70                  75                  80

Lys His Phe Leu Lys Ser Cys Ser Val Ile Gly Gly Asp Gly Asp Asn
                85                  90                  95

Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
        115                 120                 125
```

Ser Phe Ser Val Val Gly Gly Asp His Arg Leu Ser Asn Tyr Arg Ser
            130                 135                 140

Val Thr Thr Leu His Pro Ser Pro Ile Ser Gly Thr Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
            180                 185                 190

Ile Ala Glu Asn Thr Ala Ala Glu Ser Lys Lys Lys Met Ser Leu
            195                 200                 205

<210> SEQ ID NO 6
<211> LENGTH: 203
<212> TYPE: PRT
<213> ORGANISM: Arabidopsis thaliana
<220> FEATURE:
<223> OTHER INFORMATION: thale cress PYR/PYL receptor, abscisic acid
      receptor PYL5, PYR1-like protein 5 (PYL5), ABI1-binding protein
      3 (ABIP3), regulatory components of ABA receptor 8 (RCAR8), Bet v
      I allergen family protein, At5g05440, K18I23.25

<400> SEQUENCE: 6

Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30

Val Cys Leu Thr Arg Gly Met His Val Pro Glu His Val Ala Met His
            35                  40                  45

His Thr His Asp Val Gly Pro Asp Gln Cys Cys Ser Ser Val Val Gln
        50                  55                  60

Met Ile His Ala Pro Pro Glu Ser Val Trp Ala Leu Val Arg Arg Phe
65                  70                  75                  80

Asp Asn Pro Lys Val Tyr Lys Asn Phe Ile Arg Gln Cys Arg Ile Val
                85                  90                  95

Gln Gly Asp Gly Leu His Val Gly Asp Leu Arg Glu Val Met Val Val
            100                 105                 110

Ser Gly Leu Pro Ala Val Ser Ser Thr Glu Arg Leu Glu Ile Leu Asp
            115                 120                 125

Glu Glu Arg His Val Ile Ser Phe Ser Val Val Gly Gly Asp His Arg
        130                 135                 140

Leu Lys Asn Tyr Arg Ser Val Thr Thr Leu His Ala Ser Asp Asp Glu
145                 150                 155                 160

Gly Thr Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
            180                 185                 190

Leu Gln Ser Leu Ala Arg Ser Thr Asn Arg Gln
            195                 200

<210> SEQ ID NO 7
<211> LENGTH: 215
<212> TYPE: PRT
<213> ORGANISM: Arabidopsis thaliana
<220> FEATURE:
<223> OTHER INFORMATION: thale cress PYR/PYL receptor, abscisic acid
      receptor PYL6, PYR1-like protein 6 (PYL6), ABI1-binding protein
      5 (ABIP5), regulatory components of ABA receptor 9 (RCAR9), Bet
      v I allergen family protein, At2g40330, T7M7.15

-continued

```
<400> SEQUENCE: 7

Met Pro Thr Ser Ile Gln Phe Gln Arg Ser Ser Thr Ala Ala Glu Ala
1               5                   10                  15

Ala Asn Ala Thr Val Arg Asn Tyr Pro His His His Gln Lys Gln Val
            20                  25                  30

Gln Lys Val Ser Leu Thr Arg Gly Met Ala Asp Val Pro Glu His Val
        35                  40                  45

Glu Leu Ser His Thr His Val Val Gly Pro Ser Gln Cys Phe Ser Val
    50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125

Ile Met Asp Asp Asp Arg His Val Ile Ser Phe Ser Val Val Gly Gly
    130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190

Ala Asp Thr Ile Val Arg Cys Asn Leu Gln Ser Leu Ala Lys Leu Ala
        195                 200                 205

Glu Asn Thr Ser Lys Phe Ser
    210                 215

<210> SEQ ID NO 8
<211> LENGTH: 211
<212> TYPE: PRT
<213> ORGANISM: Arabidopsis thaliana
<220> FEATURE:
<223> OTHER INFORMATION: thale cress PYR/PYL receptor, abscisic acid
      receptor PYL7, PYR1-like protein 7 (PYL7), ABI1-binding protein 7
      (ABIP7), regulatory components of ABA receptor 2 (RCAR2),
      At4g01026

<400> SEQUENCE: 8

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
            20                  25                  30

Glu Asn Gln Cys Thr Ser Val Leu Val Lys Tyr Ile Gln Ala Pro Val
        35                  40                  45

His Leu Val Trp Ser Leu Val Arg Arg Phe Asp Gln Pro Gln Lys Tyr
    50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu Glu His Ile Leu Gly Ile
            100                 105                 110

Asn Ile Ile Gly Gly Asp His Arg Leu Lys Asn Tyr Ser Ser Ile Leu
```

```
                    115                 120                 125
Thr Val His Pro Glu Met Ile Asp Gly Arg Ser Gly Thr Met Val Met
    130                 135                 140
Glu Ser Phe Val Val Asp Val Pro Gln Gly Asn Thr Lys Asp Asp Thr
145                 150                 155                 160
Cys Tyr Phe Val Glu Ser Leu Ile Lys Cys Asn Leu Lys Ser Leu Ala
                165                 170                 175
Cys Val Ser Glu Arg Leu Ala Ala Gln Asp Ile Thr Asn Ser Ile Ala
                180                 185                 190
Thr Phe Cys Asn Ala Ser Asn Gly Tyr Arg Glu Lys Asn His Thr Glu
                195                 200                 205
Thr Asn Leu
        210

<210> SEQ ID NO 9
<211> LENGTH: 188
<212> TYPE: PRT
<213> ORGANISM: Arabidopsis thaliana
<220> FEATURE:
<223> OTHER INFORMATION: thale cress PYR/PYL receptor, abscisic acid
      receptor PYL8, PYR1-like protein 8 (PYL8), ABI1-binding protein
      1 (ABIP1), regulatory components of ABA receptor 3 (RCAR3),
      At5g53160, MFH8.10

<400> SEQUENCE: 9

Met Glu Ala Asn Gly Ile Glu Asn Leu Thr Asn Pro Asn Gln Glu Arg
  1               5                  10                  15
Glu Phe Ile Arg Arg His His Lys His Glu Leu Val Asp Asn Gln Cys
                 20                  25                  30
Ser Ser Thr Leu Val Lys His Ile Asn Ala Pro Val His Ile Val Trp
             35                  40                  45
Ser Leu Val Arg Arg Phe Asp Gln Pro Gln Lys Tyr Lys Pro Phe Ile
 50                  55                  60
Ser Arg Cys Val Val Lys Gly Asn Met Glu Ile Gly Thr Val Arg Glu
 65                  70                  75                  80
Val Asp Val Lys Ser Gly Leu Pro Ala Thr Arg Ser Thr Glu Arg Leu
                 85                  90                  95
Glu Leu Leu Asp Asp Asn Glu His Ile Leu Ser Ile Arg Ile Val Gly
            100                 105                 110
Gly Asp His Arg Leu Lys Asn Tyr Ser Ser Ile Ile Ser Leu His Pro
            115                 120                 125
Glu Thr Ile Glu Gly Arg Ile Gly Thr Leu Val Ile Glu Ser Phe Val
        130                 135                 140
Val Asp Val Pro Glu Gly Asn Thr Lys Asp Glu Thr Cys Tyr Phe Val
145                 150                 155                 160
Glu Ala Leu Ile Lys Cys Asn Leu Lys Ser Leu Ala Asp Ile Ser Glu
                165                 170                 175
Arg Leu Ala Val Gln Asp Thr Thr Glu Ser Arg Val
            180                 185

<210> SEQ ID NO 10
<211> LENGTH: 187
<212> TYPE: PRT
<213> ORGANISM: Arabidopsis thaliana
<220> FEATURE:
<223> OTHER INFORMATION: thale cress PYR/PYL receptor, abscisic acid
      receptor PYL9, PYR1-like protein 9 (PYL9), ABI1-binding protein 4
      (ABIP4), regulatory components of ABA receptor 1 (RCAR1),
      At1g01360, F6F3.16
```

<400> SEQUENCE: 10

```
Met Met Asp Gly Val Glu Gly Thr Ala Met Tyr Gly Gly Leu Glu
1               5                  10                  15

Thr Val Gln Tyr Val Arg Thr His His Gln His Leu Cys Arg Glu Asn
                20                  25                  30

Gln Cys Thr Ser Ala Leu Val Lys His Ile Lys Ala Pro Leu His Leu
            35                  40                  45

Val Trp Ser Leu Val Arg Arg Phe Asp Gln Pro Gln Lys Tyr Lys Pro
    50                  55                  60

Phe Val Ser Arg Cys Thr Val Ile Gly Asp Pro Glu Ile Gly Ser Leu
65                  70                  75                  80

Arg Glu Val Asn Val Lys Ser Gly Leu Pro Ala Thr Thr Ser Thr Glu
                85                  90                  95

Arg Leu Glu Leu Leu Asp Asp Glu Glu His Ile Leu Gly Ile Lys Ile
            100                 105                 110

Ile Gly Gly Asp His Arg Leu Lys Asn Tyr Ser Ser Ile Leu Thr Val
        115                 120                 125

His Pro Glu Ile Ile Glu Gly Arg Ala Gly Thr Met Val Ile Glu Ser
130                 135                 140

Phe Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185
```

<210> SEQ ID NO 11
<211> LENGTH: 183
<212> TYPE: PRT
<213> ORGANISM: Arabidopsis thaliana
<220> FEATURE:
<223> OTHER INFORMATION: thale cress PYR/PYL receptor, abscisic acid
      receptor PYL10, PYR1-like protein 10 (PYL10), ABI1-binding protein
      8 (ABIP8), regulatory components of ABA receptor 4 (RCAR4),
      At4g27920, T13J8.30

<400> SEQUENCE: 11

```
Met Asn Gly Asp Glu Thr Lys Lys Val Glu Ser Glu Tyr Ile Lys Lys
1               5                  10                  15

His His Arg His Glu Leu Val Glu Ser Gln Cys Ser Ser Thr Leu Val
                20                  25                  30

Lys His Ile Lys Ala Pro Leu His Leu Val Trp Ser Ile Val Arg Arg
            35                  40                  45

Phe Asp Glu Pro Gln Lys Tyr Lys Pro Phe Ile Ser Arg Cys Val Val
    50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
        115                 120                 125

Gly Lys Thr Gly Thr Leu Ala Ile Glu Ser Phe Val Val Asp Val Pro
130                 135                 140
```

```
Glu Gly Asn Thr Lys Glu Glu Thr Cys Phe Phe Val Glu Ala Leu Ile
145                 150                 155                 160

Gln Cys Asn Leu Asn Ser Leu Ala Asp Val Thr Glu Arg Leu Gln Ala
            165                 170                 175

Glu Ser Met Glu Lys Lys Ile
            180
```

<210> SEQ ID NO 12
<211> LENGTH: 161
<212> TYPE: PRT
<213> ORGANISM: Arabidopsis thaliana
<220> FEATURE:
<223> OTHER INFORMATION: thale cress PYR/PYL receptor, abscisic acid
      receptor PYL11, PYR1-like protein 11 (PYL11), regulatory
      components of ABA receptor 5 (RCAR5), Bet v I allergen family
      protein, At5g45860, K15I22.6

<400> SEQUENCE: 12

```
Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
        115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160

Leu
```

<210> SEQ ID NO 13
<211> LENGTH: 159
<212> TYPE: PRT
<213> ORGANISM: Arabidopsis thaliana
<220> FEATURE:
<223> OTHER INFORMATION: thale cress PYR/PYL receptor, abscisic acid
      receptor PYL12, PYR1-like protein 12 (PYL12), regulatory
      components of ABA receptor 6 (RCAR6), Bet v I allergen family
      protein, At5g45870, K15I22.7

<400> SEQUENCE: 13

```
Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
        35                  40                  45

Ser Gly Asp Gly Gly Glu Gly Ser Val Arg Glu Val Thr Val Val Ser
    50                  55                  60
```

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
        115                 120                 125

Thr Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155

<210> SEQ ID NO 14
<211> LENGTH: 164
<212> TYPE: PRT
<213> ORGANISM: Arabidopsis thaliana
<220> FEATURE:
<223> OTHER INFORMATION: thale cress PYR/PYL receptor, abscisic acid
      receptor PYL13, PYR1-like protein 13 (PYL13), regulatory
      components of ABA receptor 7 (RCAR7), At4g18620, F28A21.30

<400> SEQUENCE: 14

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
                20                  25                  30

Lys Pro Gln Ala Tyr Gln Arg Phe Val Lys Ser Cys Thr Met Arg Ser
            35                  40                  45

Gly Gly Gly Gly Gly Lys Gly Glu Gly Lys Gly Ser Val Arg Asp
        50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Val Glu Ser Tyr Val
        115                 120                 125

Val Asp Val Pro Glu Gly Thr Ser Glu Glu Asp Thr Ile Phe Phe Val
    130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 15
<211> LENGTH: 191
<212> TYPE: PRT
<213> ORGANISM: Brassica oleracea
<220> FEATURE:
<223> OTHER INFORMATION: wild cabbage Streptomyces cyclase/dehydrase
      family protein, locus tag 40.t00062, GenBank Accession No.
      ABD65175.1, GI:89257688

<400> SEQUENCE: 15

Met Pro Ser Gln Leu Thr Pro Glu Glu Arg Ser Glu Leu Ala Gln Ser
1               5                   10                  15

Ile Ala Glu Phe His Thr Tyr His Leu Gly Pro Gly Ser Cys Ser Ser
                20                  25                  30

```
Leu His Ala Gln Arg Ile His Ala Pro Pro Glu Ile Val Trp Ser Val
            35                  40                  45

Val Arg Arg Phe Asp Lys Pro Gln Thr Tyr Lys His Phe Ile Lys Ser
 50                  55                  60

Cys Ser Val Glu Asp Gly Phe Glu Met Arg Val Gly Cys Thr Arg Ala
 65                  70                  75                  80

Val Asn Val Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
                115                 120                 125

Phe Glu Lys Glu Arg Arg Ile Trp Thr Val Val Leu Glu Ser Tyr Val
                130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Ser Gly Ala Gln Val Thr
                180                 185                 190
```

<210> SEQ ID NO 16
<211> LENGTH: 281
<212> TYPE: PRT
<213> ORGANISM: Brassica oleracea
<220> FEATURE:
<223> OTHER INFORMATION: wild cabbage Streptomyces cyclase/dehydrase
      family protein, locus tag 23.t00047, GenBank Accession No.
      ABD65631.1, GI:89274227

<400> SEQUENCE: 16

```
Met Pro Ser Glu Leu Thr Gln Glu Glu Arg Ser Lys Leu Thr Gln Ser
 1               5                  10                  15

Ile Ser Glu Phe His Thr Tyr His Leu Gly Pro Gly Ser Cys Ser Ser
                 20                  25                  30

Leu His Ala Gln Arg Ile His Ala Pro Pro Glu Ile Val Trp Ser Val
            35                  40                  45

Val Arg Gln Phe Asp Lys Pro Gln Thr Tyr Lys His Phe Ile Lys Ser
 50                  55                  60

Cys Ser Val Glu Glu Gly Phe Glu Met Arg Val Gly Cys Thr Arg Asp
 65                  70                  75                  80

Val Ile Val Ile Ser Gly Leu Pro Ala Asn Thr Ser Thr Glu Arg Leu
                 85                  90                  95

Asp Met Leu Asp Asp Glu Arg Arg Val Thr Gly Phe Ser Ile Ile Gly
                100                 105                 110

Gly Glu His Arg Leu Lys Asn Tyr Lys Ser Val Thr Thr Val His Arg
                115                 120                 125

Phe Glu Arg Glu Arg Arg Ile Trp Thr Val Val Leu Glu Ser Tyr Val
                130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Arg Gly Ser Arg Glu Thr Thr
                180                 185                 190
```

-continued

```
Cys Arg Glu Ser Phe His Leu Ile Thr Ala Phe Glu Lys Gln Arg Gln
            195                 200                 205

Ile Thr Glu Pro Thr Val Tyr Gln Asn Pro Pro Tyr His Thr Gly Met
    210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
                245                 250                 255

Arg Met Tyr Gln Arg Phe Trp Gly Ile Arg Gln Leu Gln Arg Pro Arg
            260                 265                 270

Gln Ser Phe Gly Glu Arg Gln Ser Ile
        275                 280

<210> SEQ ID NO 17
<211> LENGTH: 453
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00015766001, GenBank Accession No.
      CAO63410.1, GI:157341954

<400> SEQUENCE: 17

Met Gln Met Lys Tyr Leu Glu Gly Lys Gln Asn Leu Met Glu Glu Lys
1               5                   10                  15

Gly Glu Lys Gln Cys Ile Pro Met Asp Leu Ala Val Arg Glu Ala Gln
            20                  25                  30

Phe Lys Gly Ser Leu Leu Asp Arg Ile Thr Trp Leu Glu Gln Arg Leu
        35                  40                  45

His Lys Leu Ser Leu Gln Leu Glu Thr Arg Ser Lys Gln Gln Pro His
    50                  55                  60

Pro Ser Arg Met Gln Thr Ala Gly Glu Thr Ser Ser Arg His Gly Pro
65                  70                  75                  80

Lys Lys Glu Leu Ser Cys Ser Phe Pro Val Phe Ser Thr Arg Asn His
                85                  90                  95

Asn His Gly His Lys Gln Thr Ser Gln Phe His Val Pro Arg Phe Glu
            100                 105                 110

Tyr Gln Glu Gly Gly Arg Glu Asn Pro Ala Val Val Ile Thr Lys Leu
        115                 120                 125

Thr Pro Phe His His Pro Lys Ile Ile Thr Ile Leu Phe Pro Ile Ser
    130                 135                 140

Asn Tyr Phe Ile Ile Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
        195                 200                 205

Ser Met Ala Glu Ala Glu Ser Glu Asp Ser Glu Thr Thr Thr Pro Thr
    210                 215                 220

Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
                245                 250                 255

Gly Gln Cys Ser Ser Leu Leu Ala Gln Arg Val His Ala Pro Leu Pro
```

```
                    260                 265                 270
Thr Val Trp Ser Val Val Arg Arg Phe Asp Lys Pro Gln Thr Tyr Lys
            275                 280                 285
His Phe Ile Lys Ser Cys His Val Glu Asp Gly Phe Glu Met Arg Val
        290                 295                 300
Gly Cys Leu Arg Asp Val Asn Val Ile Ser Gly Leu Pro Ala Glu Thr
305                 310                 315                 320
Ser Thr Glu Arg Leu Asp Ile Leu Asp Asp Glu Arg His Val Thr Gly
                325                 330                 335
Phe Ser Ile Ile Gly Gly Glu His Arg Leu Arg Asn Tyr Arg Ser Val
            340                 345                 350
Thr Thr Asn His Gly Gly Glu Ile Trp Thr Val Val Leu Glu Ser Tyr
        355                 360                 365
Val Val Asp Met Pro Glu Gly Asn Thr Glu Glu Asp Thr Arg Leu Phe
370                 375                 380
Ala Asp Thr Val Val Lys Leu Asn Leu Gln Lys Leu Ala Ser Val Thr
385                 390                 395                 400
Glu Val Ser Gln Ser Cys Asn Tyr Pro Cys Gln Phe His Ile Ile Glu
                405                 410                 415
Asn Glu Asp Ile Gln Pro Glu Met Asn Leu Gly Val Leu Thr Thr
            420                 425                 430
Ser Ile Glu Glu Gln Arg Lys Lys Lys Arg Val Val Ala Met Lys Asp
        435                 440                 445
Gly Ser Thr Ser Ser
    450
```

<210> SEQ ID NO 18
<211> LENGTH: 195
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_033963, GenBank
      Accession No. CAN64657.1, GI:147789129
<220> FEATURE:
<221> NAME/KEY: VARIANT
<222> LOCATION: (193)...(193)
<223> OTHER INFORMATION: Xaa = any amino acid

<400> SEQUENCE: 18

```
Met Ala Glu Ala Glu Ser Glu Asp Ser Glu Thr Thr Thr Pro Thr Thr
1               5                   10                  15
His His Leu Thr Ile Pro Pro Gly Leu Thr Gln Pro Glu Phe Gln Glu
            20                  25                  30
Leu Ala His Ser Ile Ser Glu Phe His Thr Tyr Gln Val Gly Pro Gly
        35                  40                  45
Gln Cys Ser Ser Leu Leu Ala Gln Arg Val His Ala Pro Leu Pro Thr
    50                  55                  60
Val Trp Ser Val Val Arg Arg Phe Asp Lys Pro Gln Thr Tyr Lys His
65                  70                  75                  80
Phe Ile Lys Ser Cys His Val Glu Asp Gly Phe Glu Met Arg Val Gly
                85                  90                  95
Cys Leu Arg Asp Val Asn Val Ile Ser Gly Leu Pro Ala Glu Thr Ser
            100                 105                 110
Thr Glu Arg Leu Asp Ile Leu Asp Asp Glu Arg His Val Thr Gly Phe
        115                 120                 125
Ser Ile Ile Gly Gly Glu His Arg Leu Arg Asn Tyr Arg Ser Val Thr
```

```
Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
        195
```

<210> SEQ ID NO 19
<211> LENGTH: 217
<212> TYPE: PRT
<213> ORGANISM: Medicago truncatula
<220> FEATURE:
<223> OTHER INFORMATION: barrel medic unknown protein, clone
    MTYFD_FE_FF_FG1G-N-24, GenBank Accession No. ACJ85026.1,
    GI:217073334

<400> SEQUENCE: 19

```
Met Glu Lys Ala Glu Ser Ser Thr Ala Ser Thr Ser Asp Gln Asp Ser
1               5                   10                  15

Asp Glu Asn His Arg Thr Gln His His Leu Thr Leu Pro Ser Gly Leu
                20                  25                  30

Arg Gln His Glu Phe Asp Ser Leu Ile Pro Phe Ile Asn Ser His His
            35                  40                  45

Thr Tyr Leu Ile Gly Pro Asn Gln Cys Ser Thr Leu Leu Ala Gln Arg
    50                  55                  60

Ile His Ala Pro Pro Gln Thr Val Trp Ser Val Val Arg Ser Phe Asp
65                  70                  75                  80

Lys Pro Gln Ile Tyr Lys His Ile Ile Lys Ser Cys Ser Leu Lys Glu
                85                  90                  95

Gly Phe Gln Met Lys Val Gly Cys Thr Arg Asp Val Asn Val Ile Ser
                100                 105                 110

Gly Leu Pro Ala Ala Thr Ser Thr Glu Arg Leu Asp Val Leu Asp Asp
            115                 120                 125

Glu Arg Arg Val Thr Gly Phe Ser Ile Ile Gly Gly Glu His Arg Leu
130                 135                 140

Lys Asn Tyr Arg Ser Val Thr Ser Val His Gly Phe Gly Asp Gly Asp
145                 150                 155                 160

Asn Gly Gly Glu Ile Trp Thr Val Val Leu Glu Ser Tyr Val Val Asp
                165                 170                 175

Val Pro Glu Gly Asn Thr Glu Glu Asp Thr Arg Leu Phe Ala Asp Thr
            180                 185                 190

Val Val Lys Leu Asn Leu Gln Lys Leu Ala Ser Val Thr Glu Gly Lys
        195                 200                 205

Asn Arg Asp Gly Asp Gly Lys Ser His
    210                 215
```

<210> SEQ ID NO 20
<211> LENGTH: 212
<212> TYPE: PRT
<213> ORGANISM: Oryza sativa
<220> FEATURE:
<223> OTHER INFORMATION: rice Japonica Group, cultivar Nipponbare,
    conserved hypothetical protein Os10g0573400, GenBank Accession No.
    NP_00106570.1, GI:115483600

<400> SEQUENCE: 20

```
Met Glu Gln Gln Glu Glu Val Pro Pro Pro Ala Gly Leu Gly Leu
 1               5                  10                  15

Thr Ala Glu Glu Tyr Ala Gln Val Arg Ala Thr Val Glu Ala His His
            20                  25                  30

Arg Tyr Ala Val Gly Pro Gly Gln Cys Ser Ser Leu Leu Ala Gln Arg
        35                  40                  45

Ile His Ala Pro Pro Ala Ala Val Trp Ala Val Val Arg Arg Phe Asp
50                  55                  60

Cys Pro Gln Val Tyr Lys His Phe Ile Arg Ser Cys Val Leu Arg Pro
65                  70                  75                  80

Asp Pro His His Asp Asp Asn Gly Asn Asp Leu Arg Pro Gly Arg Leu
                85                  90                  95

Arg Glu Val Ser Val Ile Ser Gly Leu Pro Ala Ser Thr Ser Thr Glu
                100                 105                 110

Arg Leu Asp Leu Leu Asp Asp Ala His Arg Val Phe Gly Phe Thr Ile
            115                 120                 125

Thr Gly Gly Glu His Arg Leu Arg Asn Tyr Arg Ser Val Thr Thr Val
    130                 135                 140

Ser Gln Leu Asp Glu Ile Cys Thr Leu Val Leu Glu Ser Tyr Ile Val
145                 150                 155                 160

Asp Val Pro Asp Gly Asn Thr Glu Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Pro Pro Pro Pro Pro
                195                 200                 205

Ala Ala Ala Glu
    210
```

<210> SEQ ID NO 21
<211> LENGTH: 212
<212> TYPE: PRT
<213> ORGANISM: Zea mays
<220> FEATURE:
<223> OTHER INFORMATION: maize cyclase/dehydrase family protein, clone
      306819, GenBank Accession No. ACG40002.1, GI:195641068

<400> SEQUENCE: 21

```
Met Asp Gln Gln Gly Ala Gly Gly Asp Ala Glu Val Pro Ala Gly Leu
 1               5                  10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
                100                 105                 110

Leu Asp Leu Leu Asp Asp Ala Ala Arg Val Phe Gly Phe Ser Ile Thr
            115                 120                 125

Gly Gly Glu His Arg Leu Arg Asn Tyr Arg Ser Val Thr Thr Val Ser
```

```
              130                 135                 140

Glu Leu Ala Val Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Ala Glu
                180                 185                 190

Ala Asn Ala Ala Glu Ala Ala Ala Thr Thr Asn Ser Val Leu Leu Pro
                195                 200                 205

Arg Pro Ala Glu
        210

<210> SEQ ID NO 22
<211> LENGTH: 212
<212> TYPE: PRT
<213> ORGANISM: Zea mays
<220> FEATURE:
<223> OTHER INFORMATION: maize cyclase/dehydrase family protein, clone
      241996, GenBank Accession No. ACG34473.1, GI:195625286
<220> FEATURE:
<221> NAME/KEY: VARIANT
<222> LOCATION: (11)...(11)
<223> OTHER INFORMATION: Xaa = any amino acid

<400> SEQUENCE: 22

Met Asp Gln Gln Gly Ala Gly Gly Asp Ala Xaa Val Pro Ala Gly Leu
  1               5                  10                  15

Gly Leu Thr Ala Ala Glu Tyr Glu Gln Leu Arg Ser Thr Val Asp Ala
                 20                  25                  30

His His Arg Tyr Ala Val Gly Glu Gly Gln Cys Ser Ser Leu Leu Ala
             35                  40                  45

Gln Arg Ile His Ala Pro Pro Glu Ala Val Trp Ala Val Val Arg Arg
     50                  55                  60

Phe Asp Cys Pro Gln Val Tyr Lys His Phe Ile Arg Ser Cys Ala Leu
 65                  70                  75                  80

Arg Pro Asp Pro Glu Ala Gly Asp Ala Leu Cys Pro Gly Arg Leu Arg
                 85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Asp Pro Ala Ile Cys Thr Val Val Leu Glu Ser Tyr Val
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Thr Glu
                180                 185                 190

Ala Asn Ala Ala Glu Ala Ala Ala Thr Thr Asn Ser Val Leu Leu Pro
                195                 200                 205

Arg Pro Ala Glu
        210

<210> SEQ ID NO 23
<211> LENGTH: 233
<212> TYPE: PRT
<213> ORGANISM: Vitis vinifera
```

<220> FEATURE:
<223> OTHER INFORMATION: wine grape cultivar PN40024 unnamed protein product, locus tag GSVIVT00032173001, GenBank Accession No. CAO43790.1, GI:157339249

<400> SEQUENCE: 23

```
Met Asp Pro His His His His Gly Leu Thr Glu Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
        35                  40                  45

Val Trp Pro Phe Val Arg Ser Phe Glu Asn Pro Gln Lys Tyr Lys His
    50                  55                  60

Phe Ile Lys Asp Cys Thr Met Arg Gly Asp Gly Val Gly Ser Ile
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
            180                 185                 190

Pro Ser Arg Glu Ile Ser Leu Gln Ser Glu Thr Glu Ser Ala Glu Arg
        195                 200                 205

Gly Asp Glu Arg Arg Asp Gly Asp Gly Pro Ser Lys Ala Cys Asn Arg
    210                 215                 220

Asn Glu Trp His Cys Thr Thr Lys Glu
225                 230
```

<210> SEQ ID NO 24
<211> LENGTH: 207
<212> TYPE: PRT
<213> ORGANISM: Oryza sativa
<220> FEATURE:
<223> OTHER INFORMATION: rice Japonica Group, cultivar Nipponbare, Bet v I allergen-like protein, gene P0495C02.29, clone P0495C02, GenBank Accession No. BAD25659.1, GI:49388537

<400> SEQUENCE: 24

```
Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
65                  70                  75                  80
```

Ser Cys Glu Leu Ala Ala Gly Asp Gly Ala Thr Val Gly Ser Val Arg
            85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
            115                 120                 125

Gly Gly Asp His Arg Leu Arg Asn Tyr Arg Ser Val Thr Ser Val Thr
            130                 135                 140

Glu Phe Ser Ser Pro Ser Ser Pro Pro Arg Pro Tyr Cys Val Val Val
145                 150                 155                 160

Glu Ser Tyr Val Val Asp Val Pro Glu Gly Asn Thr Glu Asp Thr
            165                 170                 175

Arg Met Phe Thr Asp Thr Val Val Lys Leu Asn Leu Gln Lys Leu Ala
            180                 185                 190

Ala Val Ala Thr Ser Ser Ser Pro Ala Ala Gly Asn His His
            195                 200                 205

<210> SEQ ID NO 25
<211> LENGTH: 210
<212> TYPE: PRT
<213> ORGANISM: Oryza sativa
<220> FEATURE:
<223> OTHER INFORMATION: rice Indica Group, cultivar 93-11, hypothetical
      protein OsI_06433, old locus tag OsI_006310, GLEAN gene, GenBank
      Accession No. EAY85077.1, GI:125538682

<400> SEQUENCE: 25

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
            35                  40                  45

Ser Leu Val Ala Gln Arg Val Asp Ala Pro Leu Ala Ala Val Trp Pro
        50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
            85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
            115                 120                 125

Gly Gly Asp His Arg Leu Arg Asn Tyr Arg Ser Val Thr Ser Val Thr
            130                 135                 140

Glu Phe Ser Ser Pro Ser Ser Pro Pro Ser Pro Arg Pro Tyr Cys
145                 150                 155                 160

Val Val Val Glu Ser Tyr Val Val Asp Val Pro Glu Gly Asn Thr Glu
            165                 170                 175

Glu Asp Thr Arg Met Phe Thr Asp Thr Val Val Lys Leu Asn Leu Gln
            180                 185                 190

Lys Leu Ala Ala Val Ala Thr Ser Ser Ser Pro Ala Ala Gly Asn
            195                 200                 205

His His
210

```
<210> SEQ ID NO 26
<211> LENGTH: 200
<212> TYPE: PRT
<213> ORGANISM: Zea mays
<220> FEATURE:
<223> OTHER INFORMATION: maize strain B73 unknown protein, clone
      ZM_BFb0151H07, GenBank Accession No. ACF82013.1, GI:194695858

<400> SEQUENCE: 26
```

Met Pro Tyr Thr Ala Pro Arg Pro Ser Pro Gln Gln His Ser Arg Val
 1               5                  10                  15

Leu Ser Gly Gly Gly Ala Lys Ala Ala Ser His Gly Ala Ser Cys Ala
             20                  25                  30

Ala Val Pro Ala Glu Val Ala Arg His His Glu His Ala Ala Arg Ala
         35                  40                  45

Gly Gln Cys Cys Ser Ala Val Val Gln Ala Ile Ala Ala Pro Val Gly
     50                  55                  60

Ala Val Trp Ser Val Val Arg Arg Phe Asp Arg Pro Gln Ala Tyr Lys
65                  70                  75                  80

His Phe Ile Arg Ser Cys Arg Leu Val Gly Gly Asp Val Ala Val
                 85                  90                  95

Gly Ser Val Arg Glu Val Arg Val Ser Gly Leu Pro Ala Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ala Asn Tyr Arg Ser Val
130                 135                 140

Thr Thr Val His Glu Ala Gly Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190

Ala Arg Thr Ala Glu Arg Leu Ala
        195                 200

```
<210> SEQ ID NO 27
<211> LENGTH: 215
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00037390001, GenBank Accession No.
      CAO48777.1, GI:157355387

<400> SEQUENCE: 27
```

Met Pro Ser Asn Pro Pro Lys Ser Ser Leu Val Val His Arg Ile Asn
 1               5                  10                  15

Ser Pro Asn Ser Ile Thr Thr Ala Thr Thr Ala Ser Ala Ala Ala Asn
             20                  25                  30

Asn His Asn Thr Ser Thr Met Pro His Lys Gln Val Pro Asp Ala
         35                  40                  45

Val Ser Arg His His Thr His Val Val Gly Pro Asn Gln Cys Cys Ser
    50                  55                  60

Ala Val Val Gln Gln Ile Ala Ala Pro Val Ser Thr Val Trp Ser Val
65                  70                  75                  80

Val Arg Arg Phe Asp Asn Pro Gln Ala Tyr Lys His Phe Val Lys Ser
                85                  90                  95

```
Cys His Val Val Val Gly Asp Gly Asp Val Gly Thr Leu Arg Glu Val
                100                 105                 110

His Val Ile Ser Gly Leu Pro Ala Ala Asn Ser Thr Glu Arg Leu Glu
            115                 120                 125

Ile Leu Asp Asp Glu Arg His Val Leu Ser Phe Ser Val Ile Gly Gly
        130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
                180                 185                 190

Val Arg Cys Asn Leu Gln Ser Leu Ala Gln Ile Ala Glu Asn Ala Ala
                195                 200                 205

Gly Cys Lys Arg Ser Ser Ser
            210             215

<210> SEQ ID NO 28
<211> LENGTH: 213
<212> TYPE: PRT
<213> ORGANISM: Nicotiana tabacum
<220> FEATURE:
<223> OTHER INFORMATION: tobacco hypothetical protein, gene c17, GenBank
      Accession No. CAI84653.1, GI:62867576

<400> SEQUENCE: 28

Met Pro Pro Ser Ser Pro Asp Ser Ser Val Leu Leu Gln Arg Ile Ser
 1               5                  10                  15

Ser Asn Thr Thr Pro Asp Phe Ala Cys Lys Gln Ser Gln Gln Leu Gln
            20                  25                  30

Arg Arg Thr Met Pro Ile Pro Cys Thr Thr Gln Val Pro Asp Ser Val
        35                  40                  45

Val Arg Phe His Thr His Pro Val Gly Pro Asn Gln Cys Cys Ser Ala
 50                 55                  60

Val Ile Gln Arg Ile Ser Ala Pro Val Ser Thr Val Trp Ser Val Val
 65                 70                  75                  80

Arg Arg Phe Asp Asn Pro Gln Ala Tyr Lys His Phe Val Lys Ser Cys
                85                  90                  95

His Val Ile Val Gly Asp Gly Asp Val Gly Thr Leu Arg Glu Val Arg
                100                 105                 110

Val Ile Ser Gly Leu Pro Ala Ala Ser Ser Thr Glu Arg Leu Glu Ile
            115                 120                 125

Leu Asp Asp Glu Arg His Val Ile Ser Phe Ser Val Val Gly Gly Asp
        130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
                180                 185                 190

Val Lys Cys Asn Leu Thr Ser Leu Ser Gln Ile Ala Val Asn Val Asn
                195                 200                 205

Arg Arg Lys Asp Ser
210

<210> SEQ ID NO 29
```

<211> LENGTH: 208
<212> TYPE: PRT
<213> ORGANISM: Oryza sativa
<220> FEATURE:
<223> OTHER INFORMATION: rice Indica Group, cultivar 93-11, hypothetical
      protein OsI_04285, old locus tag OsI_004197, GLEAN gene, GenBank
      Accession No. EAY76350.1, GI:125528236

<400> SEQUENCE: 29

Met Pro Tyr Ala Ala Val Arg Pro Ser Pro Pro Gln Leu Ser Arg
 1               5                  10                  15

Pro Ile Gly Ser Gly Ala Gly Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Cys Ser Thr Val Val Gln Ala Ile Ala Ala Pro Ala Asp Ala Val Trp
        50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
                115                 120                 125

Val Gly Gly Glu His Arg Leu Ala Asn Tyr Arg Ser Val Thr Thr Val
                130                 135                 140

His Glu Ala Ala Ala Pro Ala Met Ala Val Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
                180                 185                 190

Arg Leu Ala Pro Glu Ala Pro Arg Ala Asn Gly Ser Ile Asp His Ala
                195                 200                 205

<210> SEQ ID NO 30
<211> LENGTH: 208
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, gene B1088C09.11, clone B1088C09,
      GenBank Accession No. BAB68102.1, GI:15624049

<400> SEQUENCE: 30

Met Pro Tyr Ala Ala Val Arg Pro Ser Pro Pro Gln Leu Ser Arg
 1               5                  10                  15

Pro Ile Gly Ser Gly Ala Gly Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Phe Ser Thr Val Val Gln Ala Ile Ala Ala Pro Ala Asp Ala Val Trp
        50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

```
Arg Glu Val Arg Val Val Ser Gly Leu Pro Ala Thr Ser Ser Arg Glu
                100                 105                 110

Arg Leu Glu Val Leu Asp Asp Arg Val Leu Ser Phe Arg Ile
        115                 120                 125

Val Gly Gly Glu His Arg Leu Ala Asn Tyr Arg Ser Val Thr Thr Val
        130                 135                 140

His Glu Ala Ala Ala Pro Ala Met Ala Val Val Glu Ser Tyr Val
145                 150                 155                 160

Val Asp Val Pro Pro Gly Asn Thr Trp Glu Thr Arg Val Phe Val
                165                 170                 175

Asp Thr Ile Val Arg Cys Asn Leu Gln Ser Leu Ala Arg Thr Val Glu
        180                 185                 190

Arg Leu Ala Pro Glu Ala Pro Arg Ala Asn Gly Ser Ile Asp His Ala
        195                 200                 205
```

<210> SEQ ID NO 31
<211> LENGTH: 213
<212> TYPE: PRT
<213> ORGANISM: Picea sitchensis
<220> FEATURE:
<223> OTHER INFORMATION: Sitka spruce cultivar FB3-425, unknown protein,
      clone WS0276_P02, GenBank Accession No. ABK22940.1,
      GI:116783434

<400> SEQUENCE: 31

```
Met Asp Ile Ile Ala Gly Phe Asp Gln Leu Ser Phe Arg Leu Ser Gly
1               5                   10                  15

Ala Ser Lys Gln Ile Thr Lys Thr Gly Ala Val Gln Tyr Leu Lys Gly
            20                  25                  30

Glu Glu Gly Tyr Gly Glu Trp Leu Lys Glu Val Met Gly Arg Tyr His
        35                  40                  45

Tyr His Ser His Asp Gly Ala Arg Glu Cys Arg Cys Ser Ser Val Val
    50                  55                  60

Val Gln Gln Val Glu Ala Pro Val Ser Val Val Trp Ser Leu Val Arg
65                  70                  75                  80

Arg Phe Asp Gln Pro Gln Val Tyr Lys His Phe Val Ser Asn Cys Phe
                85                  90                  95

Met Arg Gly Asp Leu Lys Val Gly Cys Leu Arg Glu Val Arg Val Val
                100                 105                 110

Ser Gly Leu Pro Ala Ala Thr Ser Thr Glu Arg Leu Asp Ile Leu Asp
            115                 120                 125

Glu Glu Arg His Ile Leu Ser Phe Ser Ile Val Gly Gly Asp His Arg
        130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
                165                 170                 175

His Gly Asn Thr Lys Glu Glu Cys Leu Phe Val Asp Thr Ile Val
            180                 185                 190

Lys Cys Asn Leu Gln Ser Leu Ala His Val Ser Asn His Leu Asn Ser
        195                 200                 205

Thr His Arg Cys Leu
    210
```

<210> SEQ ID NO 32
<211> LENGTH: 207
<212> TYPE: PRT

<213> ORGANISM: Oryza sativa
<220> FEATURE:
<223> OTHER INFORMATION: rice Japonica Group, cultivar Nipponbare,
      hypothetical protein Os06g0562200, Bet v I allergen family
      protein, GenBank Accession No. NP_001057874.1, GI:115468550

<400> SEQUENCE: 32

```
Met Glu Ala His Val Glu Arg Ala Leu Arg Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                85                  90                  95

Thr Val Val Ser Gly Leu Pro Ala Ser Thr Ser Thr Glu Arg Leu Glu
            100                 105                 110

Met Leu Asp Asp Asp Arg His Ile Ile Ser Phe Arg Val Val Gly Gly
        115                 120                 125

Gln His Arg Leu Arg Asn Tyr Arg Ser Val Thr Ser Val Thr Glu Phe
    130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                165                 170                 175

Thr Arg Met Phe Thr Asp Thr Val Val Lys Leu Asn Leu Gln Met Leu
            180                 185                 190

Ala Ala Val Ala Glu Asp Ser Ser Ser Ala Ser Arg Arg Arg Asp
        195                 200                 205
```

<210> SEQ ID NO 33
<211> LENGTH: 216
<212> TYPE: PRT
<213> ORGANISM: Oryza sativa
<220> FEATURE:
<223> OTHER INFORMATION: rice Japonica Group, cultivar Nipponbare,
      hypothetical protein Os05g0473000, Streptomyces cyclase/dehydrase
      family protein, GenBank Accession No. NP_001055819.1, GI:115464439

<400> SEQUENCE: 33

```
Met Pro Tyr Thr Ala Pro Arg Pro Ser Pro Pro Gln His Ser Arg Ile
1               5                   10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                85                  90                  95

Gly Asp Gly Asp Gly Gly Ala Val Ala Val Gly Ser Val Arg Glu Val
            100                 105                 110
```

```
Arg Val Val Ser Gly Leu Pro Ala Thr Ser Ser Arg Glu Arg Leu Glu
            115                 120                 125

Ile Leu Asp Asp Glu Arg Arg Val Leu Ser Phe Arg Val Val Gly Gly
        130                 135                 140

Glu His Arg Leu Ser Asn Tyr Arg Ser Val Thr Thr Val His Glu Thr
145                 150                 155                 160

Ala Ala Gly Ala Ala Ala Val Val Glu Ser Tyr Val Val Asp
                165                 170                 175

Val Pro His Gly Asn Thr Ala Asp Glu Thr Arg Met Phe Val Asp Thr
                180                 185                 190

Ile Val Arg Cys Asn Leu Gln Ser Leu Ala Arg Thr Ala Glu Gln Leu
            195                 200                 205

Ala Leu Ala Ala Pro Arg Ala Ala
        210                 215

<210> SEQ ID NO 34
<211> LENGTH: 212
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00029365001, GenBank Accession No.
      CAO41436.1, GI:157351249

<400> SEQUENCE: 34

Met Pro Ser Ser Leu Gln Leu His Arg Ile Asn Asn Ile Asp Pro Thr
1               5                   10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
        35                  40                  45

Tyr His Ala His Ala Val Gly Pro His Gln Cys Cys Ser Met Val Val
    50                  55                  60

Gln Thr Thr Ala Ala Ala Leu Pro Thr Val Trp Ser Val Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
            100                 105                 110

Ser Gly Leu Pro Ala Glu Ser Ser Thr Glu Arg Leu Glu Ile Leu Asp
        115                 120                 125

Asp Glu Arg His Val Leu Ser Phe Ser Val Val Gly Gly Asp His Arg
    130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
            180                 185                 190

Asn Leu Gln Ser Leu Ala Gln Met Ser Glu Lys Leu Thr Asn Asn Asn
        195                 200                 205

Arg Asn Ser Ser
    210

<210> SEQ ID NO 35
<211> LENGTH: 218
```

```
<212> TYPE: PRT
<213> ORGANISM: Zea mays
<220> FEATURE:
<223> OTHER INFORMATION: maize cyclase/dehydrase family protein, clone
      1678999, GenBank Accession No. ACG30334.1, GI:195617008

<400> SEQUENCE: 35

Met Pro Cys Leu Gln Ala Ser Ser Pro Gly Ser Met Pro Tyr Gln His
1               5                   10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Gly Val Gly Thr
            100                 105                 110

Leu Arg Glu Val Arg Val Val Ser Gly Leu Pro Ala Ala Ser Ser Arg
        115                 120                 125

Glu Arg Leu Glu Val Leu Asp Asp Glu Ser His Val Leu Ser Phe Arg
    130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
        195                 200                 205

Thr Ala Glu Lys Leu Ala Leu Ala Ala Val
    210                 215

<210> SEQ ID NO 36
<211> LENGTH: 179
<212> TYPE: PRT
<213> ORGANISM: Physcomitrella patens
<220> FEATURE:
<223> OTHER INFORMATION: Physcomitrella patens subsp. patens bryophyte
      moss, ecotype Gransden 2004, hypothetical protein, predicted
      protein, locus tag PHYPADRAFT_222359, GenBank Accession No.
      XP_001778048.1, GI:168051209

<400> SEQUENCE: 36

Met Gln Thr Lys Gly Arg Gln Ala Asp Phe Gln Thr Leu Leu Glu Gly
1               5                   10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Gly Val Gly Ser
65                  70                  75                  80

Ile Arg Glu Val Arg Leu Val Ser Ser Ile Pro Ala Thr Ser Ser Ile
```

```
                    85                  90                  95
Glu Arg Leu Glu Ile Leu Asp Asp Glu Glu His Ile Ile Ser Phe Arg
                100                 105                 110

Val Leu Gly Gly Gly His Arg Leu Gln Asn Tyr Trp Ser Val Thr Ser
            115                 120                 125

Leu His Ser His Glu Ile Asp Gly Gln Met Gly Thr Leu Val Leu Glu
        130                 135                 140

Ser Tyr Val Val Asp Ile Pro Glu Gly Asn Thr Arg Glu Glu Thr His
145                 150                 155                 160

Met Phe Val Asp Thr Val Val Arg Cys Asn Leu Lys Ala Leu Ala Gln
                165                 170                 175

Val Ser Glu

<210> SEQ ID NO 37
<211> LENGTH: 229
<212> TYPE: PRT
<213> ORGANISM: Oryza sativa
<220> FEATURE:
<223> OTHER INFORMATION: rice Indica Group, cultivar 93-11, hypothetical
      protein OsI_11160, old locus tag OsI_010864, GLEAN gene, GenBank
      Accession No. EAY89631.1, GI:125543492

<400> SEQUENCE: 37

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Pro Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225

<210> SEQ ID NO 38
<211> LENGTH: 229
```

```
<212> TYPE: PRT
<213> ORGANISM: Oryza sativa
<220> FEATURE:
<223> OTHER INFORMATION: rice Japonica Group, cultivar Nipponbare,
      hypothetical protein Os03g0297600, Streptomyces cyclase/dehydrase
      family protein, GenBank Accession No. NP_001049838.1, GI:115452475

<400> SEQUENCE: 38

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225

<210> SEQ ID NO 39
<211> LENGTH: 205
<212> TYPE: PRT
<213> ORGANISM: Medicago truncatula
<220> FEATURE:
<223> OTHER INFORMATION: barrel medic unknown protein, clone
      MTYFP_FQ_FR_FS1G-H-19, GenBank Accession No. ACJ85898.1,
      GI:217075076

<400> SEQUENCE: 39

Met Pro Ser Pro Val Gln Phe Gln Arg Phe Asp Ser Asn Thr Ala Ile
1               5                   10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Val Arg Arg
```

```
                65                  70                  75                  80
Phe Asp Tyr Pro Gln Gly Tyr Lys His Phe Val Lys Ser Cys Asn Val
                    85                  90                  95

Val Ala Ser Gly Asp Gly Ile Arg Val Gly Ala Leu Arg Glu Val Arg
                    100                 105                 110

Leu Val Ser Gly Leu Pro Ala Val Ser Ser Thr Glu Arg Leu Asp Ile
                    115                 120                 125

Leu Asp Glu Glu Arg His Val Ile Ser Phe Ser Val Val Gly Gly Val
            130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                    165                 170                 175

Gly Asn Thr Lys Glu Glu Thr Cys Ser Phe Ala Asp Thr Ile Val Arg
                    180                 185                 190

Cys Asn Leu Gln Ser Leu Val Gln Ile Ala Glu Lys Leu
                    195                 200                 205

<210> SEQ ID NO 40
<211> LENGTH: 212
<212> TYPE: PRT
<213> ORGANISM: Zea mays
<220> FEATURE:
<223> OTHER INFORMATION: maize AT-rich element binding factor 3, clone
      1458362, GenBank Accession No. ACG26321.1, GI:195608982

<400> SEQUENCE: 40

Met Pro Phe Ala Ala Ser Arg Thr Ser Gln Gln Gln His Ser Arg Val
 1               5                  10                  15

Ala Thr Asn Gly Arg Ala Val Ala Val Cys Ala Gly His Ala Gly Val
                20                  25                  30

Pro Asp Glu Val Ala Arg His His Glu His Ala Val Ala Ala Gly Gln
            35                  40                  45

Cys Cys Ala Ala Met Val Gln Ser Ile Ala Ala Pro Val Asp Ala Val
50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                    85                  90                  95

Val Arg Glu Leu Leu Leu Val Ser Gly Leu Pro Ala Glu Ser Ser Arg
                    100                 105                 110

Glu Arg Leu Glu Ile Arg Asp Asp Glu Arg Arg Val Ile Ser Phe Arg
            115                 120                 125

Val Leu Gly Gly Asp His Arg Leu Ala Asn Tyr Arg Ser Val Thr Thr
            130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                    165                 170                 175

Thr Arg Ile Phe Val Asp Thr Ile Val Arg Cys Asn Leu Gln Ser Leu
                    180                 185                 190

Glu Gly Thr Val Ile Arg Gln Leu Glu Ile Ala Ala Met Pro His Asp
            195                 200                 205

Asp Asn Gln Asn
    210
```

```
<210> SEQ ID NO 41
<211> LENGTH: 233
<212> TYPE: PRT
<213> ORGANISM: Zea mays
<220> FEATURE:
<223> OTHER INFORMATION: maize strain B73 unknown protein, clone
      ZM_BFb0105O18, GenBank Accession No. ACF87013.1, GI:194705858

<400> SEQUENCE: 41

Met Arg Glu Arg Asn Ser Ser Ile Asp Gln Glu His Gln Arg Gly Ser
1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
65                  70                  75                  80

Pro Val Asp Ala Val Trp Ser Leu Val Arg Arg Phe Asp Gln Pro Gln
                85                  90                  95

Arg Tyr Lys Arg Phe Ile Arg Ser Cys His Leu Val Asp Gly Asp Gly
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230

<210> SEQ ID NO 42
<211> LENGTH: 194
<212> TYPE: PRT
<213> ORGANISM: Physcomitrella patens
<220> FEATURE:
<223> OTHER INFORMATION: Physcomitrella patens subsp. patens bryophyte
      moss, ecotype Gransden 2004, hypothetical protein, predicted
      protein, locus tag PHYPADRAFT_209242, GenBank Accession No.
      XP_001762113.1, GI:168019160

<400> SEQUENCE: 42

Met Met Gln Glu Lys Gln Gly Arg Pro Asp Phe Gln Phe Leu Leu Glu
1               5                   10                  15

Gly Gln Gln Asp Leu Ile Cys Arg Phe His Lys His Glu Leu Leu Pro
            20                  25                  30

His Gln Cys Gly Ser Ile Leu Leu Gln Gln Ile Lys Ala Pro Val Gln
        35                  40                  45

Thr Val Trp Leu Ile Val Arg Arg Phe Asp Glu Pro Gln Val Tyr Lys
```

```
                50                  55                  60
Arg Phe Ile Gln Arg Cys Asp Ile Val Glu Gly Asp Gly Val Gly
 65                  70                  75                  80

Ser Ile Arg Glu Val Gln Leu Val Ser Ser Ile Pro Ala Thr Ser Ser
                 85                  90                  95

Ile Glu Arg Leu Glu Ile Leu Asp Asp Glu Gly His Ile Ile Ser Phe
                100                 105                 110

Arg Val Leu Gly Gly Gly His Arg Leu Gln Asn Tyr Trp Ser Val Thr
                115                 120                 125

Ser Leu His Arg His Glu Ile Gln Gly Gln Met Gly Thr Leu Val Leu
            130                 135                 140

Glu Ser Tyr Val Val Asp Ile Pro Asp Gly Asn Thr Arg Glu Glu Thr
145                 150                 155                 160

His Thr Phe Val Asp Thr Val Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro

<210> SEQ ID NO 43
<211> LENGTH: 191
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00035869001, GenBank Accession No.
      CAO48052.1, GI:157354734

<400> SEQUENCE: 43

Met Lys Val Tyr Ser Pro Ser Gln Ile Leu Ala Glu Arg Gly Pro Arg
  1               5                  10                  15

Ala Gln Ala Met Gly Asn Leu Tyr His Thr His His Leu Leu Pro Asn
                 20                  25                  30

Gln Cys Ser Ser Leu Val Val Gln Thr Thr Asp Ala Pro Leu Pro Gln
             35                  40                  45

Val Trp Ser Met Val Arg Arg Phe Asp Arg Pro Gln Ser Tyr Lys Arg
 50                  55                  60

Phe Val Arg Gly Cys Thr Leu Arg Arg Gly Lys Gly Gly Val Gly Ser
 65                  70                  75                  80

Val Arg Glu Val Asn Ile Val Ser Gly Leu Pro Ala Glu Ile Ser Leu
                 85                  90                  95

Glu Arg Leu Asp Lys Leu Asp Asp Leu His Val Met Arg Phe Thr
                100                 105                 110

Val Ile Gly Gly Asp His Arg Leu Ala Asn Tyr His Ser Thr Leu Thr
            115                 120                 125

Leu His Glu Asp Glu Asp Gly Val Arg Lys Thr Val Val Met Glu
            130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190

<210> SEQ ID NO 44
<211> LENGTH: 217
```

-continued

```
<212> TYPE: PRT
<213> ORGANISM: Physcomitrella patens
<220> FEATURE:
<223> OTHER INFORMATION: Physcomitrella patens subsp. patens bryophyte
      moss, ecotype Gransden 2004, hypothetical protein, predicted
      protein, locus tag PHYPADRAFT_132509, GenBank Accession No.
      XP_001767821.1, GI:168030621

<400> SEQUENCE: 44

Met Gln Gln Val Lys Gly Arg Gln Asp Phe Gln Arg Leu Leu Glu Ala
 1               5                  10                  15

Gln Gln Asp Leu Ile Cys Arg Tyr His Thr His Glu Leu Lys Ala His
            20                  25                  30

Gln Cys Gly Ser Ile Leu Leu Gln Ile Lys Val Pro Leu Pro Ile
        35                  40                  45

Val Trp Ala Ile Val Arg Ser Phe Asp Lys Pro Gln Val Tyr Lys Arg
 50                  55                  60

Phe Ile Gln Thr Cys Lys Ile Thr Glu Gly Asp Gly Val Gly Ser
 65                  70                  75                  80

Ile Arg Glu Val His Leu Val Ser Ser Val Pro Ala Thr Cys Ser Ile
                 85                  90                  95

Glu Arg Leu Glu Ile Leu Asp Asp Glu Lys His Ile Ile Ser Phe Arg
            100                 105                 110

Val Leu Gly Gly Gly His Arg Leu Gln Asn Tyr Ser Ser Val Ser Ser
        115                 120                 125

Leu His Glu Leu Glu Val Glu Gly His Pro Cys Thr Leu Val Leu Glu
130                 135                 140

Ser Tyr Met Val Asp Ile Pro Asp Gly Asn Thr Arg Glu Glu Thr His
145                 150                 155                 160

Met Phe Val Asp Thr Val Val Arg Cys Asn Leu Lys Ser Leu Ala Gln
                165                 170                 175

Ile Ser Glu Gln Gln Tyr Asn Lys Asp Cys Leu Gln Gln Lys Gln His
            180                 185                 190

Asp Gln Gln Gln Met Tyr Gln Gln Arg His Pro Pro Leu Pro Pro Ile
        195                 200                 205

Pro Ile Thr Asp Lys Asn Met Glu Arg
    210                 215

<210> SEQ ID NO 45
<211> LENGTH: 195
<212> TYPE: PRT
<213> ORGANISM: Physcomitrella patens
<220> FEATURE:
<223> OTHER INFORMATION: Physcomitrella patens subsp. patens bryophyte
      moss, ecotype Gransden 2004, hypothetical protein, predicted
      protein, locus tag PHYPADRAFT_213389, GenBank Accession No.
      XP_001767012.1, GI:168028995

<400> SEQUENCE: 45

Met Arg Phe Asp Ile Gly His Asn Asp Val Arg Gly Phe Phe Thr Cys
 1               5                  10                  15

Glu Glu Glu His Ala Tyr Ala Leu His Ser Gln Thr Val Glu Leu Asn
            20                  25                  30

Gln Cys Gly Ser Ile Leu Met Gln Gln Ile His Ala Pro Ile Glu Val
        35                  40                  45

Val Trp Ser Ile Val Arg Ser Phe Gly Ser Pro Gln Ile Tyr Lys Lys
 50                  55                  60

Phe Ile Gln Ala Cys Ile Leu Thr Val Gly Asp Gly Gly Val Gly Ser
 65                  70                  75                  80
```

```
Ile Arg Glu Val Phe Leu Val Ser Gly Val Pro Ala Thr Ser Ser Ile
                85                  90                  95

Glu Arg Leu Glu Ile Leu Asp Asp Glu Lys His Val Phe Ser Phe Arg
            100                 105                 110

Val Leu Lys Gly Gly His Arg Leu Gln Asn Tyr Arg Ser Val Thr Thr
        115                 120                 125

Leu His Glu Gln Glu Val Asn Gly Arg Gln Thr Thr Thr Val Leu Glu
    130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195

<210> SEQ ID NO 46
<211> LENGTH: 172
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004947, GenBank
      Accession No. CAN72620.1, GI:147840019

<400> SEQUENCE: 46

Met Gly Asn Leu Tyr His Thr His His Leu Leu Pro Asn Gln Cys Ser
 1               5                  10                  15

Ser Leu Val Val Gln Thr Thr Asp Ala Pro Leu Pro Gln Val Trp Ser
            20                  25                  30

Met Val Arg Arg Phe Asp Arg Pro Gln Ser Tyr Lys Arg Phe Val Arg
        35                  40                  45

Gly Cys Thr Leu Arg Arg Gly Lys Gly Val Gly Ser Val Arg Glu
    50                  55                  60

Val Asn Ile Val Ser Gly Leu Pro Ala Glu Ile Ser Leu Glu Arg Leu
65                  70                  75                  80

Asp Lys Leu Asp Asp Asp Leu His Val Met Arg Phe Thr Val Ile Gly
                85                  90                  95

Gly Asp His Arg Leu Ala Asn Tyr His Ser Thr Leu Thr Leu His Glu
            100                 105                 110

Asp Glu Glu Asp Gly Val Arg Lys Thr Val Val Met Glu Ser Tyr Val
        115                 120                 125

Val Asp Val Pro Gly Gly Asn Ser Ala Gly Glu Thr Cys Tyr Phe Ala
    130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170

<210> SEQ ID NO 47
<211> LENGTH: 196
<212> TYPE: PRT
<213> ORGANISM: Picea sitchensis
<220> FEATURE:
<223> OTHER INFORMATION: Sitka spruce cultivar FB3-425, unknown protein,
      clone WS0281_I24, GenBank Accession No. ABK23752.1,
      GI:116785512
```

<400> SEQUENCE: 47

```
Met Glu Asp Leu Ser Ser Trp Arg Glu Gly Arg Ala Met Trp Leu Gly
 1               5                   10                  15

Asn Pro Pro Ser Glu Ser Glu Leu Val Cys Arg His His Arg His Glu
             20                  25                  30

Leu Gln Gly Asn Gln Cys Ser Ser Phe Leu Val Lys His Ile Arg Ala
         35                  40                  45

Pro Val His Leu Val Trp Ser Ile Val Arg Thr Phe Asp Gln Pro Gln
     50                  55                  60

Lys Tyr Lys Pro Phe Val His Ser Cys Ser Val Arg Gly Gly Ile Thr
 65                  70                  75                  80

Val Gly Ser Ile Arg Asn Val Asn Val Lys Ser Gly Leu Pro Ala Thr
                 85                  90                  95

Ala Ser Glu Glu Arg Leu Glu Ile Leu Asp Asp Asn Glu His Val Phe
            100                 105                 110

Ser Ile Lys Ile Leu Gly Gly Asp His Arg Leu Gln Asn Tyr Ser Ser
        115                 120                 125

Ile Ile Thr Val His Pro Glu Ile Ile Asp Gly Arg Pro Gly Thr Leu
130                 135                 140

Val Ile Glu Ser Tyr Val Val Asp Val Pro Glu Gly Asn Thr Arg Glu
145                 150                 155                 160

Glu Thr Arg Phe Phe Val Glu Ala Leu Val Lys Cys Asn Leu Lys Ser
                165                 170                 175

Leu Ala Asp Val Ser Glu Arg Leu Ala Ser Gln His His Thr Glu Leu
            180                 185                 190

Leu Glu Arg Thr
        195
```

<210> SEQ ID NO 48
<211> LENGTH: 185
<212> TYPE: PRT
<213> ORGANISM: Solanum tuberosum
<220> FEATURE:
<223> OTHER INFORMATION: potato cultivar Kuras, CAPIP1-like protein, clone 153D02, similar to Capsicum annuum CAPIP1, GenBank Accession No. ABB29920.1, GI:78191398

<400> SEQUENCE: 48

```
Met Asn Ala Asn Gly Phe Cys Gly Val Glu Lys Glu Tyr Ile Arg Lys
 1               5                   10                  15

His His Leu His Glu Pro Lys Leu Asn Gln Cys Ser Ser Phe Leu Val
             20                  25                  30

Lys His Ile Arg Ala Pro Val His Leu Val Trp Ser Leu Val Arg Arg
         35                  40                  45

Phe Asp Gln Pro Gln Lys Tyr Lys Pro Phe Ile Ser Arg Cys Ile Val
     50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Leu Ser Val Arg Ile Val Gly Gly Asp His Arg Leu
            100                 105                 110

Arg Asn Tyr Ser Ser Val Ile Ser Val His Pro Glu Val Ile Asp Gly
        115                 120                 125

Arg Pro Gly Thr Val Val Leu Glu Ser Phe Val Val Asp Val Pro Glu
```

```
            130                 135                 140
Gly Asn Thr Lys Asp Glu Thr Cys Tyr Phe Val Glu Ala Leu Ile Asn
145                 150                 155                 160

Cys Asn Leu Lys Ser Leu Ala Asp Ile Ser Glu Arg Val Ala Val Gln
                165                 170                 175

Asp Arg Thr Glu Pro Ile Asp Gln Val
            180                 185
```

<210> SEQ ID NO 49
<211> LENGTH: 190
<212> TYPE: PRT
<213> ORGANISM: Medicago truncatula
<220> FEATURE:
<223> OTHER INFORMATION: barrel medic unknown protein, clone
      MTYFP_FQ_FR_FS1G-E-17, GenBank Accession No. ACJ85952.1,
      GI:217075184

<400> SEQUENCE: 49

```
Met Asn Asn Gly Cys Glu Gln Gln Gln Tyr Ser Val Ile Glu Thr Gln
  1               5                  10                  15

Tyr Ile Arg Arg His His Lys His Asp Leu Arg Asp Asn Gln Cys Ser
                 20                  25                  30

Ser Ala Leu Val Lys His Ile Lys Ala Pro Val His Leu Val Trp Ser
             35                  40                  45

Leu Val Arg Arg Phe Asp Gln Pro Gln Lys Tyr Lys Pro Phe Ile Ser
         50                  55                  60

Arg Cys Ile Met Gln Gly Asp Leu Ser Ile Gly Ser Val Arg Glu Val
 65                  70                  75                  80

Asn Val Lys Ser Gly Leu Pro Ala Thr Thr Ser Thr Glu Arg Leu Glu
                 85                  90                  95

Gln Leu Asp Asp Glu Glu His Ile Leu Gly Ile Arg Ile Val Gly Gly
                100                 105                 110

Asp His Arg Leu Arg Asn Tyr Ser Ser Ile Ile Thr Val His Pro Gly
            115                 120                 125

Val Ile Asp Gly Arg Pro Gly Thr Met Val Ile Glu Ser Phe Val Val
        130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Leu Ala Asp Val Ser Glu Arg
                165                 170                 175

Met Ala Val Gln Gly Arg Thr Asp Pro Ile Asn Ile Asn Pro
            180                 185                 190
```

<210> SEQ ID NO 50
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00002440001, GenBank Accession No.
      CAO65816.1, GI:157358179

<400> SEQUENCE: 50

```
Met Ser Gly Tyr Gly Cys Ile Lys Met Glu Asp Glu Tyr Ile Arg Arg
  1               5                  10                  15

His His Arg His Glu Ile Arg Asp Asn Gln Cys Ser Ser Ser Leu Val
                 20                  25                  30

Lys His Ile Lys Ala Pro Val His Leu Val Trp Ser Leu Val Arg Ser
             35                  40                  45
```

```
Phe Asp Gln Pro Gln Lys Tyr Lys Pro Phe Val Ser Arg Cys Ile Val
 50                  55                  60

Gln Gly Asp Leu Glu Ile Gly Ser Val Arg Glu Val Asn Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Phe Gly Met Arg Ile Val Gly Gly Asp His Arg Leu
                100                 105                 110

Lys Asn Tyr Ser Ser Ile Val Thr Val His Pro Glu Ile Ile Asp Gly
                115                 120                 125

Arg Pro Gly Thr Leu Val Ile Glu Ser Phe Val Val Asp Val Pro Asp
            130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 51
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00006507001, GenBank Accession No.
      CAO69376.1, GI:157360187

<400> SEQUENCE: 51

Met Asn Gly Asn Gly Leu Ser Ser Met Glu Ser Glu Tyr Ile Arg Arg
 1                   5                  10                  15

His His Arg His Glu Pro Ala Glu Asn Gln Cys Ser Ser Ala Leu Val
                 20                  25                  30

Lys His Ile Lys Ala Pro Val Pro Leu Val Trp Ser Leu Val Arg Arg
             35                  40                  45

Phe Asp Gln Pro Gln Lys Tyr Lys Pro Phe Ile Ser Arg Cys Val Val
 50                  55                  60

Gln Gly Asn Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Asp Glu His Ile Leu Ser Met Arg Ile Ile Gly Gly Asp His Arg Leu
                100                 105                 110

Arg Asn Tyr Ser Ser Ile Ile Ser Leu His Pro Glu Ile Ile Asp Gly
                115                 120                 125

Arg Pro Gly Thr Met Val Ile Glu Ser Tyr Val Val Asp Val Pro Glu
            130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185

<210> SEQ ID NO 52
<211> LENGTH: 208
```

```
<212> TYPE: PRT
<213> ORGANISM: Oryza sativa
<220> FEATURE:
<223> OTHER INFORMATION: rice Japonica Group, cultivar Nipponbare,
      hypothetical protein OsJ_21703, old locus tag OsJ_020847, GLEAN
      gene, GenBank Accession No. EAZ37364.1, GI:125597584

<400> SEQUENCE: 52

Met Glu Ala His Val Glu Arg Ala Leu Arg Glu Gly Leu Thr Glu Glu
 1               5                  10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
            100                 105                 110

Glu Met Leu Asp Asp Asp Arg His Ile Ile Ser Phe Arg Val Val Gly
        115                 120                 125

Gly Gln His Arg Leu Arg Asn Tyr Arg Ser Val Thr Ser Val Thr Glu
    130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
                165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ala Ser Arg Arg Arg Asp
        195                 200                 205

<210> SEQ ID NO 53
<211> LENGTH: 186
<212> TYPE: PRT
<213> ORGANISM: Capsicum annuum
<220> FEATURE:
<223> OTHER INFORMATION: pepper cultivar hanbyul, CAPIP1 protein,
      GenBank Accession No. AAT35532.1, GI:47558817

<400> SEQUENCE: 53

Met Met Asn Ala Asn Gly Phe Ser Gly Val Glu Lys Glu Tyr Ile Arg
 1               5                  10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110
```

```
Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
        130                 135                 140

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
        180                 185
```

<210> SEQ ID NO 54
<211> LENGTH: 186
<212> TYPE: PRT
<213> ORGANISM: Populus trichocarpa
<220> FEATURE:
<223> OTHER INFORMATION: California poplar (Western balsam poplar, black cottonwood) cultivar 383-2499 (Nisqually-1), unknown protein, clone PX0011_1113, GenBank Accession No. ABK92491.1, GI:118481075

<400> SEQUENCE: 54

```
Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
                20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
        130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
        180                 185
```

<210> SEQ ID NO 55
<211> LENGTH: 185
<212> TYPE: PRT
<213> ORGANISM: Capsicum annuum
<220> FEATURE:
<223> OTHER INFORMATION: pepper cultivar hanbyul, PIP1 protein, GenBank Accession No. ABF72432.1, GI:104304209

<400> SEQUENCE: 55

```
Met Asn Ala Asn Gly Phe Ser Val Glu Lys Glu Tyr Ile Arg Lys
1               5                   10                  15
```

```
His His Leu His Gln Pro Lys Glu Asn Gln Cys Ser Ser Phe Leu Val
            20                  25                  30

Lys His Ile Arg Ala Pro Val His Leu Val Trp Ser Leu Val Arg Arg
            35                  40                  45

Phe Asp Gln Pro Gln Lys Tyr Lys Pro Phe Val Ser Arg Cys Ile Ala
 50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Leu Ser Phe Arg Ile Ile Gly Gly Asp His Arg Leu
                100                 105                 110

Arg Asn Tyr Ser Ser Ile Ile Ser Leu His Pro Glu Val Ile Asp Gly
            115                 120                 125

Arg Pro Gly Thr Leu Val Ile Glu Ser Phe Val Val Asp Val Pro Gln
            130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
                180                 185

<210> SEQ ID NO 56
<211> LENGTH: 186
<212> TYPE: PRT
<213> ORGANISM: Populus trichocarpa x Populus deltoides
<220> FEATURE:
<223> OTHER INFORMATION: California poplar (Western balsam poplar,
      black cottonwood) x Eastern cottonwood, cultivar H11-11, unknown
      protein, clone WS0133_I04, GenBank Accession No. ABK96505.1,
      GI:118489403

<400> SEQUENCE: 56

Met Asn Gly Ser Asp Ala Tyr Ser Ala Thr Glu Ala Gln Tyr Val Arg
 1                5                  10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
            35                  40                  45

Arg Phe Asp Gln Pro Gln Arg Tyr Lys Pro Phe Val Ser Arg Cys Val
 50                  55                  60

Met Asn Gly Glu Leu Gly Ile Gly Ser Val Arg Glu Val Asn Val Lys
 65                  70                  75                  80

Ser Gly Leu Pro Ala Thr Thr Ser Thr Glu Arg Leu Glu Leu Leu Asp
                 85                  90                  95

Asp Glu Glu His Ile Leu Gly Val Gln Ile Val Gly Gly Asp His Arg
                100                 105                 110

Leu Lys Asn Tyr Ser Ser Ile Met Thr Val His Pro Glu Phe Ile Asp
            115                 120                 125

Gly Arg Pro Gly Thr Leu Val Ile Glu Ser Phe Ile Val Asp Val Pro
            130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175
```

Gln Asp Arg Val Glu Pro Val Asn Gln Phe
            180                 185

<210> SEQ ID NO 57
<211> LENGTH: 188
<212> TYPE: PRT
<213> ORGANISM: Pisum sativum
<220> FEATURE:
<223> OTHER INFORMATION: pea AT-rich element binding factor 3 (PsATF,
      ATF3), potential transcription factor for PsCHS1, GenBank
      Accession No. AAV85853.1, GI:56384584

<400> SEQUENCE: 57

Met Asn Asn Gly Gly Glu Gln Tyr Ser Ala Ile Glu Thr Gln Tyr Ile
1               5                   10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175

Val Gln Gly Arg Thr Asp Pro Ile Asn Val Asn Pro
            180                 185

<210> SEQ ID NO 58
<211> LENGTH: 177
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00027009001, GenBank Accession No.
      CAO39744.1, GI:157349888

<400> SEQUENCE: 58

Met Glu Ala Gln Val Ile Cys Arg His His Ala His Glu Pro Arg Glu
1               5                   10                  15

Asn Gln Cys Ser Ser Val Leu Val Arg His Val Lys Ala Pro Ala Asn
            20                  25                  30

Leu Val Trp Ser Leu Val Arg Arg Phe Asp Gln Pro Gln Lys Tyr Lys
        35                  40                  45

Pro Phe Val Ser Arg Cys Val Val Gln Gly Asp Leu Arg Ile Gly Ser
    50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Asp Glu His Val Leu Gly Ile Lys

```
                    85                  90                  95
Ile Leu Asp Gly Asp His Arg Leu Arg Asn Tyr Ser Ser Val Ile Thr
            100                 105                 110

Val His Pro Glu Ile Ile Asp Gly Arg Pro Gly Thr Leu Val Ile Glu
        115                 120                 125

Ser Phe Val Val Asp Val Pro Glu Gly Asn Thr Lys Asp Asp Thr Cys
    130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala
                165                 170                 175

Val

<210> SEQ ID NO 59
<211> LENGTH: 178
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004915, GenBank
      Accession No. CAN82501.1, GI:147856414

<400> SEQUENCE: 59

Met Met Glu Ala Gln Val Ile Cys Arg His His Ala His Glu Pro Arg
1               5                   10                  15

Glu Asn Gln Cys Ser Ser Val Leu Val Arg His Val Lys Ala Pro Ala
            20                  25                  30

Asn Leu Val Trp Ser Leu Val Arg Arg Phe Asp Gln Pro Gln Lys Tyr
        35                  40                  45

Lys Pro Phe Val Ser Arg Cys Val Val Gln Gly Asp Leu Arg Ile Gly
    50                  55                  60

Ser Val Arg Glu Val Asn Val Lys Thr Gly Leu Pro Ala Thr Thr Ser
65                  70                  75                  80

Thr Glu Arg Leu Glu Leu Phe Asp Asp Asp Glu His Val Leu Gly Ile
                85                  90                  95

Lys Ile Leu Asp Gly Asp His Arg Leu Arg Asn Tyr Ser Ser Val Ile
            100                 105                 110

Thr Val His Pro Glu Ile Ile Asp Gly Arg Pro Gly Thr Leu Val Ile
        115                 120                 125

Glu Ser Phe Val Val Asp Val Pro Glu Gly Asn Thr Lys Asp Asp Thr
    130                 135                 140

Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val

<210> SEQ ID NO 60
<211> LENGTH: 193
<212> TYPE: PRT
<213> ORGANISM: Arachis hypogaea
<220> FEATURE:
<223> OTHER INFORMATION: peanut pathogenesis-induced protein (PIP),
      GenBank Accession No. ACG76109.1, GI:196196276
<220> FEATURE:
<221> NAME/KEY: VARIANT
<222> LOCATION: (162)...(162)
<223> OTHER INFORMATION: Xaa = any amino acid
```

-continued

```
<400> SEQUENCE: 60

Met Met Asn Gly Ser Cys Gly Gly Gly Gly Glu Ala Tyr Gly
1               5                   10                  15

Ala Ile Glu Ala Gln Tyr Ile Arg Arg His His Arg His Glu Pro Arg
            20                  25                  30

Asp Asn Gln Cys Thr Ser Ala Leu Val Lys His Ile Arg Ala Pro Val
        35                  40                  45

His Leu Val Trp Ser Leu Val Arg Arg Phe Asp Gln Pro Gln Lys Tyr
    50                  55                  60

Lys Pro Phe Val Ser Arg Cys Ile Met Gln Gly Asp Leu Gly Ile Gly
65                  70                  75                  80

Ser Val Arg Glu Val Asn Val Lys Ser Gly Leu Pro Ala Thr Thr Ser
                85                  90                  95

Thr Glu Arg Leu Glu Gln Leu Asp Asp Glu His Ile Leu Gly Ile
            100                 105                 110

Arg Ile Val Gly Gly Asp His Arg Leu Arg Asn Tyr Ser Ser Ile Ile
        115                 120                 125

Thr Val His Pro Glu Val Ile Glu Gly Arg Pro Gly Thr Met Val Ile
    130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
            180                 185                 190

Gln

<210> SEQ ID NO 61
<211> LENGTH: 217
<212> TYPE: PRT
<213> ORGANISM: Zea mays
<220> FEATURE:
<223> OTHER INFORMATION: maize AT-rich element binding factor 3, clone
      300908, GenBank Accession No. ACG39386.1, GI:195639836

<400> SEQUENCE: 61

Met Val Val Glu Met Asp Gly Gly Val Gly Val Ala Ala Gly Gly Gly
1               5                   10                  15

Gly Gly Ala Gln Thr Pro Ala Pro Ala Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Asn Tyr Ser Ser Ile Leu Thr Val His Pro Glu Val Ile Asp
```

```
                 145                 150                 155                 160
Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
                180                 185                 190

Lys Cys Asn Leu Arg Ser Leu Ala Glu Val Ser Glu Gly Gln Val Ile
                195                 200                 205

Met Asp Gln Thr Glu Pro Leu Asp Arg
                210                 215

<210> SEQ ID NO 62
<211> LENGTH: 217
<212> TYPE: PRT
<213> ORGANISM: Zea mays
<220> FEATURE:
<223> OTHER INFORMATION: maize strain B73, unknown protein, clone
      ZM_BFb0036A01, GenBank Accession No. ACF80077.1, GI:194691986

<400> SEQUENCE: 62

Met Val Val Glu Met Asp Gly Gly Val Gly Val Ala Ala Ala Gly Gly
 1               5                  10                  15

Gly Gly Ala Gln Thr Pro Ala Pro Pro Pro Arg Arg Trp Arg Leu
                20                  25                  30

Ala Asp Glu Arg Cys Asp Leu Arg Ala Met Glu Thr Asp Tyr Val Arg
                35                  40                  45

Arg Phe His Arg His Glu Pro Arg Asp His Gln Cys Ser Ser Ala Val
             50                 55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
                100                 105                 110

Ser Gly Leu Pro Ala Thr Arg Ser Thr Glu Arg Leu Glu Leu Leu Asp
                115                 120                 125

Asp Asp Glu Arg Ile Leu Ser Val Arg Phe Val Gly Asp His Arg
                130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
                180                 185                 190

Lys Cys Asn Leu Arg Ser Leu Ala Glu Val Ser Glu Gly Gln Val Ile
                195                 200                 205

Met Asp Gln Thr Glu Pro Leu Asp Arg
                210                 215

<210> SEQ ID NO 63
<211> LENGTH: 206
<212> TYPE: PRT
<213> ORGANISM: Oryza sativa
<220> FEATURE:
<223> OTHER INFORMATION: rice Japonica Group, cultivar Nipponbare,
      conserved hypothetical protein Os06g0528300, GenBank Accession No.
      NP_001057772.1, GI:115468346

<400> SEQUENCE: 63
```

```
Met Asn Gly Val Gly Gly Ala Gly Gly Ala Ala Ala Gly Lys Leu Pro
  1               5                  10                  15

Met Val Ser His Arg Arg Val Gln Trp Arg Leu Ala Asp Glu Arg Cys
             20                  25                  30

Glu Leu Arg Glu Glu Met Glu Tyr Ile Arg Arg Phe His Arg His
         35                  40                  45

Glu Pro Ser Ser Asn Gln Cys Thr Ser Phe Ala Ala Lys His Ile Lys
 50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
             85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
            115                 120                 125

Ile Leu Lys Val Asn Phe Ile Gly Gly Asp His Met Leu Lys Asn Tyr
        130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 64
<211> LENGTH: 206
<212> TYPE: PRT
<213> ORGANISM: Oryza sativa
<220> FEATURE:
<223> OTHER INFORMATION: rice Indica Group, cultivar 93-11, hypothetical
      protein OsI_23215, old locus tag OsI_022420, GLEAN gene, GenBank
      Accession No. EAZ01188.1, GI:125555582

<400> SEQUENCE: 64

Met Asn Gly Ala Gly Gly Ala Gly Gly Ala Ala Ala Gly Lys Leu Pro
  1               5                  10                  15

Met Val Ser His Arg Gln Val Gln Trp Arg Leu Ala Asp Glu Arg Cys
             20                  25                  30

Glu Leu Arg Glu Glu Met Glu Tyr Ile Arg Gln Phe His Arg His
         35                  40                  45

Glu Pro Ser Ser Asn Gln Cys Thr Ser Phe Val Ala Lys His Ile Lys
 50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
             85                  90                  95

Ile Ala Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
            115                 120                 125

Ile Leu Lys Val Lys Phe Ile Gly Gly Asp His Met Leu Lys Asn Tyr
        130                 135                 140

Ser Ser Ile Leu Thr Ile His Ser Glu Val Ile Asp Gly Gln Leu Gly
```

```
                145                 150                 155                 160
Thr Leu Val Val Glu Ser Phe Val Val Asp Ile Pro Glu Gly Asn Thr
                    165                 170                 175

Lys Asp Asp Ile Cys Tyr Phe Ile Glu Asn Ile Leu Arg Cys Asn Leu
                    180                 185                 190

Met Thr Leu Ala Asp Val Ser Glu Glu Arg Leu Ala Asn Pro
                    195                 200                 205

<210> SEQ ID NO 65
<211> LENGTH: 205
<212> TYPE: PRT
<213> ORGANISM: Oryza sativa
<220> FEATURE:
<223> OTHER INFORMATION: rice Japonica Group, cultivar Nipponbare,
      hypothetical protein OsJ_06125, old locus tag OsI_005939, GenBank
      Accession No. EAZ22456.1, GI:125581525

<400> SEQUENCE: 65

Met Val Glu Val Gly Gly Gly Ala Ala Glu Ala Ala Ala Gly Arg Arg
1               5                   10                  15

Trp Arg Leu Ala Asp Glu Arg Cys Asp Leu Arg Ala Ala Glu Thr Glu
                20                  25                  30

Tyr Val Arg Arg Phe His Arg Glu Pro Arg Asp His Gln Cys Ser
                35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
                100                 105                 110

Leu Leu Asp Asp Asn Glu His Ile Leu Ser Val Arg Phe Val Gly Gly
                115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
                180                 185                 190

Leu Val Cys Gln Gly Pro Asn Arg Ala Pro Ser Thr Arg
                195                 200                 205

<210> SEQ ID NO 66
<211> LENGTH: 204
<212> TYPE: PRT
<213> ORGANISM: Oryza sativa
<220> FEATURE:
<223> OTHER INFORMATION: rice Japonica Group, cultivar Nipponbare,
      hypothetical protein Os02g0255500, similar to extensin (fragment),
      GenBank Accession No. NP_001046464.1, GI:115445369

<400> SEQUENCE: 66

Met Val Glu Val Gly Gly Gly Ala Ala Glu Ala Ala Ala Gly Arg Arg
1               5                   10                  15

Trp Arg Leu Ala Asp Glu Arg Cys Asp Leu Arg Ala Ala Glu Thr Glu
                20                  25                  30
```

Tyr Val Arg Arg Phe His Arg His Glu Pro Arg Asp His Gln Cys Ser
                35                  40                  45

Ser Ala Val Ala Lys His Ile Lys Ala Pro Val His Leu Val Trp Ser
 50                  55                  60

Leu Val Arg Arg Phe Asp Gln Pro Gln Leu Phe Lys Pro Phe Val Ser
 65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
                100                 105                 110

Leu Leu Asp Asp Asn Glu His Ile Leu Ser Val Arg Phe Val Gly Gly
                115                 120                 125

Asp His Arg Leu Lys Asn Tyr Ser Ser Ile Leu Thr Val His Pro Glu
 130                 135                 140

Val Ile Asp Gly Arg Pro Gly Thr Leu Val Ile Glu Ser Phe Val Val
145                  150                 155                 160

Asp Val Pro Glu Gly Asn Thr Lys Asp Glu Thr Cys Tyr Phe Val Glu
                165                 170                 175

Ala Leu Leu Lys Cys Asn Leu Ser Leu Ala Glu Val Ser Glu Arg
                180                 185                 190

Leu Val Val Lys Asp Gln Thr Glu Pro Leu Asp Arg
                195                 200

<210> SEQ ID NO 67
<211> LENGTH: 199
<212> TYPE: PRT
<213> ORGANISM: Medicago truncatula
<220> FEATURE:
<223> OTHER INFORMATION: barrel medic unknown protein, clone
      MTYFP_FQ_FR_FS1G-G-11, GenBank Accession No. ACJ86004.1,
      GI:217075288

<400> SEQUENCE: 67

Met Glu Lys Met Asn Gly Thr Glu Asn Asn Gly Val Phe Asn Ser Thr
 1                   5                  10                  15

Glu Met Glu Tyr Ile Arg Arg His His Asn Gln Gln Pro Gly Glu Asn
                20                  25                  30

Gln Cys Ser Ser Ala Leu Val Lys His Ile Arg Ala Pro Val Pro Leu
                35                  40                  45

Val Trp Ser Leu Val Arg Arg Phe Asp Gln Pro Gln Lys Tyr Lys Pro
 50                  55                  60

Phe Val Ser Arg Cys Val Val Arg Gly Asn Leu Glu Ile Gly Ser Leu
 65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
                100                 105                 110

Ile Gly Gly Asp His Arg Leu Arg Asn Tyr Ser Ser Ile Met Ser Leu
                115                 120                 125

His Pro Glu Ile Ile Asp Gly Arg Pro Gly Thr Leu Val Ile Glu Ser
 130                 135                 140

Phe Val Val Asp Val Pro Glu Gly Asn Thr Lys Asp Glu Thr Cys Tyr
145                  150                 155                 160

Phe Val Glu Ala Leu Ile Lys Cys Asn Leu Lys Ser Leu Ser Asp Val
                165                 170                 175

```
Ser Glu Gly His Ala Val Gln Asp Leu Thr Glu Pro Leu Asp Arg Val
            180                 185                 190

His Glu Leu Leu Ile Ser Gly
        195

<210> SEQ ID NO 68
<211> LENGTH: 199
<212> TYPE: PRT
<213> ORGANISM: Medicago truncatula
<220> FEATURE:
<223> OTHER INFORMATION: barrel medic unknown protein, clone
      MTYF1_F2_F3_FY1G-K-4, GenBank Accession No. ACJ83958.1,
      GI:217071196

<400> SEQUENCE: 68

Met Glu Lys Met Asn Gly Thr Glu Asn Asn Gly Val Phe Asn Ser Thr
  1               5                  10                  15

Glu Met Glu Tyr Ile Arg Arg His His Asn Gln Gln Pro Gly Glu Asn
             20                  25                  30

Gln Cys Ser Ser Ala Leu Val Lys His Ile Arg Ala Pro Val Pro Leu
         35                  40                  45

Val Trp Ser Leu Val Arg Arg Phe Asp Gln Pro Gln Lys Tyr Lys Pro
 50                  55                  60

Phe Val Ser Arg Cys Val Val Arg Gly Asn Leu Glu Ile Gly Ser Leu
 65                  70                  75                  80

Arg Glu Val Asp Val Lys Ser Gly Leu Pro Ala Thr Thr Ser Thr Glu
                 85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Ala Gln Asp Leu Thr Glu Pro Leu Asp Arg Met
            180                 185                 190

His Glu Leu Leu Ile Ser Gly
        195

<210> SEQ ID NO 69
<211> LENGTH: 197
<212> TYPE: PRT
<213> ORGANISM: Zea mays
<220> FEATURE:
<223> OTHER INFORMATION: maize CAPIP1 protein, clone 244179, GenBank
      Accession No. ACG34726.1, GI:195625792

<400> SEQUENCE: 69

Met Val Gly Leu Val Gly Gly Ser Thr Ala Arg Ala Glu His Val Val
  1               5                  10                  15

Ala Asn Ala Gly Gly Glu Ala Glu Tyr Val Arg Arg Met His Arg His
             20                  25                  30

Ala Pro Thr Glu His Gln Cys Thr Ser Thr Leu Val Lys His Ile Lys
         35                  40                  45

Ala Pro Val His Leu Val Trp Gln Leu Val Arg Arg Phe Asp Gln Pro
 50                  55                  60
```

```
Gln Arg Tyr Lys Pro Phe Val Arg Asn Cys Val Val Arg Gly Asp Gln
 65                  70                  75                  80

Leu Glu Val Gly Ser Leu Arg Asp Val Asn Val Lys Thr Gly Leu Pro
                 85                  90                  95

Ala Thr Thr Ser Thr Glu Arg Leu Glu Gln Leu Asp Asp Leu His
            100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
        130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 70
<211> LENGTH: 197
<212> TYPE: PRT
<213> ORGANISM: Zea mays
<220> FEATURE:
<223> OTHER INFORMATION: maize CAPIP1 protein, clone 1448906, GenBank
      Accession No. ACG26022.1, GI:195608384

<400> SEQUENCE: 70

Met Val Gly Leu Val Gly Gly Ser Thr Ala Arg Ala Glu His Val Val
 1               5                  10                  15

Ala Asn Ala Gly Gly Glu Ala Glu Tyr Val Arg Arg Met His Arg His
                 20                  25                  30

Ala Pro Thr Glu His Gln Cys Thr Ser Thr Leu Val Lys His Ile Lys
            35                  40                  45

Ala Pro Val His Leu Val Trp Glu Leu Val Arg Arg Phe Asp Gln Pro
        50                  55                  60

Gln Arg Tyr Lys Pro Phe Val Arg Asn Cys Val Val Arg Gly Asp Gln
 65                  70                  75                  80

Leu Glu Val Gly Ser Leu Arg Asp Val Asn Val Lys Thr Gly Leu Pro
                 85                  90                  95

Ala Thr Thr Ser Thr Glu Arg Leu Glu Gln Leu Asp Asp Leu His
            100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
        130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195
```

-continued

```
<210> SEQ ID NO 71
<211> LENGTH: 212
<212> TYPE: PRT
<213> ORGANISM: Zea mays
<220> FEATURE:
<223> OTHER INFORMATION: maize strain B73 unknown protein, clone
      ZM_BFc0183D21, GenBank Accession No. ACF86162.1, GI:194704156

<400> SEQUENCE: 71
```

Met Val Met Val Glu Met Asp Gly Gly Val Gly Gly Gly Gly Gly
1               5                   10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
        35                  40                  45

Glu Pro Arg Glu His Gln Cys Ser Ser Ala Val Ala Lys His Ile Lys
    50                  55                  60

Ala Pro Val His Leu Val Trp Ser Leu Val Arg Arg Phe Asp Gln Pro
65                  70                  75                  80

Gln Leu Phe Lys Pro Phe Val Ser Arg Cys Glu Met Lys Gly Asn Ile
                85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
        115                 120                 125

Leu Ser Val Arg Phe Val Gly Gly Asp His Arg Leu Gln Asn Tyr Ser
    130                 135                 140

Ser Ile Leu Thr Val His Pro Glu Val Ile Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Glu Ala Leu Leu Lys Cys Asn Leu Lys
            180                 185                 190

Ser Leu Ala Glu Val Ser Glu Arg Gln Val Val Lys Asp Gln Thr Glu
        195                 200                 205

Pro Leu Asp Arg
    210

```
<210> SEQ ID NO 72
<211> LENGTH: 205
<212> TYPE: PRT
<213> ORGANISM: Oryza sativa
<220> FEATURE:
<223> OTHER INFORMATION: rice Japonica Group, cultivar Nipponbare,
      conserved hypothetical protein Os06g0527800, GenBank Accession No.
      NP_001057771.1, GI:115468344

<400> SEQUENCE: 72
```

Met Asn Gly Ala Gly Gly Ala Gly Gly Ala Ala Ala Gly Lys Leu Pro
1               5                   10                  15

Met Val Ser His Arg Arg Val Gln Cys Arg Leu Ala Asp Lys Arg Cys
            20                  25                  30

Glu Leu Arg Glu Glu Glu Met Glu Tyr Ile Arg Gln Phe His Arg His
        35                  40                  45

Glu Pro Ser Ser Asn Gln Cys Thr Ser Phe Val Ala Lys His Ile Lys
    50                  55                  60

Ala Pro Leu Gln Thr Val Trp Ser Leu Val Arg Arg Phe Asp Gln Pro
65                  70                  75                  80

-continued

Gln Leu Phe Lys Pro Phe Val Arg Lys Cys Val Met Arg Glu Asn Ile
              85                  90                  95

Ile Val Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn
        195                 200                 205

<210> SEQ ID NO 73
<211> LENGTH: 197
<212> TYPE: PRT
<213> ORGANISM: Zea mays
<220> FEATURE:
<223> OTHER INFORMATION: maize strain B73 unknown protein, clone
      ZM_BFc0063E17, GenBank Accession No. ACF85073.1, GI:194701978

<400> SEQUENCE: 73

Met Val Gly Leu Val Gly Gly Ser Thr Ala Arg Ala Glu His Val Val
1               5                   10                  15

Ala Asn Ala Gly Gly Glu Thr Glu Tyr Val Arg Arg Leu His Arg His
            20                  25                  30

Ala Pro Ala Glu His Gln Cys Thr Ser Thr Leu Val Lys His Ile Lys
        35                  40                  45

Ala Pro Val His Leu Val Trp Glu Leu Val Arg Ser Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
            180                 185                 190

Ser Pro Ile Asp Gln
        195

<210> SEQ ID NO 74
<211> LENGTH: 206
<212> TYPE: PRT
<213> ORGANISM: Oryza sativa -continued

```
<220> FEATURE:
<223> OTHER INFORMATION: rice Indica Group, cultivar 93-11,
      hypothetical protein OsI_23218, old locus tag OsI_022423,
      GLEAN gene, GenBank Accession No. EAZ01191.1, GI:125555585

<400> SEQUENCE: 74
```

Met Asn Gly Val Gly Gly Ala Gly Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Glu Met Glu Tyr Ile Arg Arg Phe His Arg His
        35                  40                  45

Glu Pro Ser Ser Asn Gln Cys Thr Ser Phe Ala Ala Lys His Ile Lys
    50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Val Glu Asn Val Leu Arg Cys Asn Leu
            180                 185                 190

Arg Thr Leu Ala Asp Val Ser Glu Gly Arg Leu Ala Asn Pro
        195                 200                 205

```
<210> SEQ ID NO 75
<211> LENGTH: 209
<212> TYPE: PRT
<213> ORGANISM: Oryza sativa
<220> FEATURE:
<223> OTHER INFORMATION: rice Japonica Group, cultivar Nipponbare,
      conserved hypothetical protein Os05g0213500, GenBank Accession No.
      NP_001054923.1, GI:115462647

<400> SEQUENCE: 75
```

Met Val Gly Leu Val Gly Gly Gly Gly Trp Arg Val Gly Asp Asp Ala
1               5                   10                  15

Ala Gly Gly Gly Gly Gly Ala Val Ala Gly Ala Ala Ala
            20                  25                  30

Ala Glu Ala Glu His Met Arg Arg Leu His Ser His Ala Pro Gly Glu
        35                  40                  45

His Gln Cys Ser Ser Ala Leu Val Lys His Ile Lys Ala Pro Val His
    50                  55                  60

Leu Val Trp Ser Leu Val Arg Ser Phe Asp Gln Pro Gln Arg Tyr Lys
65                  70                  75                  80

Pro Phe Val Ser Arg Cys Val Val Arg Gly Gly Asp Leu Glu Ile Gly
                85                  90                  95

Ser Val Arg Glu Val Asn Val Lys Thr Gly Leu Pro Ala Thr Thr Ser
            100                 105                 110

```
Thr Glu Arg Leu Glu Leu Leu Asp Asp Asp Glu His Ile Leu Ser Val
            115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
            180                 185                 190

Glu Val Ser Glu Arg Leu Ala Val Gln Ser Pro Thr Ser Pro Leu Glu
        195                 200                 205

Gln

<210> SEQ ID NO 76
<211> LENGTH: 180
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, clone OSJNBa0052K15, gene
      OSJNBa0052K15.17, GenBank Accession No. BAD29692.1,
      GI:50251668

<400> SEQUENCE: 76

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Pro Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Val Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 77
<211> LENGTH: 176
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_029498, GenBank
      Accession No. CAN64668.1, GI:147797548
```

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175

<210> SEQ ID NO 78
<211> LENGTH: 180
<212> TYPE: PRT
<213> ORGANISM: Oryza sativa
<220> FEATURE:
<223> OTHER INFORMATION: rice Indica Group, cultivar 93-11, hypothetical
      protein, locus tag OsI_06615, GLEAN gene, GenBank Accession No.
      EEC72859.1, GI:218190432

<400> SEQUENCE: 78

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Pro His Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Ser Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Ile Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
        180

<210> SEQ ID NO 79
<211> LENGTH: 215
<212> TYPE: PRT
<213> ORGANISM: Oryza sativa
<220> FEATURE:
<223> OTHER INFORMATION: rice Japonica Group, cultivar Nipponbare,
      hypothetical protein OsJ_10498, old locus tag OsJ_010081, GLEAN
      gene, GenBank Accession No. EAZ26598.1, GI:125585934

<400> SEQUENCE: 79

Met Pro Cys Ile Pro Ala Ser Ser Pro Gly Ile Pro His Gln His Gln
 1               5                  10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Leu Gly Lys Val Arg Glu Arg Leu Glu Ile Leu Asp
        115                 120                 125

Asp Glu Ser His Val Leu Ser Phe Arg Val Val Gly Gly Glu His Arg
    130                 135                 140

Leu Lys Asn Tyr Leu Ser Val Thr Thr Val His Pro Ser Pro Ser Ala
145                 150                 155                 160

Pro Thr Ala Ala Thr Val Val Glu Ser Tyr Val Val Asp Val Pro
                165                 170                 175

Pro Gly Asn Thr Pro Glu Asp Thr Arg Val Phe Val Asp Thr Ile Val
            180                 185                 190

Lys Cys Asn Leu Gln Ser Leu Ala Lys Thr Ala Glu Lys Leu Ala Ala
        195                 200                 205

Gly Ala Arg Ala Ala Gly Ser
    210                 215

<210> SEQ ID NO 80
<211> LENGTH: 186
<212> TYPE: PRT
<213> ORGANISM: Rheum australe
<220> FEATURE:
<223> OTHER INFORMATION: Himalayan rhubarb pathogen-induced protein-
      like protein, GenBank Accession No. ACH63237.1, GI:197312913

<400> SEQUENCE: 80

Met Asn Gly Asp Gly Tyr Gly Gly Ser Glu Glu Glu Phe Val Lys Arg
 1               5                  10                  15

Tyr His Glu His Val Leu Ala Asp His Gln Cys Ser Ser Val Leu Val
            20                  25                  30

Glu His Ile Asn Ala Pro Leu His Leu Val Trp Ser Leu Val Arg Ser
        35                  40                  45

Phe Asp Gln Pro Gln Lys Tyr Lys Pro Phe Val Ser Arg Cys Val Val

```
            50                  55                  60
Gln Gly Gly Asp Leu Glu Ile Gly Ser Val Arg Glu Val Asp Val Lys
 65                  70                  75                  80

Ser Gly Leu Pro Ala Thr Thr Ser Met Glu Glu Leu Glu Leu Leu Asp
                 85                  90                  95

Asp Lys Glu His Val Leu Arg Val Lys Phe Val Gly Gly Asp His Arg
            100                 105                 110

Leu Lys Asn Tyr Ser Ser Ile Val Ser Leu His Pro Glu Ile Ile Gly
        115                 120                 125

Gly Arg Ser Gly Thr Met Val Ile Glu Ser Phe Ile Val Asp Ile Ala
130                 135                 140

Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
            180                 185

<210> SEQ ID NO 81
<211> LENGTH: 254
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_016770, GenBank Accession No.
      EAZ33287.1, GI:125593228

<400> SEQUENCE: 81

Met Val Gly Leu Val Gly Gly Gly Trp Arg Val Gly Asp Asp Ala
 1               5                  10                  15

Ala Gly Gly Gly Gly Gly Ala Val Ala Ala Gly Ala Ala Ala Ala
            20                  25                  30

Ala Glu Ala Glu His Met Arg Arg Leu His Ser Gln Gly Pro Arg Arg
         35                  40                  45

Ala Pro Val Gln Leu Arg Ala Arg Gln Ala His Gln Gly Ser Cys Ser
     50                  55                  60

Pro Pro Arg Ile Glu Cys Ala Asn Phe Ala Val Phe Leu Ala Ala Arg
 65                  70                  75                  80

Asp Pro Lys Ile Val Trp Ser Leu Val Arg Ser Phe Asp Gln Pro Gln
                 85                  90                  95

Arg Tyr Lys Pro Phe Val Ser Arg Cys Val Val Arg Gly Gly Asp Leu
            100                 105                 110

Glu Ile Gly Ser Val Arg Glu Val Asn Val Lys Thr Gly Leu Pro Ala
        115                 120                 125

Thr Thr Ser Thr Glu Arg Leu Glu Leu Leu Asp Asp Asp Glu His Ile
130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
            180                 185                 190

Asp Glu Thr Cys Tyr Phe Val Glu Ala Val Ile Lys Cys Asn Leu Thr
        195                 200                 205

Ser Leu Ala Glu Met Val Arg Met Ile Ser Leu Val Leu Pro Phe Met
210                 215                 220
```

```
Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
            245                 250

<210> SEQ ID NO 82
<211> LENGTH: 186
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005784, GenBank Accession No.
      EAZ22301.1, GI:125581370

<400> SEQUENCE: 82

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Gly
                20                  25                  30

Trp Asn Ala Pro Leu Ala Ala Val Trp Pro His Arg Ala Arg Val Arg
            35                  40                  45

Pro Thr Arg Ser Gly Thr Ser Thr Ser Ser Arg Ala Ser Ser Pro
        50                  55                  60

Pro Gly Asp Gly Ala Thr Val Gly Ser Val Arg Glu Val Ala Val Val
65                  70                  75                  80

Ser Gly Leu Pro Ala Ser Thr Ser Thr Glu Arg Leu Glu Ile Leu Asp
                85                  90                  95

Asp Asp Arg His Val Leu Ser Phe Arg Val Val Gly Gly Asp His Arg
                100                 105                 110

Leu Arg Asn Tyr Arg Ser Val Thr Ser Val Thr Glu Phe Ser Ser Pro
            115                 120                 125

Ser Ser Pro Pro Arg Pro Tyr Cys Val Val Val Glu Ser Tyr Val Val
        130                 135                 140

Asp Val Pro Glu Gly Asn Thr Glu Glu Asp Thr Arg Met Phe Thr Asp
145                 150                 155                 160

Thr Val Val Lys Leu Asn Leu Gln Lys Leu Ala Ala Val Ala Thr Ser
                165                 170                 175

Ser Ser Pro Pro Ala Ala Gly Asn His His
            180                 185

<210> SEQ ID NO 83
<211> LENGTH: 150
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005938, GenBank Accession No.
      EAZ22455.1, GI:125581524

<400> SEQUENCE: 83

Met Glu Val Val Trp Ser Ile Val Arg Arg Phe Glu Glu Pro His Ile
1               5                   10                  15

Phe Gln Pro Phe Val Arg Gly Cys Thr Met Arg Gly Ser Thr Ser Leu
                20                  25                  30

Ala Val Gly Cys Val Arg Glu Val Asp Phe Lys Ser Gly Phe Pro Ala
            35                  40                  45

Lys Ser Ser Val Glu Arg Leu Glu Ile Leu Asp Asp Lys Glu His Val
        50                  55                  60
```

Phe Gly Val Arg Ile Ile Gly Gly Asp His Arg Leu Lys Asn Tyr Ser
65                  70                  75                  80

Ser Val Leu Thr Ala Lys Pro Glu Val Ile Asp Gly Glu Pro Ala Thr
                85                  90                  95

Leu Val Ser Glu Ser Phe Val Val Asp Val Pro Glu Gly Asn Thr Ala
            100                 105                 110

Asp Glu Thr Arg His Phe Val Glu Phe Leu Ile Arg Cys Asn Leu Arg
        115                 120                 125

Ser Leu Ala Met Val Ser Gln Arg Leu Leu Leu Ala Gln Gly Asp Leu
    130                 135                 140

Ala Glu Pro Pro Gly Gln
145                 150

<210> SEQ ID NO 84
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_018129, GenBank Accession No.
      EAZ34646.1, GI:125594587

<400> SEQUENCE: 84

Met Pro Tyr Thr Ala Pro Arg Pro Ser Pro Pro Gln His Ser Arg Ile
1               5                   10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ser Asn Tyr Arg Ser Val
    130                 135                 140

Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
            180                 185                 190

Arg Thr Ala Glu Gln Leu Ala Leu Ala Ala Pro Arg Ala Ala
        195                 200                 205

<210> SEQ ID NO 85
<211> LENGTH: 396
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_001710, GenBank
      Accession No. CAN76441.1, GI:147770961
<220> FEATURE:

<221> NAME/KEY: VARIANT
<222> LOCATION: (61)...(61)
<223> OTHER INFORMATION: Xaa = any amino acid
<220> FEATURE:
<221> NAME/KEY: VARIANT
<222> LOCATION: (168)...(168)
<223> OTHER INFORMATION: Xaa = any amino acid
<220> FEATURE:
<221> NAME/KEY: VARIANT
<222> LOCATION: (181)...(181)
<223> OTHER INFORMATION: Xaa = any amino acid
<220> FEATURE:
<221> NAME/KEY: VARIANT
<222> LOCATION: (277)...(277)
<223> OTHER INFORMATION: Xaa = any amino acid

<400> SEQUENCE: 85

Met Pro Ile Ser Ser Leu Pro Phe Ser Leu Tyr Thr Val Thr Pro Asn
1               5                   10                  15

Pro Leu Lys Leu Ile Thr Thr His Ala His Ala Phe Thr Pro His Thr
            20                  25                  30

His Ile Phe Thr Leu Lys Phe Met Ser His Thr Tyr Cys Pro His Ile
        35                  40                  45

His His Ile Thr Ser Ile His Tyr Thr His Leu Leu Xaa Pro Ile Pro
    50                  55                  60

His Met Pro Leu Gln Pro Pro Leu Pro Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
    130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
    210                 215                 220

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
                245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
        275                 280                 285

Thr Ala Thr Asn Thr Gly Arg Leu Asp Met Gln Asp Asp Glu Arg His
    290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro

```
                    325                 330                 335
Ser Glu His Leu Lys Thr Ala Ala Ser Pro Lys Thr Glu Ser Ile Ile
                340                 345                 350

Val Ile Asp Thr Ser Lys Phe Leu Asn Glu Glu Asp Phe Glu Gly Lys
                355                 360                 365

Asp Glu Thr Ser Ser Ser Asn Gln Val Gln Ile Glu Asp Glu Asn Trp
            370                 375                 380

Glu Thr Arg Phe Pro Asn Thr Asp Ala Gly Ile Trp
385                 390                 395

<210> SEQ ID NO 86
<211> LENGTH: 443
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_014403, GenBank
      Accession No. CAN9881.1, GI:147828564
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (15)...(15)
<223> OTHER INFORMATION: Xaa = any amino acid
<220> FEATURE:
<221> NAME/KEY: VARIANT
<222> LOCATION: (129)...(129)
<223> OTHER INFORMATION: Xaa = any amino acid
<220> FEATURE:
<221> NAME/KEY: VARIANT
<222> LOCATION: (220)...(220)
<223> OTHER INFORMATION: Xaa = any amino acid
<220> FEATURE:
<221> NAME/KEY: VARIANT
<222> LOCATION: (401)...(401)
<223> OTHER INFORMATION: Xaa = any amino acid
<220> FEATURE:
<221> NAME/KEY: VARIANT
<222> LOCATION: (443)...(443)
<223> OTHER INFORMATION: Xaa = any amino acid

<400> SEQUENCE: 86

Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
                20                  25                  30

Leu Asp Ser Leu Ala Met Leu Gln Arg Gln Leu Asp Val Asp Ile Leu
            35                  40                  45

Val Thr Gly His Thr His Arg Phe Thr Ala Tyr Lys His Glu Gly Gly
        50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
                100                 105                 110

Lys Glu Leu His Ala Arg Lys Ile Ser Phe Gly Thr Lys Ser Met Ile
            115                 120                 125

Xaa Cys Leu Leu Leu Lys Arg Arg Ser Thr Pro Lys Phe Arg Arg Lys
        130                 135                 140

Lys Leu Phe Leu Phe Gln Cys Arg Val Gln Met Thr Leu Thr Leu Thr
145                 150                 155                 160
```

```
Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
            180                 185                 190

Lys Ala Arg Phe Leu Asp Phe Lys Asp Met Gly Lys Leu Leu Ala Asp
        195                 200                 205

Ala Ser Gly Leu Arg Lys Ala Leu Ser Gly Gly Xaa Val Thr Ala Gly
    210                 215                 220

Met Ala Ile Phe Asp Thr Met Arg His Ile Arg Pro Asp Val Pro Thr
225                 230                 235                 240

Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
            260                 265                 270

Ala Pro Lys Gly Val Asn Val Ala Val Val Thr Val Lys Thr Lys Arg
        275                 280                 285

Thr Ile Gln Leu Lys Thr Ser Leu Glu Ile Ala Cys His Tyr Ala Gly
    290                 295                 300

Ile Asn Ile Ser Gly Ile Asn Gly Glu Val Met Pro Gly Gln Trp Glu
305                 310                 315                 320

Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
            340                 345                 350

Pro Gln Arg Tyr Gln His Val Ile Lys Ser Cys Arg Ile Glu Asp Gly
        355                 360                 365

Phe Glu Met Arg Met Gly Arg Leu Arg Asp Val Asn Ile Ile Ser Gly
    370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr
                405                 410                 415

Thr Glu Asn Asn Asn Ser Asp Ala Ser Ser Val Lys Ser Pro Ile Asn
            420                 425                 430

Gly Pro Ser Glu His Leu Lys Thr Ala Ala Xaa
        435                 440

<210> SEQ ID NO 87
<211> LENGTH: 95
<212> TYPE: PRT
<213> ORGANISM: Oryza sativa
<220> FEATURE:
<223> OTHER INFORMATION: rice Indica Group, cultivar Pokkali, capip1
      protein (partial), clone OSR-385-428-D5, GenBank Accession No.
      ABR25904.1, GI:149392053

<400> SEQUENCE: 87

Glu Ile Gly Ser Val Arg Glu Val Asn Val Lys Thr Gly Leu Pro Ala
 1               5                  10                  15

Thr Thr Ser Thr Glu Arg Leu Glu Leu Leu Asp Asp Asp Glu His Ile
            20                  25                  30

Leu Ser Val Lys Phe Val Gly Gly Asp His Arg Leu Arg Asn Tyr Ser
        35                  40                  45

Ser Ile Val Thr Val His Pro Glu Ser Ile Asp Gly Arg Pro Gly Thr
    50                  55                  60
```

```
Leu Val Ile Glu Ser Phe Val Asp Val Pro Asp Gly Asn Thr Lys
 65                  70                  75                  80

Asp Glu Thr Cys Tyr Phe Val Glu Ala Val Ile Lys Cys Asn Leu
                 85                  90                  95

<210> SEQ ID NO 88
<211> LENGTH: 191
<212> TYPE: PRT
<213> ORGANISM: Zea mays
<220> FEATURE:
<223> OTHER INFORMATION: maize strain B73 unknown protein, clone
      ZM_BFc0034O07, GenBank Accession No. ACF84624.1, GI:194701080

<400> SEQUENCE: 88

Met Val Val Glu Met Asp Gly Gly Val Gly Val Ala Ala Ala Gly
  1               5                  10                  15

Gly Gly Ala Gln Thr Pro Ala Pro Pro Pro Arg Arg Trp Arg Leu
                 20                  25                  30

Ala Asp Glu Arg Cys Asp Leu Arg Ala Met Glu Thr Asp Tyr Val Arg
                 35                  40                  45

Arg Phe His Arg His Glu Pro Arg Asp His Gln Cys Ser Ser Ala Val
 50                  55                  60

Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
                 85                  90                  95

Met Lys Gly Asn Ile Glu Ile Gly Ser Val Arg Glu Val Asn Val Lys
                100                 105                 110

Ser Gly Leu Pro Ala Thr Arg Ser Thr Glu Arg Leu Glu Leu Leu Asp
                115                 120                 125

Asp Asp Glu Arg Ile Leu Ser Val Arg Phe Val Gly Asp His Arg
                130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
                165                 170                 175

Gln Met His Leu Asp Val Leu Pro Cys Asp Asp Ala Ile Leu Glu
                180                 185                 190

<210> SEQ ID NO 89
<211> LENGTH: 239
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_020681, GenBank Accession No.
      EAZ37198.1, GI:125597418

<400> SEQUENCE: 89

Met Asn Gly Cys Thr Gly Gly Ala Gly Gly Val Ala Ala Gly Arg Leu
  1               5                  10                  15

Pro Ala Val Ser Leu Gln Gln Ala Gln Trp Lys Leu Val Asp Glu Arg
                 20                  25                  30

Cys Glu Leu Arg Glu Glu Met Glu Tyr Val Arg Arg Phe His Arg
                 35                  40                  45

His Glu Ile Gly Ser Asn Gln Cys Asn Ser Phe Ile Ala Lys His Val
 50                  55                  60

Arg Ala Pro Leu Gln Asn Val Trp Ser Leu Val Arg Arg Phe Asp Gln
 65                  70                  75                  80
```

```
Pro Gln Ile Tyr Lys Pro Phe Val Arg Lys Cys Val Met Arg Gly Asn
                85                  90                  95
Val Glu Thr Gly Ser Val Arg Glu Ile Val Gln Ser Gly Leu Pro
            100                 105                 110
Ala Thr Arg Ser Ile Glu Arg Leu Glu Phe Leu Asp Asp Asn Glu Tyr
            115                 120                 125
Ile Leu Arg Val Lys Phe Ile Gly Gly Asp His Met Leu Lys Lys Arg
130                 135                 140
Ile Pro Lys Lys Thr Tyr Ala Ile Ser Ser Arg Thr Cys Ser Asp Ser
145                 150                 155                 160
Ala Ile Ile Ala Val Gly Gln Ser Asn Cys Ala Pro Glu Ile Thr Ala
                165                 170                 175
Met Asn Gly Gly Val Ser Ile Gln Pro Trp Leu Ile Leu Leu Ala Phe
            180                 185                 190
Phe Ser Ser Pro Ser Asn Gln Thr Asn Pro Asp Ser Leu Arg Asp Met
                195                 200                 205
His Pro Gly Ser Trp Phe Gln Ile Leu Leu Val Leu Ala Met Phe Thr
    210                 215                 220
Cys Ser Lys Gly Ser Val Leu Pro Pro Ser Glu Lys Val Asn Val
225                 230                 235

<210> SEQ ID NO 90
<211> LENGTH: 24
<212> TYPE: PRT
<213> ORGANISM: Artificial Sequence
<220> FEATURE:
<223> OTHER INFORMATION: synthetic PYR/PYL polypeptide conserved motif
      consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(6)
<223> OTHER INFORMATION: Xaa = any amino acid
<220> FEATURE:
<221> NAME/KEY: VARIANT
<222> LOCATION: (8)...(18)
<223> OTHER INFORMATION: Xaa = any amino acid
<220> FEATURE:
<221> NAME/KEY: VARIANT
<222> LOCATION: (21)...(21)
<223> OTHER INFORMATION: Xaa = any amino acid
<220> FEATURE:
<221> NAME/KEY: VARIANT
<222> LOCATION: (23)...(23)
<223> OTHER INFORMATION: Xaa = any amino acid

<400> SEQUENCE: 90

Glu Xaa Leu Xaa Xaa Xaa Asp Xaa Xaa Xaa Xaa Xaa Xaa Xaa Xaa Xaa
1               5                   10                  15
Xaa Xaa Gly Gly Xaa His Xaa Leu
            20

<210> SEQ ID NO 91
<211> LENGTH: 36
<212> TYPE: PRT
<213> ORGANISM: Artificial Sequence
<220> FEATURE:
<223> OTHER INFORMATION: synthetic PYR/PYL polypeptide conserved motif
      consensus sequence
<220> FEATURE:
<221> NAME/KEY: VARIANT
<222> LOCATION: (2)...(2)
```

```
<223> OTHER INFORMATION: Xaa = any amino acid
<220> FEATURE:
<221> NAME/KEY: VARIANT
<222> LOCATION: (4)...(10)
<223> OTHER INFORMATION: Xaa = any amino acid
<220> FEATURE:
<221> NAME/KEY: VARIANT
<222> LOCATION: (12)...(16)
<223> OTHER INFORMATION: Xaa = any amino acid
<220> FEATURE:
<221> NAME/KEY: VARIANT
<222> LOCATION: (18)...(22)
<223> OTHER INFORMATION: Xaa = any amino acid
<220> FEATURE:
<221> NAME/KEY: VARIANT
<222> LOCATION: (24)...(25)
<223> OTHER INFORMATION: Xaa = any amino acid
<220> FEATURE:
<221> NAME/KEY: VARIANT
<222> LOCATION: (26)...(31)
<223> OTHER INFORMATION: Xaa = any amino acid
<220> FEATURE:
<221> NAME/KEY: VARIANT
<222> LOCATION: (33)...(35)
<223> OTHER INFORMATION: Xaa = any amino acid

<400> SEQUENCE: 91

Cys Xaa Ser Xaa Xaa Xaa Xaa Xaa Xaa Ala Pro Xaa Xaa Xaa Xaa
 1               5                  10                 15

Trp Xaa Xaa Xaa Xaa Xaa Phe Xaa Xaa Pro Xaa Xaa Xaa Xaa Xaa Phe
             20                  25                  30

Xaa Xaa Xaa Cys
         35

<210> SEQ ID NO 92
<211> LENGTH: 25
<212> TYPE: PRT
<213> ORGANISM: Artificial Sequence
<220> FEATURE:
<223> OTHER INFORMATION: synthetic PYR/PYL polypeptide conserved motif
      consensus sequence
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (7)...(9)
<223> OTHER INFORMATION: Xaa = any amino acid
<220> FEATURE:
<221> NAME/KEY: VARIANT
<222> LOCATION: (11)...(12)
<223> OTHER INFORMATION: Xaa = any amino acid
<220> FEATURE:
<221> NAME/KEY: VARIANT
<222> LOCATION: (15)...(16)
<223> OTHER INFORMATION: Xaa = any amino acid
<220> FEATURE:
<221> NAME/KEY: VARIANT
<222> LOCATION: (18)...(18)
<223> OTHER INFORMATION: Xaa = any amino acid
<220> FEATURE:
<221> NAME/KEY: VARIANT
<222> LOCATION: (20)...(20)
<223> OTHER INFORMATION: Xaa = any amino acid
<220> FEATURE:
<221> NAME/KEY: VARIANT
<222> LOCATION: (22)...(24)
<223> OTHER INFORMATION: Xaa = any amino acid

<400> SEQUENCE: 92
```

```
Gly Xaa Xaa Arg Xaa Val Xaa Xaa Xaa Ser Xaa Xaa Pro Ala Xaa Xaa
1               5                   10                  15

Ser Xaa Glu Xaa Leu Xaa Xaa Xaa Asp
            20                  25

<210> SEQ ID NO 93
<211> LENGTH: 11
<212> TYPE: PRT
<213> ORGANISM: Artificial Sequence
<220> FEATURE:
<223> OTHER INFORMATION: synthetic PYR/PYL polypeptide conserved motif
      consensus sequence
<220> FEATURE:
<221> NAME/KEY: VARIANT
<222> LOCATION: (3)...(3)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (10)...(10)
<223> OTHER INFORMATION: Xaa = any amino acid

<400> SEQUENCE: 93

Gly Gly Xaa His Arg Leu Xaa Asn Tyr Xaa Ser
1               5                   10

<210> SEQ ID NO 94
<211> LENGTH: 36
<212> TYPE: PRT
<213> ORGANISM: Artificial Sequence
<220> FEATURE:
<223> OTHER INFORMATION: synthetic PYR1 to PYL12 Arabidopsis PYR/PYL
      polypeptide consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(10)
<223> OTHER INFORMATION: Xaa = any amino acid
<220> FEATURE:
<221> NAME/KEY: VARIANT
<222> LOCATION: (13)...(16)
<223> OTHER INFORMATION: Xaa = any amino acid
<220> FEATURE:
<221> NAME/KEY: VARIANT
<222> LOCATION: (18)...(22)
<223> OTHER INFORMATION: Xaa = any amino acid
<220> FEATURE:
<221> NAME/KEY: VARIANT
<222> LOCATION: (24)...(25)
<223> OTHER INFORMATION: Xaa = any amino acid
<220> FEATURE:
<221> NAME/KEY: VARIANT
<222> LOCATION: (27)...(31)
<223> OTHER INFORMATION: Xaa = any amino acid
<220> FEATURE:
<221> NAME/KEY: VARIANT
<222> LOCATION: (33)...(35)
<223> OTHER INFORMATION: Xaa = any amino acid

<400> SEQUENCE: 94

Cys Xaa Ser Xaa Xaa Xaa Xaa Xaa Xaa Ala Pro Xaa Xaa Xaa Xaa
1               5                   10                  15

Trp Xaa Xaa Xaa Xaa Xaa Phe Xaa Xaa Pro Xaa Xaa Xaa Xaa Xaa Phe
            20                  25                  30

Xaa Xaa Xaa Cys
```

-continued

```
<210> SEQ ID NO 95
<211> LENGTH: 25
<212> TYPE: PRT
<213> ORGANISM: Artificial Sequence
<220> FEATURE:
<223> OTHER INFORMATION: synthetic PYR1 to PYL12 Arabidopsis PYR/PYL
      polypeptide consensus sequence
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (7)...(9)
<223> OTHER INFORMATION: Xaa = any amino acid
<220> FEATURE:
<221> NAME/KEY: VARIANT
<222> LOCATION: (11)...(12)
<223> OTHER INFORMATION: Xaa = any amino acid
<220> FEATURE:
<221> NAME/KEY: VARIANT
<222> LOCATION: (15)...(16)
<223> OTHER INFORMATION: Xaa = any amino acid
<220> FEATURE:
<221> NAME/KEY: VARIANT
<222> LOCATION: (18)...(18)
<223> OTHER INFORMATION: Xaa = any amino acid
<220> FEATURE:
<221> NAME/KEY: VARIANT
<222> LOCATION: (20)...(20)
<223> OTHER INFORMATION: Xaa = any amino acid
<220> FEATURE:
<221> NAME/KEY: VARIANT
<222> LOCATION: (22)...(24)
<223> OTHER INFORMATION: Xaa = any amino acid

<400> SEQUENCE: 95

Gly Xaa Xaa Arg Xaa Val Xaa Xaa Xaa Ser Xaa Xaa Pro Ala Xaa Xaa
 1               5                  10                  15

Ser Xaa Glu Xaa Leu Xaa Xaa Xaa Asp
            20                  25

<210> SEQ ID NO 96
<211> LENGTH: 31
<212> TYPE: PRT
<213> ORGANISM: Artificial Sequence
<220> FEATURE:
<223> OTHER INFORMATION: synthetic PYR1 to PYL12 Arabidopsis PYR/PYL
      polypeptide consensus sequence
<220> FEATURE:
<221> NAME/KEY: VARIANT
<222> LOCATION: (3)...(4)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (9)...(9)
<223> OTHER INFORMATION: Xaa = any amino acid
<220> FEATURE:
<221> NAME/KEY: VARIANT
<222> LOCATION: (11)...(15)
<223> OTHER INFORMATION: Xaa = any amino acid
<220> FEATURE:
<221> NAME/KEY: VARIANT
<222> LOCATION: (17)...(18)
<223> OTHER INFORMATION: Xaa = any amino acid
```

<220> FEATURE:
<221> NAME/KEY: VARIANT
<222> LOCATION: (20)...(26)
<223> OTHER INFORMATION: Xaa = any amino acid
<220> FEATURE:
<221> NAME/KEY: VARIANT
<222> LOCATION: (29)...(30)
<223> OTHER INFORMATION: Xaa = any amino acid

<400> SEQUENCE: 96

Glu Ser Xaa Xaa Val Asp Xaa Pro Xaa Gly Xaa Xaa Xaa Xaa Xaa Thr
1               5                   10                  15

Xaa Xaa Phe Xaa Xaa Xaa Xaa Xaa Xaa Xaa Asn Leu Xaa Xaa Leu
            20                  25                  30

<210> SEQ ID NO 97
<211> LENGTH: 36
<212> TYPE: PRT
<213> ORGANISM: Artificial Sequence
<220> FEATURE:
<223> OTHER INFORMATION: synthetic PYL1-12 Arabidopsis PYR/PYL
      polypeptide consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(10)
<223> OTHER INFORMATION: Xaa = any amino acid
<220> FEATURE:
<221> NAME/KEY: VARIANT
<222> LOCATION: (13)...(16)
<223> OTHER INFORMATION: Xaa = any amino acid
<220> FEATURE:
<221> NAME/KEY: VARIANT
<222> LOCATION: (18)...(22)
<223> OTHER INFORMATION: Xaa = any amino acid
<220> FEATURE:
<221> NAME/KEY: VARIANT
<222> LOCATION: (24)...(25)
<223> OTHER INFORMATION: Xaa = any amino acid
<220> FEATURE:
<221> NAME/KEY: VARIANT
<222> LOCATION: (27)...(29)
<223> OTHER INFORMATION: Xaa = any amino acid
<220> FEATURE:
<221> NAME/KEY: VARIANT
<222> LOCATION: (31)...(31)
<223> OTHER INFORMATION: Xaa = any amino acid
<220> FEATURE:
<221> NAME/KEY: VARIANT
<222> LOCATION: (33)...(35)
<223> OTHER INFORMATION: Xaa = any amino acid

<400> SEQUENCE: 97

Cys Xaa Ser Xaa Xaa Xaa Xaa Xaa Xaa Xaa Ala Pro Xaa Xaa Xaa Xaa
1               5                   10                  15

Trp Xaa Xaa Xaa Xaa Xaa Phe Xaa Xaa Pro Xaa Xaa Xaa Lys Xaa Phe
            20                  25                  30

Xaa Xaa Xaa Cys
        35

<210> SEQ ID NO 98
<211> LENGTH: 25
<212> TYPE: PRT
<213> ORGANISM: Artificial Sequence
<220> FEATURE:
<223> OTHER INFORMATION: synthetic PYL1-12 Arabidopsis PYR/PYL
      polypeptide consensus sequence
<220> FEATURE:
<221> NAME/KEY: VARIANT

```
<222> LOCATION: (2)...(3)
<223> OTHER INFORMATION: Xaa = any amino acid
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (7)...(9)
<223> OTHER INFORMATION: Xaa = any amino acid
<220> FEATURE:
<221> NAME/KEY: VARIANT
<222> LOCATION: (11)...(11)
<223> OTHER INFORMATION: Xaa = any amino acid
<220> FEATURE:
<221> NAME/KEY: VARIANT
<222> LOCATION: (15)...(16)
<223> OTHER INFORMATION: Xaa = any amino acid
<220> FEATURE:
<221> NAME/KEY: VARIANT
<222> LOCATION: (18)...(18)
<223> OTHER INFORMATION: Xaa = any amino acid
<220> FEATURE:
<221> NAME/KEY: VARIANT
<222> LOCATION: (20)...(20)
<223> OTHER INFORMATION: Xaa = any amino acid
<220> FEATURE:
<221> NAME/KEY: VARIANT
<222> LOCATION: (22)...(24)
<223> OTHER INFORMATION: Xaa = any amino acid

<400> SEQUENCE: 98

Gly Xaa Xaa Arg Xaa Val Xaa Xaa Xaa Ser Xaa Leu Pro Ala Xaa Xaa
 1               5                  10                  15

Ser Xaa Glu Xaa Leu Xaa Xaa Xaa Asp
            20                  25

<210> SEQ ID NO 99
<211> LENGTH: 31
<212> TYPE: PRT
<213> ORGANISM: Artificial Sequence
<220> FEATURE:
<223> OTHER INFORMATION: synthetic PYL1-12 Arabidopsis PYR/PYL
      polypeptide consensus sequence
<220> FEATURE:
<221> NAME/KEY: VARIANT
<222> LOCATION: (3)...(4)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (9)...(9)
<223> OTHER INFORMATION: Xaa = any amino acid
<220> FEATURE:
<221> NAME/KEY: VARIANT
<222> LOCATION: (12)...(15)
<223> OTHER INFORMATION: Xaa = any amino acid
<220> FEATURE:
<221> NAME/KEY: VARIANT
<222> LOCATION: (17)...(18)
<223> OTHER INFORMATION: Xaa = any amino acid
<220> FEATURE:
<221> NAME/KEY: VARIANT
<222> LOCATION: (20)...(26)
<223> OTHER INFORMATION: Xaa = any amino acid
<220> FEATURE:
<221> NAME/KEY: VARIANT
<222> LOCATION: (29)...(30)
<223> OTHER INFORMATION: Xaa = any amino acid

<400> SEQUENCE: 99

Glu Ser Xaa Xaa Val Asp Xaa Pro Xaa Gly Asn Xaa Xaa Xaa Xaa Thr
```

```
                1               5                  10                  15
Xaa Xaa Phe Xaa Xaa Xaa Xaa Xaa Xaa Asn Leu Xaa Xaa Leu
                        20                  25                  30

<210> SEQ ID NO 100
<211> LENGTH: 45
<212> TYPE: PRT
<213> ORGANISM: Artificial Sequence
<220> FEATURE:
<223> OTHER INFORMATION: synthetic PYL1-6 Arabidopsis PYR/PYL
      polypeptide consensus sequence
<220> FEATURE:
<221> NAME/KEY: VARIANT
<222> LOCATION: (2)...(9)
<223> OTHER INFORMATION: Xaa = any amino acid
<220> FEATURE:
<221> NAME/KEY: VARIANT
<222> LOCATION: (11)...(11)
<223> OTHER INFORMATION: Xaa = any amino acid
<220> FEATURE:
<221> NAME/KEY: VARIANT
<222> LOCATION: (13)...(19)
<223> OTHER INFORMATION: Xaa = any amino acid
<220> FEATURE:
<221> NAME/KEY: VARIANT
<222> LOCATION: (22)...(25)
<223> OTHER INFORMATION: Xaa = any amino acid
<220> FEATURE:
<221> NAME/KEY: VARIANT
<222> LOCATION: (27)...(31)
<223> OTHER INFORMATION: Xaa = any amino acid
<220> FEATURE:
<221> NAME/KEY: VARIANT
<222> LOCATION: (33)...(34)
<223> OTHER INFORMATION: Xaa = any amino acid
<220> FEATURE:
<221> NAME/KEY: VARIANT
<222> LOCATION: (36)...(37)
<223> OTHER INFORMATION: Xaa = any amino acid
<220> FEATURE:
<221> NAME/KEY: VARIANT
<222> LOCATION: (40)...(40)
<223> OTHER INFORMATION: Xaa = any amino acid
<220> FEATURE:
<221> NAME/KEY: VARIANT
<222> LOCATION: (42)...(44)
<223> OTHER INFORMATION: Xaa = any amino acid

<400> SEQUENCE: 100

His Xaa Xaa Xaa Xaa Xaa Xaa Xaa Xaa Cys Xaa Ser Xaa Xaa Xaa Xaa
 1               5                  10                  15

Xaa Xaa Xaa Ala Pro Xaa Xaa Xaa Xaa Trp Xaa Xaa Xaa Xaa Xaa Phe
                20                  25                  30

Xaa Xaa Pro Xaa Xaa Tyr Lys Xaa Phe Xaa Xaa Xaa Cys
                35                  40                  45

<210> SEQ ID NO 101
<211> LENGTH: 50
<212> TYPE: PRT
<213> ORGANISM: Artificial Sequence
<220> FEATURE:
<223> OTHER INFORMATION: synthetic PYL1-6 Arabidopsis PYR/PYL
      polypeptide consensus sequence
<220> FEATURE:
<221> NAME/KEY: VARIANT
<222> LOCATION: (3)...(4)
<223> OTHER INFORMATION: Xaa = any amino acid
<220> FEATURE:
<221> NAME/KEY: VARIANT
<222> LOCATION: (6)...(6)
<223> OTHER INFORMATION: Xaa = any amino acid
<220> FEATURE:
<221> NAME/KEY: VARIANT
```

```
<222> LOCATION: (8)...(8)
<223> OTHER INFORMATION: Xaa = any amino acid
<220> FEATURE:
<221> NAME/KEY: VARIANT
<222> LOCATION: (10)...(10)
<223> OTHER INFORMATION: Xaa = any amino acid
<220> FEATURE:
<221> NAME/KEY: VARIANT
<222> LOCATION: (16)...(17)
<223> OTHER INFORMATION: Xaa = any amino acid
<220> FEATURE:
<221> NAME/KEY: VARIANT
<222> LOCATION: (19)...(19)
<223> OTHER INFORMATION: Xaa = any amino acid
<220> FEATURE:
<221> NAME/KEY: VARIANT
<222> LOCATION: (21)...(21)
<223> OTHER INFORMATION: Xaa = any amino acid
<220> FEATURE:
<221> NAME/KEY: VARIANT
<222> LOCATION: (23)...(25)
<223> OTHER INFORMATION: Xaa = any amino acid
<220> FEATURE:
<221> NAME/KEY: VARIANT
<222> LOCATION: (27)...(33)
<223> OTHER INFORMATION: Xaa = any amino acid
<220> FEATURE:
<221> NAME/KEY: VARIANT
<222> LOCATION: (35)...(37)
<223> OTHER INFORMATION: Xaa = any amino acid
<220> FEATURE:
<221> NAME/KEY: VARIANT
<222> LOCATION: (40)...(40)
<223> OTHER INFORMATION: Xaa = any amino acid
<220> FEATURE:
<221> NAME/KEY: VARIANT
<222> LOCATION: (44)...(44)
<223> OTHER INFORMATION: Xaa = any amino acid
<220> FEATURE:
<221> NAME/KEY: VARIANT
<222> LOCATION: (47)...(47)
<223> OTHER INFORMATION: Xaa = any amino acid

<400> SEQUENCE: 101

Val Gly Xaa Xaa Arg Xaa Val Xaa Val Xaa Ser Gly Leu Pro Ala Xaa
  1               5                  10                  15

Xaa Ser Xaa Glu Xaa Leu Xaa Xaa Xaa Asp Xaa Xaa Xaa Xaa Xaa Xaa
             20                  25                  30

Xaa Phe Xaa Xaa Xaa Gly Gly Xaa His Arg Leu Xaa Asn Tyr Xaa Ser
         35                  40                  45

Val Thr
 50

<210> SEQ ID NO 102
<211> LENGTH: 33
<212> TYPE: PRT
<213> ORGANISM: Artificial Sequence
<220> FEATURE:
<223> OTHER INFORMATION: synthetic PYL1-6 Arabidopsis PYR/PYL
      polypeptide consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (6)...(6)
<223> OTHER INFORMATION: Xaa = any amino acid
<220> FEATURE:
<221> NAME/KEY: VARIANT
<222> LOCATION: (9)...(9)
<223> OTHER INFORMATION: Xaa = any amino acid
<220> FEATURE:
<221> NAME/KEY: VARIANT
```

```
<222> LOCATION: (11)...(11)
<223> OTHER INFORMATION: Xaa = any amino acid
<220> FEATURE:
<221> NAME/KEY: VARIANT
<222> LOCATION: (14)...(17)
<223> OTHER INFORMATION: Xaa = any amino acid
<220> FEATURE:
<221> NAME/KEY: VARIANT
<222> LOCATION: (19)...(20)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid
<220> FEATURE:
<221> NAME/KEY: VARIANT
<222> LOCATION: (24)...(28)
<223> OTHER INFORMATION: Xaa = any amino acid
<220> FEATURE:
<221> NAME/KEY: VARIANT
<222> LOCATION: (32)...(32)
<223> OTHER INFORMATION: Xaa = any amino acid

<400> SEQUENCE: 102

Val Xaa Glu Ser Tyr Xaa Val Asp Xaa Pro Xaa Gly Asn Xaa Xaa Xaa
 1               5                  10                  15

Xaa Thr Xaa Xaa Phe Xaa Asp Xaa Xaa Xaa Xaa Xaa Asn Leu Gln Xaa
            20                  25                  30

Leu

<210> SEQ ID NO 103
<211> LENGTH: 50
<212> TYPE: PRT
<213> ORGANISM: Artificial Sequence
<220> FEATURE:
<223> OTHER INFORMATION: synthetic PYL7-10 Arabidopsis PYR/PYL
      polypeptide consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(8)
<223> OTHER INFORMATION: Xaa = any amino acid
<220> FEATURE:
<221> NAME/KEY: VARIANT
<222> LOCATION: (11)...(11)
<223> OTHER INFORMATION: Xaa = any amino acid
<220> FEATURE:
<221> NAME/KEY: VARIANT
<222> LOCATION: (13)...(13)
<223> OTHER INFORMATION: Xaa = any amino acid
<220> FEATURE:
<221> NAME/KEY: VARIANT
<222> LOCATION: (14)...(17)
<223> OTHER INFORMATION: Xaa = any amino acid
<220> FEATURE:
<221> NAME/KEY: VARIANT
<222> LOCATION: (19)...(20)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid
<220> FEATURE:
<221> NAME/KEY: VARIANT
<222> LOCATION: (24)...(24)
<223> OTHER INFORMATION: Xaa = any amino acid
<220> FEATURE:
<221> NAME/KEY: VARIANT
<222> LOCATION: (28)...(28)
<223> OTHER INFORMATION: Xaa = any amino acid
<220> FEATURE:
<221> NAME/KEY: VARIANT
```

```
<222> LOCATION: (34)...(34)
<223> OTHER INFORMATION: Xaa = any amino acid
<220> FEATURE:
<221> NAME/KEY: VARIANT
<222> LOCATION: (42)...(42)
<223> OTHER INFORMATION: Xaa = any amino acid
<220> FEATURE:
<221> NAME/KEY: VARIANT
<222> LOCATION: (46)...(46)
<223> OTHER INFORMATION: Xaa = any amino acid
<220> FEATURE:
<221> NAME/KEY: VARIANT
<222> LOCATION: (48)...(48)
<223> OTHER INFORMATION: Xaa = any amino acid
<220> FEATURE:
<221> NAME/KEY: VARIANT
<222> LOCATION: (50)...(50)
<223> OTHER INFORMATION: Xaa = any amino acid

<400> SEQUENCE: 103

His Xaa His Xaa Xaa Xaa Xaa Xaa Gln Cys Xaa Ser Xaa Leu Val Lys
 1               5                  10                  15

Xaa Ile Xaa Ala Pro Xaa His Xaa Val Trp Ser Xaa Val Arg Arg Phe
            20                  25                  30

Asp Xaa Pro Gln Lys Tyr Lys Pro Phe Xaa Ser Arg Cys Xaa Val Xaa
        35                  40                  45

Gly Xaa
    50

<210> SEQ ID NO 104
<211> LENGTH: 61
<212> TYPE: PRT
<213> ORGANISM: Artificial Sequence
<220> FEATURE:
<223> OTHER INFORMATION: synthetic PYL7-10 Arabidopsis PYR/PYL
      polypeptide consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(5)
<223> OTHER INFORMATION: Xaa = any amino acid
<220> FEATURE:
<221> NAME/KEY: VARIANT
<222> LOCATION: (9)...(10)
<223> OTHER INFORMATION: Xaa = any amino acid
<220> FEATURE:
<221> NAME/KEY: VARIANT
<222> LOCATION: (18)...(18)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid
<220> FEATURE:
<221> NAME/KEY: VARIANT
<222> LOCATION: (25)...(25)
<223> OTHER INFORMATION: Xaa = any amino acid
<220> FEATURE:
<221> NAME/KEY: VARIANT
<222> LOCATION: (29)...(29)
<223> OTHER INFORMATION: Xaa = any amino acid
<220> FEATURE:
<221> NAME/KEY: VARIANT
<222> LOCATION: (34)...(34)
<223> OTHER INFORMATION: Xaa = any amino acid
<220> FEATURE:
<221> NAME/KEY: VARIANT
<222> LOCATION: (36)...(36)
<223> OTHER INFORMATION: Xaa = any amino acid
<220> FEATURE:
<221> NAME/KEY: VARIANT
```

```
<222> LOCATION: (38)...(38)
<223> OTHER INFORMATION: Xaa = any amino acid
<220> FEATURE:
<221> NAME/KEY: VARIANT
<222> LOCATION: (50)...(53)
<223> OTHER INFORMATION: Xaa = any amino acid
<220> FEATURE:
<221> NAME/KEY: VARIANT
<222> LOCATION: (55)...(55)
<223> OTHER INFORMATION: Xaa = any amino acid
<220> FEATURE:
<221> NAME/KEY: VARIANT
<222> LOCATION: (57)...(57)
<223> OTHER INFORMATION: Xaa = any amino acid
<220> FEATURE:
<221> NAME/KEY: VARIANT
<222> LOCATION: (59)...(59)
<223> OTHER INFORMATION: Xaa = any amino acid
<220> FEATURE:
<221> NAME/KEY: VARIANT
<222> LOCATION: (61)...(61)
<223> OTHER INFORMATION: Xaa = any amino acid

<400> SEQUENCE: 104

Glu Xaa Gly Xaa Xaa Arg Glu Val Xaa Xaa Lys Ser Gly Leu Pro Ala
 1               5                  10                  15

Thr Xaa Ser Thr Glu Xaa Leu Glu Xaa Leu Asp Asp Xaa Glu His Ile
            20                  25                  30

Leu Xaa Ile Xaa Ile Xaa Gly Gly Asp His Arg Leu Lys Asn Tyr Ser
        35                  40                  45

Ser Xaa Xaa Xaa Xaa His Xaa Glu Xaa Ile Xaa Gly Xaa
    50                  55                  60

<210> SEQ ID NO 105
<211> LENGTH: 44
<212> TYPE: PRT
<213> ORGANISM: Artificial Sequence
<220> FEATURE:
<223> OTHER INFORMATION: synthetic PYL7-10 Arabidopsis PYR/PYL
      polypeptide consensus sequence
<220> FEATURE:
<221> NAME/KEY: VARIANT
<222> LOCATION: (1)...(1)
<223> OTHER INFORMATION: Xaa = any amino acid
<220> FEATURE:
<221> NAME/KEY: VARIANT
<222> LOCATION: (4)...(6)
<223> OTHER INFORMATION: Xaa = any amino acid
<220> FEATURE:
<221> NAME/KEY: VARIANT
<222> LOCATION: (15)...(15)
<223> OTHER INFORMATION: Xaa = any amino acid
<220> FEATURE:
<221> NAME/KEY: VARIANT
<222> LOCATION: (20)...(21)
<223> OTHER INFORMATION: Xaa = any amino acid
<220> FEATURE:
<221> NAME/KEY: VARIANT
<222> LOCATION: (24)...(24)
<223> OTHER INFORMATION: Xaa = any amino acid
<220> FEATURE:
<221> NAME/KEY: VARIANT
<222> LOCATION: (28)...(28)
<223> OTHER INFORMATION: Xaa = any amino acid
<220> FEATURE:
<221> NAME/KEY: VARIANT
<222> LOCATION: (31)...(31)
<223> OTHER INFORMATION: Xaa = any amino acid
<220> FEATURE:
<221> NAME/KEY: VARIANT
<222> LOCATION: (35)...(35)
<223> OTHER INFORMATION: Xaa = any amino acid
<220> FEATURE:
<221> NAME/KEY: VARIANT
```

```
<222> LOCATION: (39)...(41)
<223> OTHER INFORMATION: Xaa = any amino acid

<400> SEQUENCE: 105

Xaa Gly Thr Xaa Xaa Xaa Glu Ser Phe Val Val Asp Val Pro Xaa Gly
  1               5                  10                  15

Asn Thr Lys Xaa Xaa Thr Cys Xaa Phe Val Glu Xaa Leu Ile Xaa Cys
            20                  25                  30

Asn Leu Xaa Ser Leu Ala Xaa Xaa Xaa Glu Arg Leu
            35                  40

<210> SEQ ID NO 106
<211> LENGTH: 44
<212> TYPE: PRT
<213> ORGANISM: Artificial Sequence
<220> FEATURE:
<223> OTHER INFORMATION: synthetic PYL11-13 Arabidopsis PYR/PYL
      polypeptide consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(5)
<223> OTHER INFORMATION: Xaa = any amino acid
<220> FEATURE:
<221> NAME/KEY: VARIANT
<222> LOCATION: (7)...(7)
<223> OTHER INFORMATION: Xaa = any amino acid
<220> FEATURE:
<221> NAME/KEY: VARIANT
<222> LOCATION: (10)...(10)
<223> OTHER INFORMATION: Xaa = any amino acid
<220> FEATURE:
<221> NAME/KEY: VARIANT
<222> LOCATION: (14)...(14)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid
<220> FEATURE:
<221> NAME/KEY: VARIANT
<222> LOCATION: (25)...(25)
<223> OTHER INFORMATION: Xaa = any amino acid
<220> FEATURE:
<221> NAME/KEY: VARIANT
<222> LOCATION: (27)...(31)
<223> OTHER INFORMATION: Xaa = any amino acid
<220> FEATURE:
<221> NAME/KEY: VARIANT
<222> LOCATION: (35)...(35)
<223> OTHER INFORMATION: Xaa = any amino acid
<220> FEATURE:
<221> NAME/KEY: VARIANT
<222> LOCATION: (37)...(39)
<223> OTHER INFORMATION: Xaa = any amino acid
<220> FEATURE:
<221> NAME/KEY: VARIANT
<222> LOCATION: (42)...(42)
<223> OTHER INFORMATION: Xaa = any amino acid

<400> SEQUENCE: 106

Cys Xaa Ser Xaa Xaa Val Xaa Thr Ile Xaa Ala Pro Leu Xaa Leu Val
  1               5                  10                  15

Trp Ser Ile Leu Arg Xaa Phe Asp Xaa Pro Xaa Xaa Xaa Xaa Xaa Phe
            20                  25                  30

Val Lys Xaa Cys Xaa Xaa Xaa Ser Gly Xaa Gly Gly
            35                  40
```

```
<210> SEQ ID NO 107
<211> LENGTH: 49
<212> TYPE: PRT
<213> ORGANISM: Artificial Sequence
<220> FEATURE:
<223> OTHER INFORMATION: synthetic PYL11-13 Arabidopsis PYR/PYL
      polypeptide consensus sequence
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (8)...(8)
<223> OTHER INFORMATION: Xaa = any amino acid
<220> FEATURE:
<221> NAME/KEY: VARIANT
<222> LOCATION: (11)...(12)
<223> OTHER INFORMATION: Xaa = any amino acid
<220> FEATURE:
<221> NAME/KEY: VARIANT
<222> LOCATION: (15)...(15)
<223> OTHER INFORMATION: Xaa = any amino acid
<220> FEATURE:
<221> NAME/KEY: VARIANT
<222> LOCATION: (18)...(18)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid
<220> FEATURE:
<221> NAME/KEY: VARIANT
<222> LOCATION: (32)...(33)
<223> OTHER INFORMATION: Xaa = any amino acid
<220> FEATURE:
<221> NAME/KEY: VARIANT
<222> LOCATION: (39)...(39)
<223> OTHER INFORMATION: Xaa = any amino acid
<220> FEATURE:
<221> NAME/KEY: VARIANT
<222> LOCATION: (46)...(46)
<223> OTHER INFORMATION: Xaa = any amino acid

<400> SEQUENCE: 107

Gly Ser Val Arg Xaa Val Thr Xaa Val Ser Xaa Xaa Pro Ala Xaa Phe
1               5                   10                  15

Ser Xaa Glu Arg Leu Xaa Glu Leu Asp Asp Glu Ser His Val Met Xaa
            20                  25                  30

Xaa Ser Ile Ile Gly Gly Xaa His Arg Leu Val Asn Tyr Xaa Ser Lys
        35                  40                  45

Thr

<210> SEQ ID NO 108
<211> LENGTH: 40
<212> TYPE: PRT
<213> ORGANISM: Artificial Sequence
<220> FEATURE:
<223> OTHER INFORMATION: synthetic PYL11-13 Arabidopsis PYR/PYL
      polypeptide consensus sequence
<220> FEATURE:
<221> NAME/KEY: VARIANT
<222> LOCATION: (17)...(18)
<223> OTHER INFORMATION: Xaa = any amino acid
<220> FEATURE:
<221> NAME/KEY: VARIANT
<222> LOCATION: (21)...(21)
<223> OTHER INFORMATION: Xaa = any amino acid
<220> FEATURE:
<221> NAME/KEY: VARIANT
<222> LOCATION: (23)...(24)
<223> OTHER INFORMATION: Xaa = any amino acid
<220> FEATURE:
<221> NAME/KEY: VARIANT
```

```
<222> LOCATION: (26)...(26)
<223> OTHER INFORMATION: Xaa = any amino acid
<220> FEATURE:
<221> NAME/KEY: VARIANT
<222> LOCATION: (28)...(28)
<223> OTHER INFORMATION: Xaa = any amino acid
<220> FEATURE:
<221> NAME/KEY: VARIANT
<222> LOCATION: (30)...(32)
<223> OTHER INFORMATION: Xaa = any amino acid
<220> FEATURE:
<221> NAME/KEY: VARIANT
<222> LOCATION: (35)...(35)
<223> OTHER INFORMATION: Xaa = any amino acid

<400> SEQUENCE: 108

Lys Lys Thr Val Val Val Glu Ser Tyr Val Val Asp Val Pro Glu Gly
  1               5                  10                  15

Xaa Xaa Glu Glu Xaa Thr Xaa Xaa Phe Xaa Asp Xaa Ile Xaa Xaa Xaa
             20                  25                  30

Asn Leu Xaa Ser Leu Ala Lys Leu
         35                  40

<210> SEQ ID NO 109
<211> LENGTH: 6
<212> TYPE: PRT
<213> ORGANISM: Artificial Sequence
<220> FEATURE:
<223> OTHER INFORMATION: synthetic 6X-His tag

<400> SEQUENCE: 109

His His His His His His
  1               5

<210> SEQ ID NO 110
<211> LENGTH: 20
<212> TYPE: DNA
<213> ORGANISM: Artificial Sequence
<220> FEATURE:
<223> OTHER INFORMATION: synthetic real-time quantitiative PCR oligo-
      dT-20

<400> SEQUENCE: 110
tttttttttt tttttttttt                                             20

<210> SEQ ID NO 111
<211> LENGTH: 25
<212> TYPE: DNA
<213> ORGANISM: Artificial Sequence
<220> FEATURE:
<223> OTHER INFORMATION: synthetic magnetic bead oligo-dT-25

<400> SEQUENCE: 111
tttttttttt tttttttttt ttttt                                       25
```